US011674179B2

(12) United States Patent
Snyder et al.

(10) Patent No.: US 11,674,179 B2
(45) **Date of Patent: *Jun. 13, 2023**

(54) THERAPEUTIC REGIMEN FOR HYPERTENSION

(71) Applicant: Geneticure Inc., Minnetonka, MN (US)

(72) Inventors: Eric Snyder, Rochester, MN (US); Ryan Sprissler, Tucson, AZ (US); Scott C. Snyder, Minnetonka, MN (US)

(73) Assignee: Geneticure Inc., Minnetonka, MN (US)

( * ) Notice: Subject to any disclaimer, the term of this patent is extended or adjusted under 35 U.S.C. 154(b) by 245 days.

This patent is subject to a terminal disclaimer.

(21) Appl. No.: 16/789,383

(22) Filed: Feb. 12, 2020

(65) Prior Publication Data

US 2020/0263253 A1 Aug. 20, 2020

Related U.S. Application Data

(63) Continuation of application No. 15/314,641, filed as application No. PCT/US2015/032651 on May 27, 2015, now Pat. No. 10,590,485.

(60) Provisional application No. 62/004,460, filed on May 29, 2014.

(51) Int. Cl.
*C12Q 1/68* (2018.01)
*C12Q 1/6883* (2018.01)
*G01N 33/68* (2006.01)

(52) U.S. Cl.
CPC ....... *C12Q 1/6883* (2013.01); *G01N 33/6893* (2013.01); *C12Q 2600/106* (2013.01); *C12Q 2600/156* (2013.01); *G01N 2800/321* (2013.01)

(58) Field of Classification Search
None
See application file for complete search history.

(56) References Cited

U.S. PATENT DOCUMENTS

| | | | | |
|---|---|---|---|---|
| 6,316,196 B1 * | 11/2001 | Morten | ................ | C12Q 1/6883 536/23.4 |
| 6,376,182 B1 | 4/2002 | Chao et al. | | |
| 10,465,246 B2 | 11/2019 | Snyder et al. | | |
| 10,590,485 B2 | 3/2020 | Snyder et al. | | |
| 2007/0092888 A1 | 4/2007 | Diamond et al. | | |
| 2017/0175193 A1 | 6/2017 | Snyder et al. | | |
| 2018/0195128 A1 | 7/2018 | Snyder et al. | | |
| 2020/0299771 A1 | 9/2020 | Snyder et al. | | |

FOREIGN PATENT DOCUMENTS

| | | |
|---|---|---|
| EP | 3149487 B1 | 2/2020 |
| WO | WO-02071070 A2 | 9/2002 |
| WO | WO-2011048033 A2 | 4/2011 |
| WO | WO-2015183938 A1 | 12/2015 |

OTHER PUBLICATIONS

"U.S. Appl. No. 15/314,641, Preliminary Amendment filed Jan. 30, 2017", 4 pgs.
"U.S. Appl. No. 15/314,641, Advisory Action dated Aug. 20, 2019", 3 pgs.
"U.S. Appl. No. 15/314,641, Examiner Interview Summary dated Sep. 5, 2019", 2 pgs.
"U.S. Appl. No. 15/314,641, Final Office Action dated May 3, 2019", 10 pgs.
"U.S. Appl. No. 15/314,641, Non Final Office Action dated Oct. 5, 2018", 13 pgs.
"U.S. Appl. No. 15/314,641, Notice of Allowance dated Nov. 5, 2019", 15 pgs.
"U.S. Appl. No. 15/314,641, Preliminary Amendment filed Nov. 29, 2016", 17 pgs.
"U.S. Appl. No. 15/314,641, Response filed Jan. 7, 2019 to Non Final Office Action dated Oct. 5, 2018", 20 pgs.
"U.S. Appl. No. 15/314,641, Response filed Jul. 31, 2019 to Final Office Action dated May 3, 2019", 25 pgs.
"U.S. Appl. No. 15/314,641, Response filed Sep. 3, 2019 to Advisory Action dated Aug. 20, 2019", 13 pgs.
"U.S. Appl. No. 15/314,641, Resposne filed Jun. 28, 2018 to Restriction Requirement dated May 25, 2018", 9 pgs.
"U.S. Appl. No. 15/314,641, Restriction Requirement dated May 25, 2018", 7 pgs.
"U.S. Appl. No. 15/314,641, Second Supplemental Preliminary Amendment filed Jan. 19, 2018", 17 pgs.
"U.S. Appl. No. 15/314,641, Supplemental Preliminary Amendment filed Jul. 25, 2017", 25 pgs.
"U.S. Appl. No. 15/894,546, Advisory Action dated Jul. 22, 2019", 3 pgs.
"U.S. Appl. No. 15/894,546, Advisory Action dated Aug. 20, 2019", 5 pgs.
"U.S. Appl. No. 15/894,546, Final Office Action dated Apr. 16, 2019", 11 pgs.
"U.S. Appl. No. 15/894,546, Non Final Office Action dated Oct. 5, 2018", 15 pgs.
"U.S. Appl. No. 15/894,546, Notice of Non-Compliant Amendment dated Jul. 22, 2019", 3 pgs.
"U.S. Appl. No. 15/894,546, Response filed Jan. 7, 2019 to Non Final Office Action dated Oct. 5, 2018", 20 pgs.
"U.S. Appl. No. 15/894,546, Response filed Jun. 25, 2018 to Restriction Requirement dated May 18, 2018", 13 pgs.
"U.S. Appl. No. 15/894,546. Response filed Jun. 11, 2019 to Final Office Action dated Apr. 16, 2019", 25 pgs.
"U.S. Appl. No. 15/894,546, Response filed Aug. 7, 2019 to Advisory Action dated Jul. 22, 2019", 27 pgs.
"U.S. Appl. No. 15/894,546, Restriction Requirement dated May 18, 2018", 8 pgs.
"European Application Serial No. 15728326.8, Communication Pursuant to Article 94(3) EPC dated Feb. 8, 2019", 5 pgs.
"European Application Serial No. 15728326.8, Communication Pursuant to Article 94(3) EPC dated Jan. 24, 2018", 6 pgs.

(Continued)

*Primary Examiner* — Jehanne S Sitton
(74) *Attorney, Agent, or Firm* — Schwegman Lundberg & Woessner, P.A.

(57) ABSTRACT

The invention relates to improved methods, devices, and kits for identifying and implementing an appropriate treatment regimen for subjects suffering from hypertension.

7 Claims, 8 Drawing Sheets

Specification includes a Sequence Listing.

(56) References Cited

OTHER PUBLICATIONS

"European Application Serial No. 15728326.8, Communication Pursuant to Article 94(3) EPC dated Sep. 6, 2018", 5 pgs.
"European Application Serial No. 15728326.8, Response Filed Jan. 11, 2019 to Communication Pursuant to Article 94(3) EPC dated Sep. 6, 2018", 48 pgs.
"European Application Serial No. 15728326.8, Response filed Jun. 4, 2018 to Communication Pursuant to Article 94(3) EPC dated Jan. 24, 2018", 58 pgs.
"European Application Serial No. 15728326.8, Response filed Jun. 12, 2019 to Communication Pursuant to Article 94(3) EPC dated Feb. 8, 2019", 21 pgs.
"European Patent Application Serial No. 15728326.8, Voluntary Amendment filed on Aug. 1, 2017", 22 pgs.
"International Application Serial No. PCT/US2015/032651, International Preliminary Report on Patentability dated Dec. 8, 2016", 15 pgs.
"International Application Serial No. PCT/US2015/032651, International Search Report dated Oct. 21, 2015", 8 pgs.
"International Application Serial No. PCT/US2015/032651, Invitation to Pay Add'l Fees and Partial Search Report dated Aug. 11, 2015", 8 pgs.
"International Application Serial No. PCT/US2015/032651, Written Opinion dated Oct. 21, 2015", 13 pgs.
"Notice of Intent to Grant", EPO Form 2004C—Communication Under Rule 71(3) EPC, Intention to Grant, 163.
Baudin, B., et al., "Angiotensin II receptor polymorphisms in hypertension. Pharmacogenomic considerations", Pharmacogenomics 2002;3, (2002), 65-73.
Bengtsson, K, et al., "Polymorphism in the betal-adrenergic receptor gene and hypertension", Circulation, Lippincott Williams & Wilkins, US, vol. 104, No. 2. (Jul. 10, 2001), 187-190.
Brodde, Otto-Erich, "The functional importance of betal and beta2 adrenoceptors in the human heart", The American Journal of Cardiology, 62(5), (Aug. 11, 1988), 24C-29C.
Calhoun, David A., et al., "Resistant Hypertension: Diagnosis, Evaluation, and Treatment", Circulation. 2008;117: e510-e526, (2008), 18 pgs.
Chobanian, Aram V., et al., "The Seventh Report of the Joint National Committee on Prevention, Detection, Evaluation, and Treatment of High Blood Pressure", American Medical Association; vol. 289, No. 19; 2560-2572, (2003), 14 pgs.
Hesse, C, et al., "Genetic Variation in the [beta]2-Adrenergic Receptor: Impact on Intermediate Cardiovascular Phenotypes", Current Pharmacogenomics And Personalized Medicine, vol. 6, No. 3, (Sep. 1, 2008), 160-170.
Jin, Hyun-Seok, et al., "Genetic Variations in the Sodium Balance-Regulating Genes ENaC , NEDD4L , NDFIP2 and USP2 Influence Blood Pressure and Hypertension", Kidney Blood Press Res 2010;33:15-23, (2010), 9 pgs.
Johnson, J.A., et al., "Hypertension pharmacogenomics: Current status and future directions", Current Opinion in Molecular Therapeutics, 7(3), (2005), 218-225.
Kearney, P.M., et al., "Global burden of hypertension: analysis of worldwide data", The Lancet, 365(9455), (Jan. 15, 2005), 217-223.
La Rosee, Karl, et al.. "The ARG389GLY Beta1-Adrenoceptor Gene Polymorphism Determines Contractile Response to Catecholamines", Pharmacogenetics, 14(11), (Nov. 2004), 711-716.
Liu, Jie, et al., "Gly389arg polymorphism of [beta] 1-adrenergic receptor is associated with the cardiovascular response to metoprolol", Clin Pharmacol Ther 2003;74, (2003), 372-379.
McNamara, Dennis M., et al., "Pharmacogenetic Interactions Between Angiotensin-Converting Enzyme Inhibitor Therapy and the Angiotensin-Converting Enzyme Deletion Polymorphism in Patients With Congestive Heart Failure", J Am Coll Cardiol 2004;44, (2004), 2019-2026.
Meisler, MH, et al., "SCNN1, an Epithelial Cell Sodium Channel Gene in the Conserved Linkage Group on Mouse Chromosome 6 and Human Chromosome 12", Genomics 1994;24, (1994), 185-186.
Miller, Judith A., et al., "Angiotensin II type 1 receptor gene polymorphism predicts response to losartan and angiotensin II", Kidney International, vol. 56 (1999), (1999), 2173-2180.
Patel, et al., "Genome Medicine", vol. 5:58, (2013), 14 pgs.
Pilati, Mara, et al., "The role of angiotensin-converting enzyme polymorphism in congestive heart failure", Congest Heart Fail 2004;10:87-93,quiz 94-95, (2004), 9 pgs.
Pilbrow, Anna P., "Angiotensinogen M235T and T174M Gene Polymorphisms in Combination Doubles the Risk of Mortality in Heart Failure", Hypertension 2007;49:322-327, (2007), 7 pgs.
Pratt, J. Howard, "Central Role for ENaC in Development of Hypertension", J Am Soc Nephrol 16:, (2005), 3154-3159.
Psaty, Bruce M., et al., "Diuretic therapy, the alpha-adducin gene variant, and the risk of myocardial infarction or stroke in persons with treated hypertension", JAMA 2002;287, (2002), 1680-1689.
Reddy, Sushma, et al., "Adrenergic receptor genotype influences heart failure severity and [beta]-blocker response in children with dilated cardiomyopathy", Pediatric Research, vol. 77, No. 2, (Nov. 19, 2014), 363-369.
Snyder, Em, et al., "Blood pressure variation in healthy humans: A possible interaction with 8-2 adrenergic receptor genotype and renal epithelial sodium channels", Med Hypotheses 2005;65, (2005), 296-299.
Snyder, Em, et al., "Genotype related differences in beta2 adrenergic receptor density and cardiac function", Med Sci Sports Exerc 2006;38, (2006), 882-886.
Snyder, Eric M., et al., "Effects of an inhaled beta2-agonist on cardiovascular function and sympathetic activity in healthy subjects", Pharmacotherapy 2011;31, (2011), 748-756.
Snyder, Eric M., et al., "Genetics of β2-Adrenergic Receptors and the Cardiopulmonary Response to Exercise", Exerc Sport Sci Rev. Apr. 2008 ; 36(2): 98-105, (2008), 16 pgs.
Snyder, Eric M, et al., "The Arg16Gly polymorphism of the [beta] 2-adrenergic receptor and the natriuretic response to rapid saline infusion in humans", The Journal Of Physiology, vol. 574, No. 3, (Jul. 21, 2006), 947-954.
Tang, W., et al., "Associations between angiotensinogen gene variants and left ventricular mass and function in the HyperGEN study", Am Heart J 2002;143, (2002), 854-860.
Turner, Stephen T et al., "WNK1 Kinase Polymorphism and Blood Pressure Response to a Thiazide Diuretic", Hypertension 2005;46:758-765, (2005), 9 pgs.
Ulgren, Ms, et al., "The relationship between angiotensin-converting enzyme (insertion/deletion) gene polymorphism and left ventricular remodeling in acute myocardial infarction", Coron Artery Dis 2007;18, (2007), 153-157.
Vangjeli, Ciara, et al., "Confirmation that the renin gene distal enhancer polymorphism ren-5312c/t is associated with increased blood pressure", Circulation Cardiovascular genetics 2010;3:53-59, (2010), 17 pgs.
Zhang, Li-Na, et al., "Association between polymorphisms of alpha-adducin gene and essential hypertension in chinese population", BioMed research international 2013;2013:451094, (2013), 5 pgs.
"U.S. Appl. No. 15/894,546, Notice of Allowance dated Sep. 3, 2019", 15 pgs.
"U.S. Appl. No. 15/894,546, Preliminary Amendment filed Feb. 12, 2018", 16 pgs.

* cited by examiner

THERAPEUTIC REGIMEN FOR HYPERTENSION

CROSS REFERENCE TO RELATED APPLICATIONS

This application is a continuation of U.S. patent application Ser. No. 15/314,641, filed Nov. 29, 2016, which is a U.S. National Stage Filing under 35 U.S.C. § 371 from International Application No. PCT/US2015/032651, filed May 27, 2015, and published as WO 2015/183938 on Dec. 3, 2015, which application claims benefit of the priority filing date of U.S. Provisional Application Ser. No. 62/004,460, filed May 29, 2014, the contents of which applications are specifically incorporated herein by reference in their entireties.

BACKGROUND

Hypertension (high blood pressure) is one of the most significant preventable contributors to disease and death in the world and represents the most common condition seen in the primary care setting (Kearney et al., *Lancet* 365:217-223 (2005)). According to the American Heart Association, approximately 78 million adults (1 in 3) living in the United States have hypertension with more than 5 million new diagnoses made each year. Of these individuals, 82% are aware they have it, 75% are currently being treated for it, but only 52% have their blood pressure under control (thus, ~48% do not have adequate blood pressure control).

Hypertension can lead to myocardial infarction (heart attack), stroke, renal failure, and death if not detected early and treated appropriately. In 2009, high blood pressure was listed as a primary or contributing cause of death in about 350.000 of the approximate 2.4 million U.S. deaths (14% of all deaths). From 1999-2009 the number of deaths attributable to hypertension increased by 44%.

Refractory (or resistant) hypertension is defined as blood pressure that remains above clinical guideline goals in spite of concurrent use of three antihypertensive agents of different classes. Critically, refractory hypertension is noted in approximately 25-30% of all individuals being treated for hypertension. Refractory hypertension is a common clinical problem which contributes to the high levels of morbidity and mortality. In 2009, the direct and indirect economic burden on the United States health care system associated with hypertension was estimated at $51 billion.

Globally, nearly 1 billion individuals have been diagnosed with hypertension, with an estimate of an additional 400 million living with undiagnosed hypertension. Hypertension is the leading cause of premature death and the leading cause of cardiovascular disease worldwide. Similar to the continued upward trend in prevalence as seen in the United States, it is estimated that in 2025 about 1.56 billion adults will be living with hypertension. Because nearly two-thirds of the people living with hypertension worldwide reside in developing countries, providing optimal treatment at the lowest cost is critically important.

Unfortunately, despite a significant impulse in the medical community to move towards an "individualized medicine" approach to patient centered treatment, the current clinical treatment strategy is based on a set algorithm which does not take into account individual patient differences. Rather, physicians are guided to choose a drug (one out of many options) in a given class of drugs and use that specific drug as a "first line therapy" (typically initiating with the diuretic class) and titrate that specific drug of choice to therapeutic dosage regardless of efficacy. It is only after a prolonged course of treatment with that specific class of drug that clinical efficacy is determined (typically three months). At this stage, if clinical guideline goals for blood pressure have not been met, it is often recommended that the patient remain on the "first line therapy" whilst an additional drug from a different class of drugs (typically an Angiotensin converting enzyme inhibitor (ACE inhibitor) or Angiotensin II receptor blocker (ARB)) is added to the pharmacologic regimen. Again, this drug is titrated to recommended therapeutic dosage and another prolonged course of treatment is initiated before clinical efficacy is determined (an additional three months-six months since initiation of treatment). If at this point, clinical guideline goals for blood pressure have not been met, a third drug from a third class of drugs (typically a beta-blocker) is added and the process is repeated (another three months-nine months from initiation of treatment). Further, if clinical guideline goals have continued to be elusive, the diagnosis of refractory hypertension is added and the process is reinitiated with a different combination of drugs, different classes of drugs, different drug options within a given class of drugs, different dosages, or all of the above. Thus, from the time of initial diagnosis and the start of treatment to the point in which blood pressure is adequately controlled may take anywhere from three months to well over one year. This trial-and-error standard of care is clearly not optimal.

SUMMARY

The invention relates to improved methods, devices, and kits for identifying and implementing an appropriate treatment regimen for subjects suffering from hypertension. The methods, devices, and kits comprehensively assess common genetic variants in the cardiac, vascular, and renal systems in an effort to improve therapeutic guidance for high blood pressure treatment. Detection of an individual's genetic variants permits selection appropriate drug classes for that individual. Clinicians can then guide blood pressure therapy using knowledge that is specific to their individual patient, rather than the currently employed "trial-and-error" procedures that are based on population data and use of drugs with the least initial side effects.

One aspect of the invention is a method that includes:

(a) administering a loop diuretic to a subject as a first line therapy, without a beta blocker and without a vasodilator, if the subject's genome comprises a WNK1 nucleic acid with a cytosine at the variable position of rs1159744 or rs2107614;

(b) administering a hydrochlorothiazide to a subject as a first line therapy, without a beta blocker and without a vasodilator, if the subject's genome comprises an ADD1 nucleic acid with a thymine at the variable position of rs4961, or if the test sample comprises a SLC12A3 nucleic acid with a thymine at the variable position of rs1529927; or (c) administering a hydrochlorothiazide to a subject as a first line therapy, without a beta blocker and without a vasodilator, if the subject's genome comprises an ADD1 nucleic acid with a thymine at the variable position of rs4961, or if the test sample comprises a SLC12A3 nucleic acid with a thymine at the variable position of rs1529927.

Another aspect of the invention is a method that includes: administering a beta-blocker drug to a subject as a first line therapy, without a diuretic and without a hydrochlorothiazide, if the subject's genome does not comprise:

(a) a WNK1 nucleic acid with a cytosine at the variable position of rs1159744;
(b) a WNK1 nucleic acid with a cytosine at the variable position of rs2107614;
(c) an ADD1 nucleic acid with a thymine at the variable position of rs4961; or
(d) a SLC12A3 nucleic acid with a thymine at the variable position of rs1529927
but the subject's genome does comprise:
1. a CYP2D6 nucleic acid with an adenine at the variable position of Rs3892097;
2. an ADRB1 nucleic acid with a cytosine at the variable position of rs1801253;
3. an ADRB1 nucleic acid with an adenine at the variable position of rs1801252;
4. an ADRB2 nucleic acid with a guanine at the variable position of rs1042714; or
5. an ADRB2 nucleic acid with a guanine at the variable position of rs1042713.

Another aspect of the invention is a method that includes: administering an angiotensin II receptor blocker to a subject as a first line therapy, without a diuretic, without a hydrochlorothiazide, and without a beta-blocker, if the subject's genome does not comprise:
(a) a WNK1 nucleic acid with a cytosine at the variable position of rs1159744;
(b) a WNK1 nucleic acid with a cytosine at the variable position of rs2107614;
(c) an ADD1 nucleic acid with a thymine at the variable position of rs4961; or
(d) a SLC12A3 nucleic acid with a thymine at the variable position of rs1529927
but the subject's genome does comprise:
1. a renin nucleic acid with a cytosine at the variable position of rs12750834; or
2. an AGT1R nucleic acid with a cytosine at the variable position of rs5186.

Another aspect of the invention is a method that includes: administering an ACE inhibitor to a subject without an angiotensin II receptor blocker as a first line therapy, without a diuretic, without a hydrochlorothiazide, and without a beta-blocker, if the subject's genome does not comprise:
(a) WNK1 nucleic acid with a cytosine at the variable position of rs1159744;
(b) a WNK1 nucleic acid with a cytosine at the variable position of rs2107614;
(c) an ADD1 nucleic acid with a thymine at the variable position of rs4961; or
(d) a SLC12A3 nucleic acid with a thymine at the variable position of rs1529927
but the subject's genome does comprise:
1. an ACE nucleic acid with a deletion in rs1799752; or
2. an AGT nucleic acid with a cytosine at the variable position of rs699.

Another aspect of the invention is a method that includes: administering an amiloride as a first line therapy to a subject without an ACE inhibitor, without an angiotensin II receptor blocker, without a diuretic, without a hydrochlorothiazide, and without a beta-blocker, if the subject's genome does not comprise:
1. a WNK1 nucleic acid with a cytosine at the variable position of rs1159744;
2. a WNK1 nucleic acid with a cytosine at the variable position of rs2107614;
3. an ADD1 nucleic acid with a thymine at the variable position of rs4961; or
4. a SLC12A3 nucleic acid with a thymine at the variable position of rs1529927.
but if the subject's genome does comprise a SCNN1A nucleic acid with an adenine at the variable position of rs2228576.

The methods can also include administering a second line therapy drug after administration of the first line therapy for at least 1 month, wherein the second line therapy drug is selected from the group consisting of diuretic, a beta-blocker, an ACE inhibitor, a vasodilator, and a combination thereof.

Devices, compositions, methods, and kits are also described herein for identifying and implementing an appropriate treatment regimen for subjects suffering from hypertension.

DESCRIPTION OF THE FIGURES

FIG. 3B shows the same process but without the steps of DNA Stocks Storage and Future Testing if the sample Passes Yield and Purity Assays.

DETAILED DESCRIPTION

Methods, devices, and kits are described herein for selecting individualized hypertension treatment regimens that are more effective than currently available regimens. The methods, devices, and kits include assays for identifying genetic variants in individual subjects that make the individual more or less responsive to specific medications. When the appropriate medication is administered, the subject's blood pressure is appropriately controlled, and side effects are avoided.

Genetic variants present in genes such as ADRB1, ADRB2, CYP2D6, angiotensin converting enzyme (ACE), angiotensinogen, angiotensin receptor, renin, $Na^+$ channels (such as SCNN1A), adducin, sodium ($Na^+$) chloride ($Cl^-$) co-transporters (such as SLC12A3), and/or WNK1 genes are correlated with heightened or reduced responsiveness to various blood pressure medications. Although there are a number of hypertension drugs available on the market, subjects react differently to such drugs. The kits, methods, and devices described herein are useful for detecting which subjects benefit from which therapeutic regimen.

High Blood Pressure (Hypertension)

The development of high blood pressure in humans is the result of one or more of three physiologic maladaptations: 1) elevated cardiac output (liters of blood ejected from the heart per minute) that increases the amount of blood pressing against the vessels, 2) relatively narrow blood vessels that results in increased pressure towards the lumen of the blood vessel due to Poiseuille's Law (which describes the inverse relationship between the diameter of a tube (vessel) and the pressure against the walls of the tube (vessel), all else being equal), or 3) increased sodium ($Na^+$) absorption in the kidney which results in increased blood volume (and the amount of blood pumped per minute, cardiac output) and subsequently increased outward pressure against the tubes (vessels).

Figure 1:
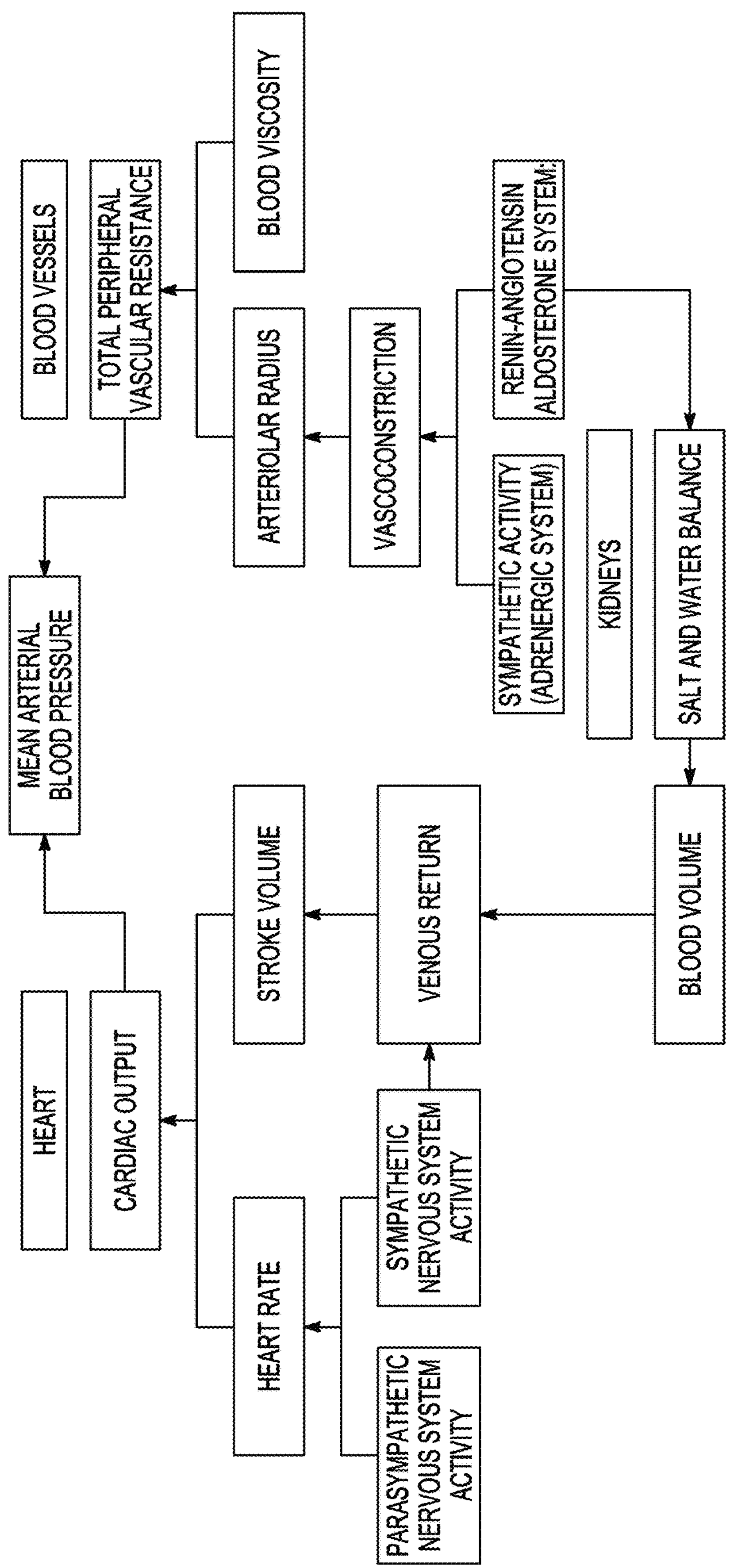
FIG. 1 is a schematic diagram illustrating the interplay between the heart, blood vessels, and kidney in blood pressure regulation.
Figure 2:
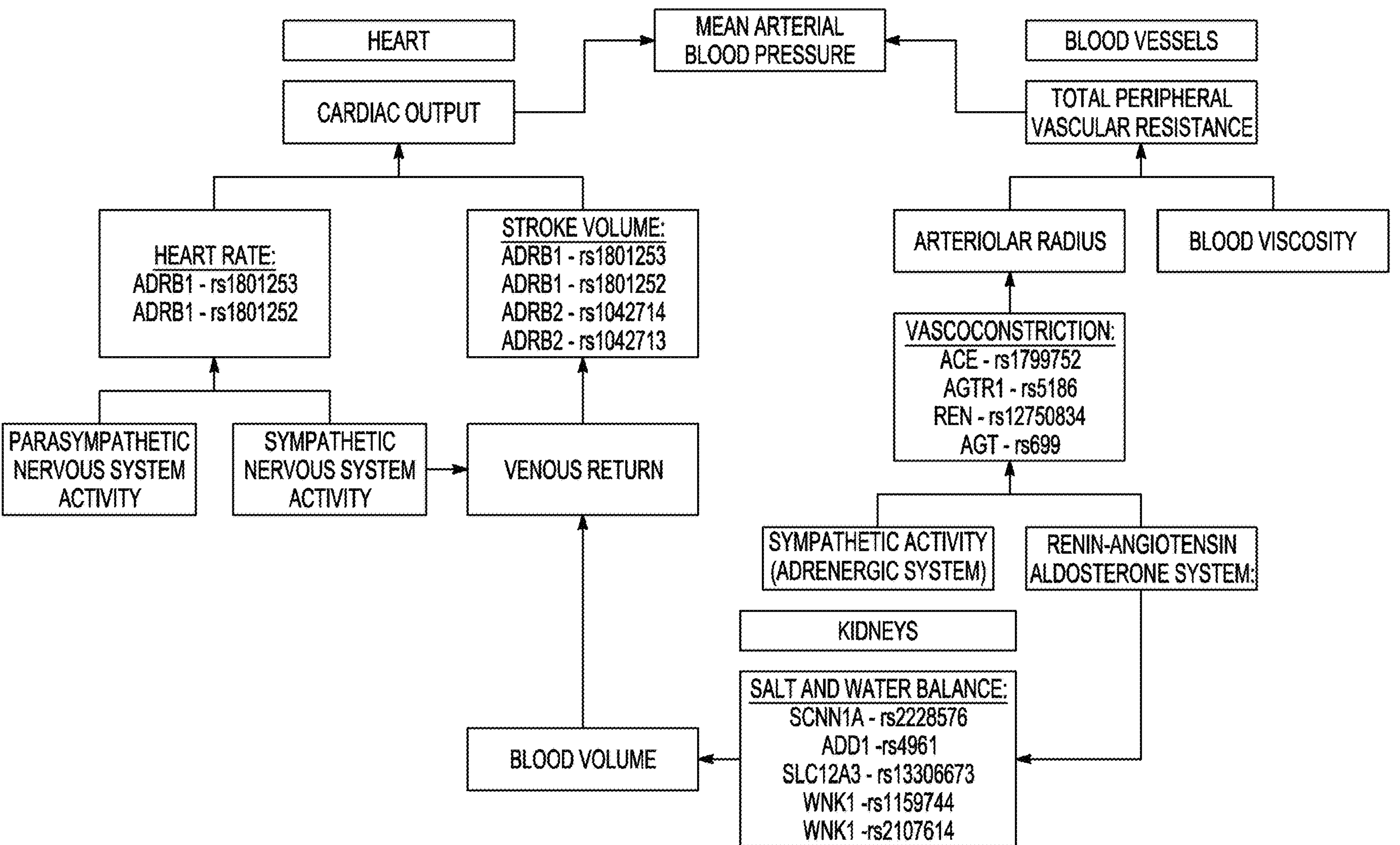
FIG. 2 is a schematic diagram illustrating of the types of genes useful for evaluating hypertension, and representative single nucleotide polymorphisms that are correlated with blood pressure drug responses.

Blood pressure is highly regulated and tightly controlled in humans, such that in the event of a drop in cardiac output, the heart sends a signal to the kidneys (via the proteins atrial natriuretic peptide and brain-type natriuretic peptide, among others) and vessels with the ultimate function of increasing $Na^+$ reabsorption to increase plasma volume and vasoconstriction to increase blood pressure. Similarly, if there is a drop in blood pressure, there is an increase in cardiac output (primarily via an immediate increase in heart rate through inhibition of the parasympathetic nervous system) to compensate and an increase in the renin-angiotensin aldosterone system which results in both constriction of blood vessels (which increases blood pressure) and an increase in $Na^+$ and, therefore, fluid retention in the kidney, which increases plasma volume and can increase blood pressure. Hence, the human body provides redundant functions to maintain blood pressure both in the short-term and in the long-term, by regulating the interplay between the heart, blood vessels, and kidney. FIG. 1 is a schematic diagram illustrating the interplay between the heart, blood vessels, and kidneys involved in regulating blood pressure.

Blood pressure therapy following diagnosis traditionally follows a regimented algorithm based on therapies effective across the general population. Currently, clinicians start a patient who has been diagnosed with high blood pressure on a diuretic (to reduce renal $Na^+$ reabsorption). If such a diuretic does not work within a period of time, the clinician next tries a vasodilator, and if this is not effective, then a clinician will lastly prescribe a beta-blocker. This trial-and-error process to lower a patient's blood pressure can take several months, is costly, and threatens the health of the patient because the patient's hypertension is frequently not adequately controlled in a timely manner.

Such currently available methods are in stark contrast to the methods, devices, and kits described herein that involve specifically testing an individual's genetic profile and, as illustrated herein, basing therapeutic treatment on the results of such testing. Hence, the methods, devices, and kits described herein for evaluating a blood pressure genetic panel to improve treatment of hypertensive subjects, by quickly identifying more effective medications, thereby avoiding side effects and delays in treatment. Applicants' methods are therefore an improvement over the currently available trial-and-error procedures that frequently result in side effects and delays in effective treatment.

Ranking of Genotypes that Affect Therapy

The genotype of a subject can significantly affect the response of the subject to blood pressure medications because certain functional polymorphisms have greater effects on the physiology of a subject than others. The following is a summary of polymorphisms in order of their impact on blood pressure and which drugs should be employed by subjects with such genetic variations.

1. Subjects with the WNK1 polymorphism defined by rs1159744 (SEQ ID NO:34, with cytosine at the variable position), benefit more from loop diuretics.
2. Subjects with the WNK1 polymorphism defined by rs2107614 (SEQ ID NO:33, with cytosine at the variable position), benefit more from loop diuretics.
3. Subjects with the ADD1 polymorphism defined by rs4961 (SEQ ID NO:27, with thymine at the variable position), benefit more from hydrochlorothiazides.
4. Subjects with the SLC12A3 polymorphism defined by rs1529927 (SEQ ID NO:30, with thymine at the variable position), benefit more from hydrochlorothiazides.

Any homozygous combination at one or more of the WNK1 Rs1159744, WNK1 Rs2107614, ADD1 Rs4961, and SLC12A3 rs1529927 polymorphisms means that diuretics should be the first-line therapy, especially if the patient is heterozygous for polymorphisms in genes responsive to beta-blockers or vasodilators.

5. Subjects with the CYP2D6 polymorphism defined by Rs3892097 (SEQ ID NO:10, with adenine at the variable position), plus the ADRB1 polymorphism defined by rs1801253 (SEQ ID NO:3, with cytosine as the variable nucleotide), plus the ADRB1 polymorphism defined by rs1801252 (SEQ ID NO:2, with adenine as the variable nucleotide) benefit from beta-blockade classes of drugs.
6. Subjects with the renin polymorphism defined by rs12750834 (SEQ ID NO:20, with cytosine as the variable nucleotide) plus the AGT1R polymorphism defined by rs5186 (SEQ ID NO: 16, with cytosine as the variable nucleotide), which affect responses to angiotensin II receptor blockers.
7. Subjects with the ACE deletion defined by Rs1799752 (SEQ ID NO:35) and the AGT polymorphism defined by rs699 (SEQ ID NO:14, with cytosine as the variable nucleotide) can benefit from the combination of an angiotensin II receptor blocker and an ACE inhibitor.
8. Subjects with the SCNN1A polymorphism defined by rs2228576 (SEQ ID NO:22, with adenine as the variable position) can benefit from administration of amiloride.
9. Subjects with the ADRB2 polymorphism defined by rs1042714 (SEQ ID NO:7, with guanine as the variable nucleotide) can benefit from administration of a non-selective beta-blockade.
10. Subjects with the ADRB2 polymorphism defined by rs1042713 (SEQ ID NO:6, with guanine as the variable nucleotide) can benefit from administration of a non-selective beta-blockade.

All patients do not respond to same. Some subjects have genotypes that can significantly affect their response to medications. When clinicians employ currently available procedures (diuretic first, then vasodilator, then beta blocker), some patients will benefit but others will not respond or will respond negatively. Hence, some patients would benefit from initial administration of a vasodilator or a beta-blocker, rather than a diuretic.

Beta-Blocker Responsive Polypeptides and Nucleic Acids

There are two primary receptors within the heart that influence both heart rate (chronotropic effect) and heart contractility (inotropic effect) (Brodde, *Am J Cardiol* 62:24C-29C (1988), the beta-1 adrenergic receptors ($\beta_1$AR, encoded by the ADRB1 gene) and the beta-2 adrenergic receptors ($\beta_2$AR, encoded by the ADRB2 gene).

The heart is primary comprised of beta-1 adrenergic receptors, which are located on 80% of the ventricular wall surface, 70% of the atrial wall surface, and 95% of the sino-atrial (SA) node. The atria of the heart receive blood that returns from the body (right atria) of lungs (left atria) whereas the ventricles pump blood to the lungs (right ventricle) and body (left ventricle). The sino-atrial node primarily controls heart rate.

Although heart rate and cardiac contractility are primarily regulated by $\beta_1$AR, the $\beta_2$AR also play a role, primarily in cardiac contractility. Stimulation of either $\beta_1$AR or $\beta_2$AR can influence heart rate and cardiac contractility through increases in intracellular c-AMP and protein kinase A (PKA) which, ultimately, alter $Ca^+$-channel sensitivity and reduce the threshold needed for an action potential. Therefore, cardiac output (and blood pressure) can be increased through increases in $\beta_1$AR and/or $\beta_2$AR activities. If a variant $\beta_1$AR or $\beta_2$AR gene encodes a more functional receptor, cardiac output is increased.

$\beta_1$AR and $\beta_2$AR activities can be modulated through the use of selective (e.g., atenolol and metoprolol) and non-selective (e.g., propranolol and carvedilol) beta-blockers. The selective beta-blockers are selective for inhibiting the $\beta_1$AR. The non-selective beta-blockers inhibit both $\beta_1$AR and $\beta_2$AR. Both types of beta-blockers tend to decrease blood pressure through a decrease in heart rate and cardiac contractility, which ultimately results in a decrease in cardiac output. Similarly, the administration of a $\beta_2$AR-agonist (e.g., albuterol sulfate) tends to increase cardiac output and heart rate (Snyder et al., *Pharmacotherapy* 31:748-756 (2011)). Thus, both $\beta_1$AR and $\beta_2$AR are important in the regulation of cardiac output.

Just as stimulation of these receptors can elevate cardiac output and increase blood pressure, so too can genetic variation of the genes that encode $\beta_1$AR and $\beta_2$AR (ADRB1 and ADRB2) elevate receptor activity and increase blood pressure. Conversely, some ADRB1 and ADRB2 genetic variants encode receptors with reduced activity. In addition, some ADRB1 and ADRB2 genetic variants exhibit reduced, or enhanced, responsiveness to blood pressure medications such as beta-blockers. Not all individuals respond similarly to beta-blockade, despite similar clinical and environmental conditions. As described herein, the effectiveness of beta-blockers is dependent to some extent upon the genetic make-up of the subjects to which the beta-blockers are administered.

Sequences for various adrenergic receptors are available, for example, from the National Center for Biotechnology Information (see website at ncbi.nlm.nih.gov).

For example, a full length human ADRB1 cDNA nucleotide sequence is available from the database maintained by the National Center for Biotechnology Information (see website at ncbi.nlm.nih.gov), which has accession number NM_00064 (GI:110349783), and is shown below as SEQ ID NO:1.

1 GCACCACGCC GCCCGGGCTT CTGGGGTGTT CCCCAACCAC

41 GGCCCAGCCC TGCCACACCC CCCGCCCCCG GCCTCCGCAG

81 CTCGGCATGG GCGCGGGGGT GCTCGTCCTG GGCGCCTCCG

121 AGCCCGGTAA CCTGTCGTCG GCCGCACCGC TCCCCGACGG

161 CGCGGCCACC GCGGCGCGGC TGCTGGTGCC CGCGTCGCCG

201 CCCGCCTCGT TGCTGCCTCC CGCCAGCGAA AGCCCCGAGC

241 CGCTGTCTCA GCAGTGGACA GCGGGCATGG GTCTGCTGAT

281 GGCGCTCATC GTGCTGCTCA TCGTGGCGGG CAATGTGCTG

321 GTGATCGTGG CCATCGCCAA GACGCCGCGG CTGCAGACGC

361 TCACCAACCT CTTCATCATG TCCCTGGCCA GCGCCGACCT

401 GGTCATGGGG CTGCTGGTGG TGCCGTTCGG GGCCACCATC

441 GTGGTGTGGG GCCGCTGGGA GTACGGCTCC TTCTTCTGCG

481 AGCTGTGGAC CTCAGTGGAC GTGCTGTGCG TGACGGCCAG

521 CATCGAGACC CTGTGTGTCA TTGCCCTGGA CCGCTACCTC

561 GCCATCACCT CGCCCTTCCG CTACCAGAGC CTGCTGACGC

601 GCGCGCGGGC GCGGGGCCTC GTGTGCACCG TGTGGGCCAT

641 CTCGGCCCTG GTGTCCTTCC TGCCCATCCT CATGCACTGG

681 TGGCGGGCGG AGAGCGACGA GGCGCGCCGC TGCTACAACG

721 ACCCCAAGTG CTGCGACTTC GTCACCAACC GGGCCTACGC

761 CATCGCCTCG TCCGTAGTCT CCTTCTACGT GCCCCTGTGC

801 ATCATGGCCT TCGTGTACCT GCGGGTGTTC CGCGAGGCCC

841 AGAAGCAGGT GAAGAAGATC GACAGCTGCG AGCGCCGTTT

881 CCTCGGCGGC CCAGCGCGGC CGCCCTCGCC CTCGCCCTCG

921 CCCGTCCCCG CGCCCGCGCC GCCGCCCGGA CCCCCGCGCC

961 CCGCCGCCGC CGCCGCCACC GCCCCGCTGG CCAACGGGCG

1001 TGCGGGTAAG CGGCGGCCCT CGCGCCTCGT GGCCCTGCGC

1041 GAGCAGAAGG CGCTCAAGAC GCTGGGCATC ATCATGGGCG

1081 TCTTCACGCT CTGCTGGCTG CCCTTCTTCC TGGCCAACGT

1121 GGTGAAGGCC TTCCACCGCG AGCTGGTGCC CGACCGCCTC

1161 TTCGTCTTCT TCAACTGGCT GGGCTACGCC AACTCGGCCT

1201 TCAACCCCAT CATCTACTGC CGCAGCCCCG ACTTCCGCAA

1241 GGCCTTCCAG GGACTGCTCT GCTGCGCGCG CAGGGCTGCC

1281 CGCCGGCGCC ACGCGACCCA CGGAGACCGG CCGCGCGCCT

1321 CGGGCTGTCT GGCCCGGCCC GGACCCCCGC CATCGCCCGG

1361 GGCCGCCTCG GACGACGACG ACGACGATGT CGTCGGGGCC

1401 ACGCCGCCCG CGCGCCTGCT GGAGCCCTGG GCCGGCTGCA

1441 ACGGCGGGGC GGCGGCGGAC AGCGACTCGA GCCTGGACGA

1481 GCCGTGCCGC CCCGGCTTCG CCTCGGAATC CAAGGTGTAG

1521 GGCCCGGCGC GGGGCGCGGA CTCCGGGCAC GGCTTCCCAG

1561 GGGAACGAGG AGATCTGTGT TTACTTAAGA CCGATAGCAG

1601 GTGAACTCGA AGCCCACAAT CCTCGTCTGA ATCATCCGAG

-continued

```
1641 GCAAAGAGAA AAGCCACGGA CCGTTGCACA AAAAGGAAAG
1681 TTTGGGAAGG GATGGGAGAG TGGCTTGCTG ATGTTCCTTG
1721 TTGTTTTTTT TTTCTTTTCT TTTCTTTCTT CTTCTTTTTT
1741 TTTTTTTTTT TTTTTTCTGT TTGTGGTCCG GCCTTCTTTT
1801 GTGTGTGCGT GTGATGCATC TTTAGATTTT TTTCCCCCAC
1841 CAGGTGGTTT TTGACACTCT CTGAGAGGAC CGGAGTGGAA
1881 GATGGGTGGG TTAGGGGAAG GGAGAAGCAT TAGGAGGGGA
1921 TTAAAATCGA TCATCGTGGC TCCCATCCCT TTCCCGGGAA
1961 CAGGAACACA CTACCAGCCA GAGAGAGGAG AATGACAGTT
2001 TGTCAAGACA TATTTCCTTT TGCTTTCCAG ACAAATTTCA
2041 TTTTAATTTC TAAGTAATGA TTTCTGCTGT TATGAAAGCA
2081 AAGAGAAAGG ATGGAGGCAA AATAAAAAAA AATCACGTTT
2121 CAAGAAATGT TAAGCTCTTC TTGGAACAAG CCCCACCTTG
2161 CTTTCCTTGT GTAGGGCAAA CCCGCTGTCC CCCGCGCGCC
2201 TGGGTGGTCA GGCTGAGGGA TTTCTACCTC ACACTGTGCA
2241 TTTGCACAGC AGATAGAAAG ACTTGTTTAT ATTAAACAGC
2281 TTATTTATGT ATCAATATTA GTTGGAAGGA CCAGGCGCAG
2321 AGCCTCTCTC TGTGACATGT GACTCTGTCA ATTGAAGACA
2361 GGACATTAAA AGAGAGCGAG AGAGAGAAAC AGTTCAGATT
2401 ACTGCACATG TGGATAAAAA CAAAAACAAA AAAAAGGAGT
2441 GGTTCAAAAT GCCATTTTTG CACAGTGTTA GGAATTACAA
2481 AATCCACAGA AGATGTTACT TGCACAAAAA GAAATTAAAT
2521 ATTTTTTAAA GGGAGAGGGG CTGGGCAGAT CTTAAATAAA
2561 ATTCAAACTC TACTTCTGTT GTCTAGTATG TTATTGAGCT
2601 AATGATTCAT TGGGAAAATA CCTTTTTATA CTCCTTTATC
2641 ATGGTACTGT AACTGTATCG ATATTATAAA TATAATTATC
2681 TTAAGGATTT TTTATTTTTT TTTATGTCCA AGTGCCCACG
2721 TGAATTTGCT GGTGAAAGTT AGCACTTGTG TGTAAATTCT
2761 ACTTCCTCTT GTGTGTTTTA CCAAGTATTT ATACTCTGGT
2801 GCAACTAACT ACTGTGTGAG GAATTGGTCC ATGTGCAATA
2841 AATACCAATG AAGCACAATC AA
```

The rs1801252 single nucleotide polymorphism (SNP) is present in the ADRB1 gene, where the variable nucleotide at about position 231 (underlined) can be adenine in some individuals and guanine in others. The rs1801252 sequence (SEQ ID NO:2) is shown below, where the underlined A/G is the SNP.

```
CTCGTTGCTGCCTCCCGCCAGCGAA[A/G]GCCCCGAGCCGCTGTCTCA
GCAGTG.
```

The rs1801253 single nucleotide polymorphism (SNP) is also present in the ADRB1 gene, where the variable nucleotide at about position 1251 (underlined) can be guanine in some individuals and cytosine in others. The rs1801253 sequence (SEQ ID NO:3) is shown below, where the underlined C/G is the SNP.

```
CCCCGACTTCCGCAAGGCCTTCCAG[C/G]GACTGCTCTGCTGCGCGCG
CAGGGC.
```

The $\beta_1$AR polypeptide encoded by the ADRB1 cDNA with SEQ ID NO:1 has the following sequence (SEQ ID NO:4).

```
  1 MGAGVLVLGA SEPGNLSSAA PLPDGAATAA RLLVPASPPA
 41 SLLPPASESP EPLSQQWTAG MGLLMALIVL LIVAGNVLVI
 81 VAIAKTPRLQ TLTNLFIMSL ASADLVMGLL VVPFGATIVV
121 WGRWEYGSFF CELWTSVDVL CVTASIETLC VIALDRYLAI
161 TSPFRYQSLL TRARARGLVC TVWAISALVS FLPILMHWWR
201 AESDEARRCY NDPKCCDFVT NRAYAIASSV VSFYVPLCIM
241 AFVYLRVFRE AQKQVKKIDS CERRFLGGPA RPPSPSPSPV
281 PAPAPPPGPP RPAAAAATAP LANGRAGKRR PSRLVALREQ
321 KALKTLGIIM GVFTLCWLPF FLANVVKAFH RELVPDRLFV
361 FFNWLGYANS AFNPIIYCRS PDFRKAFQGL LCCARRAARR
401 RHATHGDRPR ASGCLARPGP PPSPGAASDD DDDDVVGATP
441 PARLLEPWAG CNGGAAADSD SSLDERCRPG FASESKV
```

Note that the underlined amino acid at position 49 is serine because some individuals have SEQ ID NO:1 or 2, where the variable nucleotide at about position 231 of SEQ ID NO:1 is adenine. However, position 49 of SEQ ID NO:4 can be glycine in some individuals because those individual have guanine at nucleotide position 231 in SEQ ID NO:1.

Note also that the glycine at position 389 is an arginine (instead of glycine) as shown for SEQ ID NO:4 when position 1251 of SEQ ID NO:1 is a cytosine.

Individuals with serine at $\beta_1$AR amino acid position 49 and/or arginine at position 389 are more responsive to beta-blockers than those with glycines at these positions. Hence, for example, an individual who expresses the $\beta_1$AR polypeptide with SEQ ID NO:4, will be more responsive to beta-blockers than an individual who expresses the $\beta_1$AR polypeptide with glycines at both positions 49 and 389.

A full length human ADRB2 cDNA nucleotide sequence is available from the database maintained by the National Center for Biotechnology Information (see website at ncbi.nlm.nih.gov), which has accession number NM_000024 (GI:283483994), and is shown below as SEQ ID NO:5.

```
  1 GCACATAACG GGCAGAACGC ACTGCGAAGC GGCTTCTTCA
 41 GAGCACGGGC TGGAACTGGC AGGCACCGCG AGCCCCTAGC
 81 ACCCGACAAG CTGAGTGTGC AGGACGAGTC CCCACCACAC
121 CCACACCACA GCCGCTGAAT GAGGCTTCCA GGCGTCCGCT
161 CGCCGGCCGC AGAGCCCCGC CGTGGGTCCG CCCGCTGAGG
201 CGCCCCCAGC CAGTGCGCTC ACCTGCCAGA CTGCGCGCCA
```

-continued

```
 241 TGGGGCAACC CGGGAACGGC AGCGCCTTCT TGCTGGCACC
 281 CAATAGAAGC CATGCCCCGG ACCACGACGT CACGCAGCAA
 321 AGGGACGAGG TGTGGGTGGT GGGCATGGGC ATCGTCATGT
 361 CTCTCATCGT CCTGGCCATC GTGTTTGGCA ATGTGCTGGT
 401 CATCACAGCC ATTGCCAAGT TCGAGCGTCT GCAGACGGTC
 441 ACCAACTACT TCATCACTTC ACTGGCCTGT GCTGATCTGG
 481 TCATGGGCCT GGCAGTGGTG CCCTTTGGGG CCGCCCATAT
 521 TCTTATGAAA ATGTGGACTT TTGGCAACTT CTGGTGCGAG
 561 TTTTGGACTT CCATTGATGT GCTGTGCGTC ACGGCCAGCA
 601 TTGAGACCCT GTGCGTGATC GCAGTGGATC GCTACTTTGC
 641 CATTACTTCA CCTTTCAAGT ACCAGAGCCT GCTGACCAAG
 681 AATAAGGCCC GGGTGATCAT TCTGATGGTG TGGATTGTGT
 721 CAGGCCTTAC CTCCTTCTTG CCCATTCAGA TGCACTGGTA
 761 CCGGGCCACC CACCAGGAAG CCATCAACTG CTATGCCAAT
 801 GAGACCTGCT GTGACTTCTT CACGAACCAA GCCTATGCCA
 841 TTGCCTCTTC CATCGTGTCC TTCTACGTTC CCCTGGTGAT
 881 CATGGTCTTC GTCTACTCCA GGGTCTTTCA GGAGGCCAAA
 921 AGGCAGCTCC AGAAGATTGA CAAATCTGAG GGCCGCTTCC
 961 ATGTCCAGAA CCTTAGCCAG GTGGAGCAGG ATGGGCGGAC
1001 GGGGCATGGA CTCCGCAGAT CTTCCAAGTT CTGCTTGAAG
1041 GAGCACAAAG CCCTCAAGAC GTTAGGCATC ATCATGGGCA
1081 CTTTCACCCT CTGCTGGCTG CCCTTCTTCA TCGTTAACAT
1121 TGTGCATGTG ATCCAGGATA ACCTCATCCG TAAGGAAGTT
1161 TACATCCTCC TAAATTGGAT AGGCTATGTC AATTCTGGTT
1201 TCAATCCCCT TATCTACTGC CGGAGCCCAG ATTTCAGGAT
1241 TGCCTTCCAG GAGCTTCTGT GCCTGCGCAG GTCTTCTTTG
1281 AAGGCCTATG GGAATGGCTA CTCCAGCAAC GGCAACACAG
1321 GGGAGCAGAG TGGATATCAC GTGGAACAGG AGAAAGAAAA
1361 TAAACTGCTG TGTGAAGACC TCCCAGGCAC GGAAGACTTT
1401 GTGGGCCATC AAGGTACTGT GCCTAGCGAT AACATTGATT
1441 CACAAGGGAG GAATTGTAGT ACAAATGACT CACTGCTGTA
1481 AAGCAGTTTT TCTACTTTTA AAGACCCCCC CCCCCAACAG
1521 AACACTAAAC AGACTATTTA ACTTGAGGGT AATAAACTTA
1561 GAATAAAATT GTAAAATTGT ATAGAGATAT GCAGAAGGAA
1601 GGGCATCCTT CTGCCTTTTT TATTTTTTTA AGCTGTAAAA
1641 AGAGAGAAAA CTTATTTGAG TGATTATTTG TTATTTGTAC
1681 AGTTCAGTTC CTCTTTGCAT GGAATTTGTA AGTTTATGTC
1721 TAAAGAGCTT TAGTCCTAGA GGACCTGAGT CTGCTATATT
1761 TTCATGACTT TTCCATGTAT CTACCTCACT ATTCAAGTAT
1801 TAGGGGTAAT ATATTGCTGC TGGTAATTTG TATCTGAAGG
1841 AGATTTTCCT TCCTACACCC TTGGACTTGA GGATTTTGAG
```

-continued

```
1881 TATCTCGGAC CTTTCAGCTG TGAACATGGA CTCTTCCCCC
1921 ACTCCTCTTA TTTGCTCACA CGGGGTATTT TAGGCAGGGA
1961 TTTGAGGAGC AGCTTCAGTT GTTTTCCCGA GCAAAGTCTA
2001 AAGTTTACAG TAAATAAATT GTTTGACCAT GCCTTCATTG
2041 CAAAAAAAAA AAAAAAAA
```

The rs1042713 single nucleotide polymorphism (SNP) is present in the ADRB2 gene, where the variable nucleotide at about position 285 (underlined) can be in adenine some individuals and guanine in others. The rs1042713 sequence (SEQ ID NO:6) is shown below, where the underlined A/G is the SNP.

CAGCGCCTTCTTGCTGGCACCCAAT[A/G]GAAGCCATGCGCCGGACCA CGACGT.

The rs1042714 single nucleotide polymorphism (SNP) is also present in the ADRB2 gene, where the variable nucleotide at about position 318 (underlined) can be cytosine in some individuals and guanine in others. The rs1042714 sequence (SEQ ID NO:7) is shown below, where the underlined C/G is the SNP.

TGCGCCGGACCACGACGTCACGCAG[C/G]AAAGGGACGAGGTGTGGGT GGTGGG.

The $\beta_2$AR polypeptide encoded by the ADRB2 cDNA with SEQ ID NO:5 has the following sequence (SEQ ID NO:8).

```
  1 MGQPGNGSAF LLAPNRSHAP DHDVTQQRDE VWVVGMGIVM
 41 SLIVLAIVFG NVLVITAIAK FERLQTVTNY FITSLACADL
 81 VMGLAVVPFG AAHILMKMWT FGNFWCEFWT SIDVLCVTAS
121 IETLCVIAVD RYFAITSPFK YQSLLTKNKA RVIILMVWIV
161 SGLTSFLPIQ MHWYRATHQE AINCYANETC CDFFTNQAYA
201 IASSIVSFYV PLVIMVFVYS RVFQEAKRQL QKIDKSEGRF
241 HVQNLSQVEQ DGRTGHGLRR SSKFCLKEHK ALKTLGIIMG
281 TFTLCWLPFF IVNIVHVIQD NLIRKEVYIL LNWIGYVNSG
321 FNPLIYCRSP DFRIAFQELL CLRRSSLKAY GNGYSSNGNT
361 GEQSGYHVEQ EKENKLLCED LPGTEDFVGH QGTVPSDNID
401 SQGRNCSTND SLL
```

Note that the underlined arginine at position 16 of SEQ ID NO:8 is arginine because some individuals have nucleotide sequence SEQ ID NO:5, where the nucleotide at about position 285 is adenine. However, position 16 of SEQ ID NO:8 can be glycine in some individuals because those individuals have guanine at nucleotide position 285 in SEQ ID NO:5.

Note also that the glutamine at position 27 of SEQ ID NO:8 is a glutamic acid when position 318 of nucleotide sequence SEQ ID NO:5 is a guanine.

Individuals with glycine at position 16 and/or glutamic acid at $\beta_2$AR position 27 are more responsive to beta-blockers than those with arginine and glutamine, respectively, at these positions. Hence, for example, an individual who expresses the $\beta_2$AR polypeptide with SEQ ID NO:5, will be more responsive to beta-blockers than an individual who expresses the $\beta_2$AR polypeptide with arginine and glutamine at positions 16 and 27.

The gene that encodes cytochromme P450 2D6 (CYP2D6) has been shown to alter the metabolism of the drugs in the beta-blocker class. This alteration in drug metabolism can alter the amount of bioavailable drug. Poor drug metabolizers tend to have more drugs available in the body for longer and will, therefore, have a greater response to therapy. In contrast, active metabolizers of a drug will have less of the drug available in their system and will respond poorly to therapy.

Because of the importance of CYP2D6 on beta-blocker metabolism, this gene is a useful marker of responsive to beta-blocker therapy.

A full length human CYP2D6 cDNA nucleotide sequence is available from the database maintained by the National Center for Biotechnology Information (see website at ncbi.nlm.nih.gov), which has accession number NM_000106.5 (GI:392513720), and is shown below as SEQ ID NO:9.

```
   1 GTGCTGAGAG TGTCCTGCCT GGTCCTCTGT GCCTGGTGGG
  41 GTGGGGGTGC CAGGTGTGTC CAGAGGAGCC CATTTGGTAG
  81 TGAGGCAGGT ATGGGGCTAG AAGCACTGGT GCCCCTGGCC
 121 GTGATAGTGG CCATCTTCCT GCTCCTGGTG GACCTGATGC
 161 ACCGGCGCCA ACGCTGGGCT GCACGCTACC CACCAGGCCC
 201 CCTGCCACTG CCCGGGCTGG GCAACCTGCT GCATGTGGAC
 241 TTCCAGAACA CACCATACTG CTTCGACCAG TTGCGGCGCC
 281 GCTTCGGGGA CGTGTTCAGC CTGCAGCTGG CCTGGACGCC
 321 GGTGGTCGTG CTCAATGGGC TGGCGGCCGT GCGCGAGGCG
 361 CTGGTGACCC ACGGCGAGGA CACCGCCGAC CGCCCGCCTG
 401 TGCCCATCAC CCAGATCCTG GGTTTCGGGC CGCGTTCCCA
 441 AGGGGTGTTC CTGGCGCGCT ATGGGCCCGC GTGGCGCGAG
 481 CAGAGGCGCT TCTCCGTGTC CACCTTGCGC AACTTGGGCC
 521 TGGGCAAGAA GTCGCTGGAG CAGTGGGTGA CCGAGGAGGC
 561 CGCCTGCCTT TGTGCCGCCT TCGCCAACCA CTCCGGACGC
 601 CCCTTTCGCC CCAACGGTCT CTTGGACAAA GCCGTGAGCA
 641 ACGTGATCGC CTCCCTCACC TGCGGGCGCC GCTTCGAGTA
 681 CGACGACCCT CGCTTCCTCA GGCTGCTGGA CCTAGCTCAG
 721 GAGGGACTGA AGGAGGAGTC GGGCTTTCTG CGCGAGGTGC
 761 TGAATGCTGT CCCCGTCCTC CTGCATATCC CAGCGCTGGC
 801 TGGCAAGGTC CTACGCTTCC AAAAGGCTTT CCTGACCCAG
 841 CTGGATGAGC TGCTAACTGA GCACAGGATG ACCTGGGACC
 881 CAGCCCAGCC CCCCCGAGAC CTGACTGAGG CCTTCCTGGC
 921 AGAGATGGAG AAGGCCAAGG GGAACCCTGA GAGCAGCTTC
 961 AATGATGAGA ACCTGCGCAT AGTGGTGGCT GACCTGTTCT
```

-continued

```
1001 CTGCCGGGAT GGTGACCACC TCGACCACGC TGGCCTGGGG
1041 CCTCCTGCTC ATGATCCTAC ATCCGGATGT GCAGCGCCGT
1081 GTCCAACAGG AGATCGACGA CGTGATAGGG CAGGTGCGGC
1121 GACCAGAGAT GGGTGACCAG GCTCACATGC CCTACACCAC
1161 TGCCGTGATT CATGAGGTGC AGCGCTTTGG GGACATCGTC
1201 CCCCTGGGTG TGACCCATAT GACATCCCGT GACATCGAAG
1241 TACAGGGCTT CCGCATCCCT AAGGGAACGA CACTCATCAC
1281 CAACCTGTCA TCGGTGCTGA AGGATGAGGC CGTCTGGGAG
1321 AAGCCCTTCC GCTTCCACCC CGAACACTTC CTGGATGCCC
1361 AGGGCCACTT TGTGAAGCCG GAGGCCTTCC TGCCTTTCTC
1401 AGCAGGCCGC CGTGCATGCC TCGGGGAGCC CCTGGCCCGC
1441 ATGGAGCTCT TCCTCTTCTT CACCTCCCTG CTGCAGCACT
1481 TCAGCTTCTC GGTGCCCACT GGACAGCCCC GGCCCAGCCA
1521 CCATGGTGTC TTTGCTTTCC TGGTGAGCCC ATCCCCCTAT
1561 GAGCTTTGTG CTGTGCCCCG CTAGAATGGG GTACCTAGTC
1601 CCCAGCCTGC TCCCTAGCCA GAGGCTCTAA TGTACAATAA
1641 AGCAATGTGG TAGTTCCAAA AAAAAAAAAA AAA
```

The rs3892097 single nucleotide polymorphism (SNP) is present in the CYP2D6 gene, where the variable nucleotide at a splice site at about position 595 in SEQ ID NO:9 (underlined), which can be in adenine some individuals and guanine in others.

The rs3892097 sequence (SEQ ID NO: 10) of the CYP2D6 gene is shown below, where the underlined A/G is the SNP.

CCCTTACCCGCATCTCCCACCCCCA[A/G]GACGCCCCTTTCGCCCCAA CGGTCT.

Because the SNP occurs near a splice site, the sequences to the left of the SNP site in SEQ ID NO:10 do not appear in the SEQ ID NO:9 nucleotide CYP2D6 cDNA sequence.

The cytochrome P450 2D6 polypeptide encoded by the CYP2D6 cDNA with SEQ ID NO:9 has the following sequence (SEQ ID NO: 11).

```
  1 MGLEALVPLA VIVAIFLLLV DLMHRRQRWA ARYPPGPLPL
 41 PGLGNLLHVD FQNTPYCFDQ LRRRFGDVFS LQLAWTPVVV
 81 LNGLAAVREA LVTHGEDTAD RPPVPITQIL GFGPRSQGVF
121 LARYGPAWRE QRRFSVSTLR NLGLGKKSLE QWVTEEAACL
161 CAAFANHSGR PFRPNGLLDK AVSNVIASLT CGRRFEYDDP
201 RFLRLLDLAQ EGLKEESGFL REVLNAVPVL LHIPALAGKV
241 LRFQKAFLTQ LDELLTEHRM TWDPAQPPRD LTEAFLAEME
281 KAKGNPESSF NDENLRIVVA DLFSAGMVTT STTLAWGLLL
321 MILHPDVQRR VQQEIDDVIG QVRRPEMGDQ AHMPYTTAVI
361 HEVQRFGDIV PLGVTHMTSR DIEVQGFRIP KGTTLITNLS
401 SVLKDEAVWE KPFRFHPEHF LDAQGHFVKP EAFLPFSAGR
```

-continued

```
441 RACLGEPLAR MELFLFFTSL LQHFSFSVPT GQPRPSHHGV

481 FAFLVSPSPY ELCAVPR
```

Note that the underlined glycine at position 169 of SEQ ID NO:11 is glycine because some individuals have nucleotide sequence SEQ ID NO:9, where the nucleotide at about position 595 is guanine. However, position 169 of SEQ ID NO: 11 can be arginine in some individuals because those individuals have adenine at nucleotide position 295 in SEQ ID NO:9.

A patient with that is homozygous for adenine (AA) at the rs3892097 variable site will express CYP2D6 with arginine at position 169 and will not metabolize metoprolol and propranolol as quickly as those with guanine (glycine). Hence, homozygous individuals with adenine (AA) at the rs3892097 variable site have higher plasma levels of metoprolol and propranolol after taking these drugs than subjects that are not homozygous for adenine (AA) at the rs3892097 variable site. Homozygous individuals with adenine (AA) at the rs3892097 variable site would respond more normally to atenolol and carvedilol, which do not require CYP2D6 for their metabolism.

Vasodilation Therapy

Dilation of blood vessels results in decreases in blood pressure, whereas constriction of blood vessels results in increases in blood pressure. The blood vessels are controlled through local neural signaling that is largely under parasympathetic control, and circulating hormones that are largely under sympathetic control, as well as other circulating proteins. Blood pressure increases following stimulation of the angiotensin receptors, which results in vasoconstriction. Angiotensin receptors are stimulated by angiotensin II, which is converted from angiotensin I through the angiotensin converting enzyme (ACE). Angiotensin II is a potent vasoconstrictor and actively inhibits bradykinin, which is a potent vasodilator.

Therefore, angiotensin converting enzyme is a common target of blood pressure therapy. ACE inhibitors such as lisinopril promote vasodilation which, ultimately, reduces the bioavailability of angiotensin-II. Similarly, angiotensin II receptor antagonists such as losartan act as competitive inhibitors, which decrease the number of receptors that are available to bind to angiotensin-II. Despite the method used for promoting vasodilation (through reductions in ACE or receptor inhibition) the end result, on average in the population, is vasodilation which results in a drop in blood pressure due to the inverse relationship between the size of the vessel and the pressure exerted on the vessel, all else being equal. Despite this benefit there is a "bell-curve" response to these therapies in humans. Not all individuals are responsive to vasodilator therapy.

Several functional polymorphisms of the genes that encode for ACE and angiotensin-II receptors exist, which can affect how a subject responds to vasodilation.

Examples of functional ACE polymorphisms include the insertion or deletion polymorphisms such as a 287 base pair fragment (Ulgen et al., *Coron Artery Dis* 18:153-157 (2007)). The rs1799752 polymorphism is an insertion/deletion in an intron of the ACE gene, and with the sequence (SEQ ID NO:12) shown below, where sequences in the bracket are the insertion/deletion.

```
TCCCATTTCTCTAGACCTGCTGCCT[-/ATACAGTCACTTTTTTTTTTT

TTTTGAGACGGAGTCTCGCTCTGTCGCCC]ATACAGTCACTTTTATGTG

GTTTCG.
```

The deletion removes the bracketed nucleic acid segment so that the rs1799752 polymorphism will have the following sequence (SEQ ID NO:35).

```
TCCCATTTCTCTAGACCTGCTGCCTATACAGTCACTTTTATGTGGTTT

CG.
```

Research indicates that such an ACE deletion polymorphism results in higher ACE plasma levels and greater reduction in ejection fraction in patients following myocardial infraction (likely from elevations in blood pressure) (McNamara et al., *J Am Coll Cardiol* 44:2019-2026 (2004): Pilati et al., *Congest Heart Fail* 10:87-93 (2004). In addition, patients with the deletion polymorphism are more likely to have left-ventricular hypertrophy when compared to patients with the insertion polymorphism (left-ventricular hypertrophy results secondary to prolonged exposure to high blood pressure). Subjects with the deletion polymorphism would therefore be most responsive to ACE-inhibition or angiotensin-II receptor inhibition.

At least one functional variant of angiotensin has been found in humans: a cytosine to threonine substitution at nucleotide 4072 (Pilbrow et al., *Hypertension* 49:322-327 (2007); Tang et al., *Am Heart J* 143:854-860 (2002)). Human angiotensinogen is expressed from the AGT gene. A cDNA nucleotide sequence for human angiotensinogen is provided below as SEQ ID NO:13 (accession number NM_000029.3 GI:188595658, from the NCBI database).

```
  1 ATCCCATGAG CGGGCAGCAG GGTCAGAAGT GGCCCCCGTG

 41 TTGCCTAAGC AAGACTCTCC CCTGCCCTCT GCCCTCTGCA

 81 CCTCCGGCCT GCATGTCCCT GTGGCCTCTT GGGGGTACAT

121 CTCCCGGGGC TGGGTCAGAA GGCCTGGGTG GTTGGCCTCA

161 GGCTGTCACA CACCTAGGGA GATGCTCCCG TTTCTGGGAA

201 CCTTGGCCCC GACTCCTGCA AACTTCGGTA AATGTGTAAC

241 TCGACCCTGC ACCGGCTCAC TCTGTTCAGC AGTGAAACTC

281 TGCATCGATC ACTAAGACTT CCTGGAAGAG GTCCCAGCGT

321 GAGTGTCGCT TCTGGCATCT GTCCTTCTGG CCAGCCTGTG

361 GTCTGGCCAA GTGATGTAAC CCTCCTCTCC AGCCTGTGCA

401 CAGGCAGCCT GGGAACAGCT CCATCCCCAC CCCTCAGCTA

441 TAAATAGGGC ATCGTGACCC GGCCGGGGGA AGAAGCTGCC

481 GTTGTTCTGG GTACTACAGC AGAAGGGTAT GCGGAAGCGA

521 GCACCCCAGT CTGAGATGGC TCCTGCCGGT GTGAGCCTGA

561 GGGCCACCAT CCTCTGCCTC CTGGCCTGGG CTGGCCTGGC

601 TGCAGGTGAC CGGGTGTACA TACACCCCTT CCACCTCGTC

641 ATCCACAATG AGAGTACCTG TGAGCAGCTG GCAAAGGCCA

681 ATGCCGGGAA GCCCAAAGAC CCCACCTTCA TACCTGCTCC
```

-continued

```
 721 AATTCAGGCC AAGACATCCC CTGTGGATGA AAAGGCCCTA
 761 CAGGACCAGC TGGTGCTAGT CGCTGCAAAA CTTGACACCG
 801 AAGACAAGTT GAGGGCCGCA ATGGTCGGGA TGCTGGCCAA
 841 CTTCTTGGGC TTCCGTATAT ATGGCATGCA CAGTGAGCTA
 881 TGGGGCGTGG TCCATGGGGC CACCGTCCTC TCCCCAACGG
 921 CTGTCTTTGG CACCCTGGCC TCTCTCTATC TGGGAGCCTT
 961 GGACCACACA GCTGACAGGC TACAGGCAAT CCTGGGTGTT
1001 CCTTGGAAGG ACAAGAACTG CACCTCCCGG CTGGATGCGC
1041 ACAAGGTCCT GTCTGCCCTG CAGGCTGTAC AGGGCCTGCT
1081 AGTGGCCCAG GGCAGGGCTG ATAGCCAGGC CCAGCTGCTG
1121 CTGTCCACGG TGGTGGGCGT GTTCACAGCC CCAGGCCTGC
1161 ACCTGAAGCA GCCGTTTGTG CAGGGCCTGG CTCTCTATAC
1201 CCCTGTGGTC CTCCCACGCT CTCTGGACTT CACAGAACTG
1241 GATGTTGCTG CTGAGAAGAT TGACAGGTTC ATGCAGGCTG
1281 TGACAGGATG GAAGACTGGC TGCTCCCTGA TGGGAGCCAG
1321 TGTGGACAGC ACCCTGGCTT TCAACACCTA CGTCCACTTC
1361 CAAGGGAAGA TGAAGGGCTT CTCCCTGCTG GCCGAGCCCC
1401 AGGAGTTCTG GGTGGACAAC AGCACCTCAG TGTCTGTTCC
1441 CATGCTCTCT GGCATGGGCA CCTTCCAGCA CTGGAGTGAC
1481 ATCCAGGACA ACTTCTCGGT GACTCAAGTG CCCTTCACTG
1521 AGAGCGCCTG CCTGCTGCTG ATCCAGCCTC ACTATGCCTC
1561 TGACCTGGAC AAGGTGGAGG GTCTCACTTT CCAGCAAAAC
1601 TCCCTCAACT GGATGAAGAA ACTATCTCCC CGGACCATCC
1641 ACCTGACCAT GCCCCAACTG GTGCTGCAAG GATCTTATGA
1681 CCTGCAGGAC CTGCTCGCCC AGGCTGAGCT GCCCGCCATT
1721 CTGCACACCG AGCTGAACCT GCAAAAATTG AGCAATGACC
1761 GCATCAGGGT GGGGGAGGTG CTGAACAGCA TTTTTTTTGA
1801 GCTTGAAGCG GATGAGAGAG AGCCCACAGA GTCTACCCAA
1841 CAGCTTAACA AGCCTGAGGT CTTGGAGGTG ACCCTGAACC
1881 GCCCATTCCT GTTTGCTGTG TATGATCAAA GCGCCACTGC
1921 CCTGCACTTC CTGGGCCGCG TGGCCAACCC GCTGAGCACA
1961 GCATGAGGCC AGGGCCCCAG AACACAGTGC CTGGCAAGGC
2001 CTCTGCCCCT GGCCTTTGAG GCAAAGGCCA GCAGCAGATA
2041 ACAACCCCGG ACAAATCAGC GATGTGTCAC CCCCAGTCTC
2081 CCACCTTTTC TTCTAATGAG TCGACTTTCA GCTGGAAAGC
2121 AGCCGTTTCT CCTTGGTCTA AGTGTGCTGC ATGGAGTGAG
2161 CAGTAGAAGC CTGCAGCGGC ACAAATGCAC CTCCCAGTTT
2201 GCTGGGTTTA TTTTAGAGAA TGGGGGTGGG GAGGCAAGAA
2241 CCAGTGTTTA GCGCGGGACT ACTGTTCCAA AAAGAATTCC
2281 AACCGACCAG CTTGTTTGTG AAACAAAAAA GTGTTCCCTT
2321 TTCAAGTTGA GAACAAAAAT TGGGTTTTAA AATTAAAGTA
```

-continued

```
2361 TACATTTTTG CATTGCCTTC GGTTTGTATT TAGTGTCTTG
2401 AATGTAAGAA CATGACCTCC GTGTAGTGTC TGTAATACCT
2441 TAGTTTTTTC CACAGATGCT TGTGATTTTT GAACAATACG
2481 TGAAAGATGC AAGCACCTGA ATTTCTGTTT GAATGCGGAA
2521 CCATAGCTGG TTATTTCTCC CTTGTGTTAG TAATAAACGT
2561 CTTGCCACAA TAAGCCTCCA
2581 AAAAAAA
```

The rs699 single nucleotide polymorphism (SNP) is present in the AGT gene, where the variable nucleotide is at about position 1311 in SEQ ID NO:13 (underlined), which can be in thymine some individuals and cytosine in others. The rs699 sequence (SEQ ID NO:14) is shown below, where the underlined C/T is the SNP.

```
GGATGGAAGACTGGCTGCTCCCTGA[C/T]GGGAGCCAGTGTGGACAGC
ACCCTG.
```

The human angiotensinogen polypeptide encoded by the AGT cDNA with SEQ ID NO:13 has the following sequence (SEQ ID NO:15).

```
  1 MRKRAPQSEM APAGVSLRAT ILCLLAWAGL AAGDRVYIHP
 41 FHLVIHNEST CEQLAKANAG KPKDPTFIPA PIQAKTSPVD
 81 EKALQDQLVL VAAKLDTEDK LRAAMVGMLA NFLGFRIYGM
121 HSELWGVVHG ATVLSPTAVF GTLASLYLGA LDHTADRLQA
161 ILGVPWKDKN CTSRLDAHKV LSALQAVQGL LVAQGRADSQ
201 AQLLLSTVVG VFTAPGLHLK QPFVQGLALY TPVVLPRSLD
241 FTELDVAAEK IDRFMQAVTG WKTGCSLMGA SVDSTLAFNT
281 YVHFQGKMKG FSLLAFPQEF WVDNSTSVSV PMLSGMGTFQ
321 HWSDIQDNFS VTQVPFTESA CLLLIQPHYA SDLDKVEGLT
361 FQQNSLNWMK KLSPRTIHLT MPQLVLQGSY DLQDLLAQAE
401 LPAILHTELN LQKLSNDRIR VGEVLNSIFF ELEADEREPT
441 ESTQQLNKPE VLEVTLNRPF LFAVYDQSAT ALHFLGRVAN
481 PLSTA
```

Note that the underlined methionine at position 268 of SEQ ID NO: 15 is methionine because some individuals have nucleotide sequence SEQ ID NO: 13, where the nucleotide at about position 1311 is thymine. However, position 268 of SEQ ID NO:15 can be threonine in some individuals because those individuals have cytosine at nucleotide position 1311 in SEQ ID NO: 13.

The threonine polymorphism of angiotensin results in higher angiotensin levels and higher resting blood pressure values. Therefore, patients with the threonine genetic variant will benefit primarily from an ACE inhibitor (preventing the conversion of the higher levels of angiotensin I to angiotensin II) or an angiotensin receptor inhibitor.

An example of a functional polymorphism of an angiotensin II receptor type-1 involves an adenine to cytosine substitution at nucleotide 1166 (Miller et al. *Kidney Int* 56:2173-2180 (1999); Baudin, *Pharmacogenomics* 3:65-73

(2002)). Human angiotensin II receptor type-1 is expressed from the AGT1R gene. One example of an AGT1R single nucleotide polymorphism is the so-called A1166→C polymorphism, which is in the 3' untranslated region of the AGT1R gene. This A1166→C polymorphism is also identified as the rs5186 single nucleotide polymorphism (SNP), which has the following sequence (SEQ ID NO: 16) where the underlined A/C is the variable SNP site.

```
TGCAGCACTTCACTACCAAATGAGC[A/C]TTAGCTACTTTTCAGAATT

GAAGGA.
```

A portion of a 3' untranslated region of the AGT1R gene with NCBI accession number NG_008468.1 (GI: 198041751) is shown below (SEQ ID NO:17) that contains the rs5186 SNP with the variant nucleotide (adenine) identified below in bold and with underlining.

```
48961 ATTCAACTAG GCATCATACG TGACTGTAGA ATTGCAGATA
49001 TTGTGGACAC GGCCATGCCT ATCACCATTT GTATAGCTTA
49041 TTTTAACAAT TGCCTGAATC CTCTTTTTTA TGGCTTTCTG
49081 GGGAAAAAAT TTAAAAGATA TTTTCTCCAG CTTCTAAAAT
49121 ATATTCCCCC AAAAGCCAAA TCCCACTCAA ACCTTTCAAC
49181 AAAAATGAGC ACGCTTTCCT ACCGCCCCTC AGATAATGTA
49201 AGCTCATCCA CCAAGAAGCC TGCACCATGT TTTGAGGTTG
49241 AGTGACATGT TCGAAACCTG TCCATAAAGT AATTTTGTGA
49301 AAGAAGGAGC AAGAGAACAT TCCTCTGCAG CACTTCACTA
49321 CCAAATGAGC ATTAGCTACT TTTCAGAATT GAAGGAGAAA
49361 ATGCATTATG TGGACTGAAC CGACTTTTCT AAAGCTCTGA
49401 ACAAAAGCTT TTCTTTCCTT TTGCAACAAG ACAAAGCAAA
49441 GCCACATTTT GCATTAGACA GATGACGGCT GCTCGAAGAA
49481 CAATGTCAGA AACTCGATGA ATGTGTTGAT TTGAGAAATT
49521 TTACTGACAG AAATGCAATC TCCCTAGCCT GCTTTTGTCC
49561 TGTTATTTTT TATTTCCACA TAAAGGTATT TAGAATATAT
49601 TAAATCGTTA GAGGAGCAAC AGGAGATGAG AGTTCCAGAT
49641 TGTTCTGTCC AGTTTCCAAA GGGCAGTAAA GTTTTCGTGC
```

This polymorphism has been shown to influence resting blood pressure values which suggest which patients may benefit more from angiotensin-II receptor inhibition. Specifically, patients with the C variant of the angiotensin receptor type I tend to demonstrate higher resting blood pressure values, have more detrimental cardiovascular events, and have a greater chance of developing high blood pressure during pregnancy, when compared to the A variant. Subjects with the C variant will therefore be more responsive to angiotensin receptor blockers.

A cDNA sequence for human angiotensin II receptor is provided in the NCBI database as accession number X65699.1 (GI:510983), which has the following sequence (SEQ ID NO:18).

```
   1 GGCAGCAGCG AGTGACAGGA CGTCTGGACC GGCGCGCCGC
  41 TAGCAGCTCT GCCGGGCCGC GGCGCTGATC GATGGGAGCG
  81 GCTGGAGCGG ACCCAGCGAG TGAGGGCGCA CAGCCGGACG
 121 CCGAGGCGGC GGGCGGGAGA CCGCACCGCG ACGCCGGCCC
 161 TCGGCGGACG AGTCGAGCGC CCGGGCGCGG GTGTATTTGA
 201 TATAGTGTTT GCAACAAATT CGACCCAGGT GATCAAAATG
 241 ATTCTCAACT CTTCTACTGA AGATGGTATT AAAAGAATCC
 281 AAGATGATTG TCCCAAAGCT GGAAGGCATA ATTACATATT
 321 TGTCATGATT CCTACTTTAT ACAGTATCAT CTTTGTGGTG
 361 GGAATATTTG GAAACAGCTT GGTGGTGATA GTCATTTACT
 401 TTTATATGAA GCTGAAGACT GTGGCCAGTG TTTTTCTTTT
 441 GAATTTAGCA CTGGCTGACT TATGCTTTTT ACTGACTTTG
 481 CCACTATGGG CTGTCTACAC AGCTATGGAA TACCGCTGGC
 521 CCTTTGGCAA TTACCTATGT AAGATTGCTT CAGCCAGCGT
 561 CAGTTTCAAC CTGTACGCTA GTGTGTTTCT ACTCACGTGT
 601 CTCAGCATTG ATCGATACCT GGCTATTGTT CACCCAATGA
 641 AGTCCCGCCT TCGACGCACA ATGCTTGTAG CCAAAGTCAC
 681 CTGCATCATC ATTTGGCTGC TGGCAGGCTT GGCCAGTTTG
 721 CCAGCTATAA TCCATCGAAA TGTATTTTTC ATTGAGAACA
 761 CCAATATTAC AGTTTGTGCT TTCCATTATG AGTCCCAAAA
 801 TTCAACCCTC CCGATAGGGC TGGGCCTGAC CAAAAATATA
 841 CTGGGTTTCC TGTTTCCTTT TCTGATCATT CTTACAAGTT
 881 ATACTCTTAT TTGGAAGGCC CTAAAGAAGG CTTATGAAAT
 921 TCAGAAGAAC AAACCAAGAA ATGATGATAT TTTTAAGATA
 961 ATTATGGCAA TTGTGCTTTT CTTTTTCTTT TCCTGGATTC
1001 CCCACCAAAT ATTCACTTTT CTGGATGTAT TGATTCAACT
1041 AGGCATCATA CGTGACTGTA GAATTGCAGA TATTGTGGAC
1081 ACGGCCATGC CTATCACCAT TTGTATAGCT TATTTTAACA
1121 ATTGCCTGAA TCCTCTTTTT TATGGCTTTC TGGGGAAAAA
1161 ATTTAAAAGA TATTTTCTCC AGCTTCTAAA ATATATTCCC
1201 CCAAAAGCCA AATCCCACTC AAACCTTTCA ACAAAAATGA
1241 GCACGCTTTC CTACCGCCCC TCAGATAATG TAAGCTCATC
1281 CACCAAGAAG CCTGCACCAT GTTTTGAGGT TGAGTGACAT
1321 GTTCGAAACC TGTCCATAAA CTAATTTTGT GAAAGAAGGA
1361 GCAAGAGAAC ATTCCTCTGC AGCACTTCAC TACCAAATGA
1401 GCATTAGCTA CTTTTCAGAA TTGAAGGAGA AAATGCATTA
1441 TGTGCACTGA ACCGACTTTT CTAAAGCTCT GAACAAAAGC
1481 TTTTCTTTCC TTTTGCAACA AGACAAAGCA AAGCCACATT
1521 TTGCATTAGA CAGATGACGG CTGCTCGAAG AACAATGTCA
1561 GAAACTCGAT GAATGTGTTG ATTTGAGAAA TTTTACTGAC
1601 AGAAATGCAA TCTCCCTAGC CTGCTTTTGT CCTGTTATTT
```

-continued

```
1641 TTTATTTCCA CATAAAGGTA TTTAGAATAT ATTAACTCGT
1681 TAGAGGAGCA ACAGGAGATG AGAGTTCCAG ATTGTTCTGT
1721 CCAGTTTCCA AAGGGCAGTA AAGTTTTCGT GCCTGTTTTC
1761 AGCTATTAGC AACTGTGCCT ACACTTGCAC CTGGTCTGCA
1801 CATTTGTAC AAAGATATGC TTAAGCAGTA GTCGTCAAGT
1841 TGCAGATCTT TGTTGTGAAA TTCAACCTGT GTCTTATAGG
1881 TTTACACTGC CAAAACAATG CCCGTAAGAT GGCTTATTTG
1921 TATAATGGTG TTACCTAAAG TCACATATAA AAGTTAAACT
1961 ACTTGTAAAG CTGCTGCACT GGTCCCAAGT AGTAGTGTCT
2001 TCCTAGTATA TTAGTTTGAT TTAATATCTG AGAAGTGTAT
2041 ATAGTTTGTG GTAAAAAGAT TATATATCAT AAAGTATGCC
2081 TTCCTGTTTA AAAAAAGTAT ATATTCTACA CATATATGTA
2121 TATGTATATC TATATCTCTA AACTGCTGTT AATTGATTAA
2161 AATCTGGCAA AGTTATATTT ACCCC
```

In addition to angiotensin, angiotensin II receptors and ACE, renin has been shown to be a potent vasoconstrictor that can result in high blood pressure. Renin converts angiotensinogen to angiotensin I which can result in vasoconstriction due to the down-stream effects (angiotensin-I conversion to angiotensin II through ACE). One example of a functional and common renin polymorphism (Vangjeli et al., *Circulation Cardiovascular genetics* 3:53-59 (2010)) can influence the blood pressure response to vasodilator therapy. This renin polymorphism is present in rs12750834. The nucleotide sequence surrounding the renin rs12750834 single nucleotide polymorphism is shown below, where the underlined A/G in the sequence (SEQ ID NO:19) is the SNP.

AGAACACCAAAGCAGGCTTAATCTG[A/G]GGGCACTTACAGAGACTGC TTTAAA.

The complementary sequence of SEQ ID NO: 19 is the following sequence (SEQ ID NO:20).

TTTAAAGCAGTCTCTGTAAGTGCCC[C/T]CAGATTAAGCCTGCTTTGG TGTTCT.

Note that the cytosine to thymine substitution is a guanine to adenine substitution in the opposite strand.

The rs12750834 SNP contains a cytosine to thymine substitution, or a guanine to adenine substitution depending upon the DNA strand, at about nucleotide position 5312 upstream of the renin start site. The cytosine (guanine) variant of renin has been shown to correlate with greater reduction in blood pressure upon administration of angiotensin II receptor blockers such as valsartan.

Sodium/Diuretic Regulation of Blood Pressure

The kidneys are the center of long-term blood pressure regulation. Alterations in $Na^+$ reabsorption in the kidneys result in alterations in fluid retention, which leads to increases or decreases in blood plasma volume as well as to changes in the pressure against the vessels. There are several proteins that are important in renal $Na^+$ handling and in the response to diuretic therapy including the epithelial $Na^-$ channels, alpha-adducin, the $Na^+Cl^-$ co-transporter, and lysine deficient protein kinase-1 (WNK).

The epithelial sodium ($Na^+$) channel is responsible for $Na^+$ reabsorption on the apical portion of epithelial cells in the kidneys. The $Na^+$ channel is made up of three different subunits: the alpha, beta, and gamma. The alpha subunit of the epithelial $Na^+$ channel is highly functional and removal of this subunit abolishes channel activity in cell and animal models. The gamma subunit is also extremely important in channel function. Functional gamma genetic variants result in pseudohypoaldosteronism type-I and Liddle's syndrome, two severe genetic diseases resulting in salt wasting and high salt conservation (salt sensitivity), respectively. Adducin is made up of an alpha, beta, and gamma subunit. The alpha subunit increases sodium ($Na^+$) reabsorption in the kidneys through the activity of $Na^+K^+$ ATPase (which moves $Na^+$ and potassium into and out of cells). The sodium ($Na^+$) chloride ($Cl^-$) co-transporter is important in regulating $Na^+$ and $Cl^-$ movement between the kidney and the rest of the body. Active $Na^+$—$Cl^-$ transport results in $Na^+$ reabsorption and can, therefore, result in higher blood pressure. The WNK1 protein is a key regulator of long-term $Na^+$ and chloride $Cl^-$ reabsorption in the kidneys. WNK1 regulates the activity of $Na^+$—$Cl^-$ co-transporters. If a patient has a more active WNK1 genotype, they likely have greater $Na^+$ and $Cl^-$ reabsorption in the kidneys which can increase blood volume and, therefore, pressure on the vessels.

A functional and common polymorphism of the gene that encodes the epithelial $Na^+$ channel (SCNN1A) has been identified, where the polymorphism is an alanine to threonine substitution at about position 663-722. A cDNA sequence for the human SCNN1A gene is available from the NCBI database as accession number NM_001159576.1 (GI: 227430288). This sequence is provided below as SEQ ID NO:21.

```
  1 AAACAGAAGG CAGATAGAGA GGGAGTGAGA GGCAGGAGCT
 41 GAGACACAGA TCCTGGAGGA AGAAGACCAA AGGAAGGGGG
 81 CAGAGACAGA AAGGGAGGTG CTAGGACAAA ACTCGAAAGG
121 TGGCCCTATC AGGGAAGCAG AGGAGAGGCC GTTCTAGGGA
161 AGCCCAGCTC CGGCACTTTT GGCCCCAACT CCCGCAGGTC
201 TGCTGGCTCC AGGAAAGGTG GAGGAGGGAG GGAGGAGTGG
241 GAGAATGTGG GCGCAGGGTG GGACATGGGC ATGGCCAGGG
281 GCAGCCTCAC TCGGGTTCCA GGGGTGATGG GAGAGGGGAC
321 TCAGGGCCCA GAGCTCAGCC TTGACCCTGA CCCTTGCTCT
361 CCCCAATCCA CTCCGGGGCT CATGAAGGGG AACAAGCTGG
401 AGGAGCAGGA CCCTAGACCT CTGCAGCCCA TACCAGGTCT
441 CATGGAGGGG AACAAGCTGG AGGAGCAGGA CTCTAGCCCT
481 CCACAGTCCA CTCCAGGGCT CATGAAGGGG AACAAGCGTG
521 AGGAGCAGGG GCTGGGCCCC GAACCTGCGG CGCCCCAGCA
561 GCCCACGGCG GAGGAGGAGG CCCTGATCGA GTTCCACCGC
601 TCCTACCGAG AGCTCTTCGA GTTCTTCTGC AACAACACCA
641 CCATCCACGG CGCCATCCGC CTGGTGTGCT CCCAGCACAA
681 CCGCATGAAG ACGGCCTTCT GGGCAGTGCT GTGGCTCTGC
```

-continued

```
 721 ACCTTTGGCA TGATGTACTG GCAATTCGGC CTGCTTTTCG
 761 GAGAGTACTT CAGCTACCCC GTCAGCCTCA ACATCAACCT
 801 CAACTCGGAC AAGCTCGTCT TCCCCGCAGT GACCATCTGC
 841 ACCCTCAATC CCTACAGGTA CCCGGAAATT AAAGAGGAGC
 881 TGGAGGAGCT GGACCGCATC ACAGAGCAGA CGCTCTTTGA
 921 CCTGTACAAA TACAGCTCCT TCACCACTCT CGTGGCCGGC
 961 TCCCGCAGCC GTCGCGACCT GCGGGGGACT CTGCCGCACC
1001 CCTTGCAGCG CCTGAGGGTC CCGCCCCCGC CTCACGGGGC
1041 CCGTCGAGCC CGTAGCGTGG CCTCCAGCTT GCGGGACAAC
1081 AACCCCCAGG TGGACTGGAA GGACTGGAAG ATCGGCTTCC
1121 AGCTGTGCAA CCAGAACAAA TCGGACTGCT TCTACCAGAC
1161 ATACTCATCA GGGGTGGATG CGGTGAGGGA GTGGTACCGC
1201 TTCCACTACA TCAACATCCT GTCGAGGCTG CCAGAGACTC
1241 TGCCATCCCT GGAGGAGGAC ACGCTGGGCA ACTTCATCTT
1281 CGCCTGCCGC TTCAACCAGG TCTCCTGCAA CCAGGCGAAT
1321 TACTCTCACT TCCACCACCC GATGTATGGA AACTGCTATA
1361 CTTTCAATGA CAAGAACAAC TCCAACCTCT GGATGTCTTC
1401 CATGCCTGGA ATCAACAACG GTCTGTCCCT GATGCTGCGC
1441 GCAGAGCAGA ATGACTTCAT TCCCCTGCTG TCCACAGTGA
1481 CTGGGGCCCG GGTAATGGTG CACGGGCAGG ATGAACCTGC
1521 CTTTATGGAT GATGGTGGCT TTAACTTGCG GCCTGGCGTG
1561 GAGACCTCCA TCAGCATGAG GAAGGAAACC CTGGACAGAC
1601 TTGGGGGCGA TTATGGCGAC TGCACCAAGA ATGGCAGTGA
1641 TGTTCCTGTT GAGAACCTTT ACCCTTCAAA GTACACACAG
1681 CAGGTGTGTA TTCACTCCTG CTTCCAGGAG AGCATGATCA
1721 AGGAGTGTGG CTGTGCCTAC ATCTTCTATC CGCGGCCCCA
1761 GAACGTGGAG TACTGTGACT ACAGAAAGCA CAGTTCCTGG
1801 GGGTACTGCT ACTATAAGCT CCAGGTTGAC TTCTCCTCAG
1841 ACCACCTGGG CTGTTTCACC AAGTGCCGGA AGCCATGCAG
1881 CGTGACCAGC TACCAGCTCT CTGCTGGTTA CTCACGATGG
1921 CCCTCGGTGA CATCCCAGGA ATGGGTCTTC CAGATGCTAT
1961 CGCGACAGAA CAATTACACC GTCAACAACA AGAGAAATGG
2001 AGTGGCCAAA GTCAACATCT TCTTCAAGGA GCTGAACTAC
2041 AAAACCAATT CTGAGTCTCC CTCTGTCACG ATGGTCACCC
2081 TCCTGTCCAA CCTGGGCAGC CAGTGGAGCC TGTGGTTCGG
2121 CTCCTCGGTG TTGTCTGTGG TGGAGATGGC TGAGCTCGTC
2161 TTTGACCTGC TGGTCATCAT GTTCCTCATG CTGCTCCGAA
2201 GGTTCCGAAG CCGATACTGG TCTCCAGGCC GAGGGGGCAG
2241 GGGTGCTCAG GAGGTAGCCT CCACCCTGGC ATCCTCCCCT
2281 CCTTCCCACT TCTGCCCCCA CCCCATGTCT CTGTCCTTGT
2321 CCCAGCCAGG CCCTGCTCCC TCTCCAGCCT TGACAGCCCC
2361 TCCCCCTGCC TATGCCACCC TGGGCCCCCG CCCATCTCCA
2401 GGGGGCTCTG CAGGGGCCAG TTCCTCCACC TGTCCTCTGG
2441 GGGGGCCCTG AGAGGGAAGG AGAGGTTTCT CACACCAAGG
2481 CAGATGCTCC TCTGGTGGGA GGGTGCTGGC CCTGGCAAGA
2521 TTGAAGGATG TGCAGGGCTT CCTCTCAGAG CCGCCCAAAC
2561 TGCCGTTGAT GTGTGGAGGG GAAGCAAGAT GGGTAAGGGC
2601 TCAGGAAGTT GCTCCAAGAA CAGTAGCTGA TGAAGCTGCC
2641 CAGAAGTGCC TTGGCTCCAG CCCTGTACCC CTTGGTACTG
2681 CCTCTGAACA CTCTGGTTTC CCCACCCAAC TGCGGCTAAG
2721 TCTCTTTTTC CCTTGGATCA GCCAAGCGAA ACTTGGAGCT
2761 TTGACAAGGA ACTTTCCTAA GAAACCGCTG ATAACCAGGA
2801 CAAAACACAA CCAAGGGTAC ACGCAGGCAT GCACGGGTTT
2841 CCTGCCCAGC GACGGCTTAA GCCAGCCCCC GACTGGCCTG
2881 GCCACACTGC TCTCCAGTAG CACAGATGTC TGCTCCTCCT
2921 CTTGAACTTG GGTGGGAAAC CCCACCCAAA AGCCCCCTTT
2961 GTTACTTAGG CAATTCCCCT TCCCTGACTC CCGAGGGCTA
3001 GGGCTAGAGC AGACCCGGGT AAGTAAAGGC AGACCCAGGG
3041 CTCCTCTAGC CTCATACCCG TGCCCTCACA GAGCCATGCC
3081 CCGGCACCTC TGCCCTGTGT CTTTCATACC TCTACATGTC
3121 TGCTTGAGAT ATTTCCTCAG CCTGAAAGTT TCCCCAACCA
3161 TCTGCCAGAG AACTCCTATG CATCCCTTAG AACCCTGCTC
3201 AGACACCATT ACTTTTGTGA ACGCTTCTGC CACATCTTGT
3241 CTTCCCCAAA ATTGATCACT CCGCCTTCTC CTGGGCTCCC
3281 GTAGCACACT ATAACATCTG CTGGAGTGTT GCTGTTGCAC
3321 CATACTTTCT TGTACATTTG TGTCTCCCTT CCCAACTAGA
3361 CTGTAAGTGC CTTGCGGTCA GGGACTGAAT CTTGCCCGTT
3401 TATGTATGCT CCATGTCTAG CCCATCATCC TGCTTGGAGC
3441 AAGTAGGCAG GAGCTCAATA AATGTTTGTT GCATGAAGGA
3481 AAAAAAAAAA AAAAAAA
```

The rs2228576 single nucleotide polymorphism (SNP) is present in the SCNN1A gene, where the variable nucleotide is at about position 2428 in SEQ ID NO:21 (underlined), which can be adenine in some individuals and guanine in others. The rs2228576 sequence (SEQ ID NO:22) is shown below, where the underlined A/G is the SNP.

GGGCTCTGCAGGGGCCAGTTCCTCC[A/G]CCTGTCCTCTGGGGGGGCC
CTGAGA

The human the epithelial Na+ channel encoded by the SCNN1A cDNA with SEQ ID NO:21 has the following sequence (SEQ ID NO:23).

1 MGMARGSLTR VPGVMGEGTQ GPELSLDPDP CSPQSTPGLM

41 KGNKLEEQDP RPLQPIPGLM EGNKLEEQDS SPPQSTPGLM

81 KGNKREEQGL GPEPAAPQQP TAEEEALIEF HRSYRELFEF

121 FCNNTTIHGA IRLVCSQHNR MKTAFWAVLW LCTFGMMYWQ

161 FGLLFGEYFS YPVSLNINLN SDKLVFPAVT ICTLNPYRYP

201 EIKEELEELD RITEQTLFDL YKYSSFTTLV AGSRSRRDLR

241 GTLPHPLQRL RVPPPPHGAR RARSVASSLR DNNPQVDWKD

281 WKIGFQLCNQ NKSDCFYQTY SSGVDAVREW YRFHYINILS

321 RLPETLPSLE EDTLGNFIFA CRFNQVSCNQ ANYSHFHHPM

361 YGNCYTFNDK NNSNLWMSSM PGINNGLSLM LRAEQNDFIP

401 LLSTVTGARV MVHGQDEPAF MDDGGFNLRP GVETSISMRK

481 QESMIKECGC AYIFYPRPQN VEYCDYRKHS SWGYCYYKLQ

521 VDFSSDHLGC FTKCRKPCSV TSYQLSAGYS RWPSVTSQEW

561 VFQMLSRQNN YTVNNKRNGV AKVNIFFKEL NYKTNSESPS

601 VTMVTLLSNL GSQWSLWFGS SVLSVVEMAE LVFDLLVIMF

641 LMLLRRFRSR YWSPGRGGRG AQEVASTLAS SPPSHFCPHP

681 MSLSLSQPGP APSPALTAPP PAYATLGPRP SPGGSAGASS

721 STCPLGGP

Another cDNA sequence for the human SCNN1A gene with the same SNP is available from the NCBI database as accession number NM_001038.5 (GI:227430285). This sequence is provided below as SEQ ID NO:24.

1 CTTGCCTGTC TGCGTCTAAA GCCCCTGCCC AGAGTCCGCC

41 TTCTCAGGTC CAGTACTCCC AGTTCACCTG CCCTCGGGAG

81 CCCTCCTTCC TTCGGAAAAC TCCCGGCTCT GACTCCTCCT

121 CAGCCCCTCC CCCCGCCCTG CTCACCTTTA ATTGAGATGC

161 TAATGAGATT CCTGTCGCTT CCATCCCTGG CCGGCCAGCG

201 GGCGGGCTCC CCAGCCAGGC CGCTGCACCT GTCAGGGGAA

241 CAAGCTGGAG GAGCAGGACC CTAGACCTCT GCAGCCCATA

281 CCAGGTCTCA TGGAGGGGAA CAAGCTGGAG GAGCAGGACT

321 CTAGCCCTCC ACAGTCCACT CCAGGGCTCA TGAAGGGGAA

361 CAAGCGTCAG GAGCAGGGGC TGGGCCCCGA ACCTGCGGCG

401 CCCCAGCAGC CCACGGCGGA GGAGGAGGCC CTGATCGAGT

441 TCCACCGCTC CTACCGAGAG CTCTTCGAGT TCTTCTGCAA

481 CAACACCACC ATCCACGGCG CCATCCGCCT GGTGTGCTCC

521 CAGCACAACC GCATGAAGAC GGCCTTCTGG GCAGTGCTGT

561 GGCTCTGCAC CTTTGGCATG ATGTACTGGC AATTCGGCCT

601 GCTTTTCGGA GAGTACTTCA GCTACCCCGT CAGCCTCAAC

641 ATCAACCTCA ACTCGGACAA GCTCGTCTTC CCCGCAGTGA

681 CCATCTGCAC CCTCAATCCC TACAGGTACC CGGAAATTAA

721 AGAGGAGCTG GAGGAGCTGG ACCGCATCAC AGAGCAGACG

-continued

761 CTCTTTGACC TGTACAAATA CAGCTCCTTC ACCACTCTCG

801 TGGCCGGCTC CCGCAGCCGT CGCGACCTGC GGGGGACTCT

841 GCCGCACCCC TTGCAGGGCC TGAGGGTCCC GCCCCCGCCT

881 CACGGGGCCC GTCGAGCCCG TAGCGTGGCC TCCAGCTTGC

921 GGGACAACAA CCCCCAGGTG GACTGGAAGG ACTGGAAGAT

961 CGGCTTCCAG CTGTGCAACC AGAACAAATC GGACTGCTTC

1001 TACCAGACAT ACTCATCAGG GGTGGATGCG GTGAGGGAGT

1041 GGTACCGCTT CCACTACATC AACATCCTGT CGAGGCTGCC

1081 AGAGACTCTG CCATCCCTGG AGGAGGACAC GCTGGGCAAC

1121 TTCATCTTCG CCTGCCGCTT CAACCAGGTC TCCTGCAACC

1161 AGGCGAATTA CTCTCACTTC CACCACCCGA TGTATGGAAA

1201 CTGCTATACT TTCAATGACA AGAACAACTC CAACCTCTGG

1241 ATGTCTTCCA TGCCTGGAAT CAACAACGGT CTGTCCCTGA

1281 TGCTGCGCGC AGAGCAGAAT GACTTCATTC CCCTGCTGTC

1321 CACAGTGACT GGGGCCCGGG TAATGGTGCA CGGGCAGGAT

1361 GAACCTGCCT TTATGGATGA TGGTGGCTTT AACTTGCGGC

1401 CTGGCGTGGA GACCTCCATC AGCATGAGGA AGGAAACCCT

1441 GGACAGACTT GGGGGCGATT ATGGCGACTG CACCAAGAAT

1481 GGCAGTGATG TTCCTGTTGA GAACCTTTAC CCTTCAAAGT

1521 ACACACAGCA GGTGTGTATT CACTCCTGCT TCCAGGAGAG

1561 CATGATCAAG GAGTGTGGCT GTGCCTACAT CTTCTATCCG

1601 CGGCCCCAGA ACGTGGAGTA CTGTGACTAC AGAAAGCACA

1641 GTTCCTGGGG GTACTGCTAC TATAAGCTCC AGGTTGACTT

1681 CTCCTCAGAC CACCTGGGCT GTTTCACCAA GTGCCGGAAG

1721 CCATGCAGCG TGACCAGCTA CCAGCTCTCT GCTGGTTACT

1761 CACGATGGCC CTCGGTGACA TCCCAGGAAT GGGTCTTCCA

1801 GATGCTATCG CGACAGAACA ATTACACCGT CAACAACAAG

1841 AGAAATGGAG TGGCCAAAGT CAACATCTTC TTCAAGGAGC

1881 TGAACTACAA AACCAATTCT GAGTCTCCCT CTGTCACGAT

1921 GGTCACCCTC CTGTCCAACC TGGGCAGCCA GTGGAGCCTG

1961 TGGTTCGGCT CCTCGGTGTT GTCTGTGGTG GAGATGGCTG

2001 AGCTCGTCTT TGACCTGCTG GTCATCATGT TCCTCATGCT

2041 GCTCCGAAGG TTCCGAAGCC GATACTGGTC TCCAGGCCGA

2081 GGGGGCAGGG GTGCTCAGGA GGTAGCCTCC ACCCTGGCAT

2121 CCTCCCCTCC TTCCCACTTC TGCCCCCACC CCATGTCTCT

2161 GTCCTTGTCC CAGCCAGGCC CTGCTCCCTC TCCAGCCTTG

2201 ACAGCCCCTC CCCCTGCCTA TGCCACCCTG GGCCCCCGCC

2241 CATCTCCAGG GGGCTCTGCA GGGGCCAGTT CCTCCACCTG

2281 TCCTCTGGGG GGGCCCTGAG AGGGAAGGAG AGGTTTCTCA

2321 CACCAAGGCA GATGCTCCTC TGGTGGGAGG GTGCTGGCCC

2361 TGGCAAGATT GAAGGATGTG CAGGGCTTCC TCTCAGAGCC

-continued

```
2401 GCCCAAACTG CCGTTGATGT GTGGAGGGGA AGCAAGATGG
2441 GTAAGGGCTC AGGAAGTTGC TCCAAGAACA GTAGCTGATG
2481 AAGCTGCCCA GAAGTGCCTT GGCTCCAGCC CTGTACCCCT
2521 TGGTACTGCC TCTGAACACT CTGGTTTCCC CACCCAACTG
2561 CGGCTAAGTC TCTTTTTCCC TTGGATCAGC CAAGCGAAAC
2601 TTGGAGCTTT GACAAGGAAC TTTCCTAAGA AACCGCTGAT
2641 AACCAGGACA AAACACAACC AAGGGTACAC GCAGGCATGC
2681 ACGGGTTTCC TGCCCAGCGA CGGGTTAAGC CAGCCCCGGA
2721 CTGGCCTGGC CACACTGCTC TCCAGTAGCA CAGATGTCTG
2761 CTCCTCCTCT TGAACTTGGG TGGGAAACCC CACCCAAAAG
2801 CCCCCTTTGT TACTTAGGCA ATTCCCCTTC CCTGACTCCC
2841 GAGGGCTAGG GCTAGAGCAG ACCCGGGTAA GTAAAGGCAG
2881 ACCCAGGGCT CCTCTAGCCT CATACCCGTG CCCTCACAGA
2921 GCCATGCCCC GGCACCTCTG CCCTGTGTCT TTCATACCTC
2961 TACATGTCTG CTTGAGATAT TTCCTCAGCC TGAAAGTTTC
3001 CCCAACCATC TGCCAGAGAA CTCCTATGCA TCCCTTAGAA
3041 CCCTGCTCAG ACACCATTAC TTTTGTGAAC GCTTCTGCCA
3081 CATCTTGTCT TCCCCAAAAT TGATCACTCC GCCTTCTCCT
3121 GGGCTCCCGT AGCACACTAT AACATCTGCT GGAGTGTTGC
3161 TGTTGCACCA TACTTTCTTG TACATTTGTG TCTCCCTTCC
3201 CAACTAGACT GTAAGTGCCT TGCGGTCAGG GACTGAATCT
3241 TGCCCGTTTA TGTATGCTCC ATGTCTAGCC CATCATCCTG
3281 CTTGGAGCAA GTAGGCAGGA GCTCAATAAA TGTTTGTTGC
3321 ATGAAGGAAA AAAAAAAAAA AAAAA
```

The human epithelial Na+ channel encoded by the SCNN1A cDNA with SEQ ID NO:24 has the following sequence (SEQ ID NO:25).

```
  1 MEGNKLEEQD SSPPQSTPGL MKGNKREEQG LGSEPAAPQQ
 41 PTAEEEALIE FHRSYRELFE FFCNNTTIHG AIRLVCSQHN
 81 RMKTAFWAVL WLCTFGMMYW QFGLLFGEYF SYPVSLNINL
121 NSDKLVFPAV TICTLNPYRY PEIKEELEEL DRITEQTLFD
161 LYKYSSFTTL VAGSRSRRDL RGTLPHPLQR LRVPPPPHGA
201 PRARSVASSL RDNNPQVDWK DWKIGFQLCN QNKSDCFYQT
241 YSSGVDAVRE WYRFHYINIL SRLPETLPSL EEDTLGNFIF
281 ACRFNQVSCN QANYSHFHHP MYGNCYTFND KNNSNLWMSS
321 MPGINNGLSL MLRAEQNDFI PLLSTVTGAR VMVHGQDEPA
361 FMDDGGFNLR PGVETSISMR KETLDRLGGD YGDCTKNGSD
401 VPVENLYPSK YTQQVCIHSC FQESMIKECG CAYIFYPRPQ
441 NVEYCDYRKH SSWGYCYYKL QVDFSSDHLG CFTKCRKPCS
481 VTSYQLSAGY SRWPSVTSQE WVFQMLSRQN NYTVNNKRNG
```

-continued

```
521 VAKVNIFFKE LNYKTNSESP SVTMVTLLSN LGSQWSLWFG
561 SSVLSVVEMA ELVFDLLVIM FLMLLRRFRS RYWSPGRGGR
601 GAQEVASTLA SSPPSHFCPH PMSLSLSQPG PAPSPALTAP
641 PPAYATLGPR PSPGGSAGAS SSTCPLGGP
```

Note that the underlined threonine at position 722 of the SEQ ID NO:23 SCNN1A protein, and the underlined threonine at position 663 of the SEQ ID NO:25 SCNN1A protein, is threonine because some individuals have nucleotide sequence SEQ ID NO:22, where the variable nucleotide is adenine. However, position 722 of SEQ ID NO:23 and position 663 of SEQ ID NO:25 can be alanine in some individuals because those individuals have guanine as the variable nucleotide in sequence SEQ ID NO:22.

Patients with the threonine substitution in SCNN1A (adenine in rs2228576) have more functional $Na^+$ channels and consequently higher activity higher voltage currents across the cells. Hence, patients with such a threonine at the variable site in SCNN1A are more susceptible to hypertension than SCNN1A proteins with alanine at that position. Patients with the threonine substitution in SCNN1A can benefit from administration of amiloride.

Common and functional genetic variation of alpha adducin at amino acid 460 has also been identified where some individuals have glycine and others have tryptophan. A cDNA sequence for the human alpha adducin gene (ADD1) is available from the NCBI database as accession number NM 001119.4

```
  1 GCACCCAGGT CGGGCGGTGG GGGCGAGCGG AGGGGCTGAG
 41 GGGCGGAGAG GCCTGGCGGG CCGCTGCTGC GGGCCAGGGG
 81 ACGGGGGCGG AGCCGGAGCC GGAGCCGACG GGCGGTGGCC
121 GCACTGGGAC CCCGGAATCC CGCGCGCTGC CCACGATTCG
161 CTTCTGAGGA ACCTAGAAAG ATTGTACAAT GAATGGTGAT
201 TCTCGTGCTG CGGTGGTGAC CTCACCACCC CCGACCACAG
241 CCCCTCACAA GGAGAGGTAC TTCGACCGAG TAGATGAGAA
281 CAACCCAGAG TACTTGAGGG AGAGGAACAT GGCACCAGAC
321 CTTCGCCAGG ACTTCAACAT GATGGAGCAA AAGAAGAGGG
361 TGTCCATGAT TCTGCAAAGC CCTGCTTTCT GTGAAGAATT
401 GGAATCAATG ATACAGGAGC AATTTAAGAA GGGGAAGAAC
441 CCCACAGGCC TATTGGCATT ACAGCAGATT GCAGATTTTA
481 TGACCACGAA TGTACCAAAT GTCTACCCAG CAGCTCCGCA
521 AGGAGGGATG GCTGCCTTAA ACATGAGTCT TGGTATGGTG
561 ACTCCTGTGA ACGATCTTAG AGGATCTGAT TCTATTGCGT
601 ATGACAAAGG AGAGAAGTTA TTACGGTGTA AATTGGCAGC
641 GTTTTATAGA CTAGCAGATC TCTTTGGGTG GTCTCAGCTT
681 ATCTACAATC ATATCACAAC CAGAGTGAAC TCCGAGCAGG
721 AACACTTCCT CATTGTCCCT TTTGGGCTTC TTTACAGTGA
761 AGTGACTGCA TCCAGTTTGG TTAAGATCAA TCTACAAGGA
801 GATATAGTAG ATCGTGGAAG TTAAGATCAA TCTACAAGGA
```

-continued

```
 841 AGGCCGGCTT CACCTTACAC TCTGCAATTT ATGCTGCACG
 881 CCCGGACGTG AAGTGCGTCG TGCACATTCA CACCCCAGCA
 921 GGGGCTGCGG TCTCTGCAAT GAAATGTGGC CTCTTGCCAA
 961 TCTCCCCGGA GGCGCTTTCC CTTGGAGAAG TGGCTTATCA
1001 TGACTACCAT GGCATTCTGG TTGATGAAGA GGAAAAAGTT
1041 TTGATTCAGA AAAATCTGGG GCCTAAAAGC AAGGTTCTTA
1081 TTCTCCGGAA CCATGGGCTC GTGTCAGTTG GAGAGAGCGT
1121 TGAGGAGGCC TTCTATTACA TCCATAACCT TGTGGTTGCC
1161 TGTGAGATCC AGGTTCGAAC TCTGGCCAGT GCAGGAGGAC
1201 CAGACAACTT AGTCCTGCTG AATCCTGAGA AGTACAAAGC
1241 CAAGTCCCGT TCCCCAGGGT CTCCGGTAGG GGAAGGCACT
1281 GGATCGCCTC CCAAGTGGCA GATTGGTGAG CAGGAATTTG
1321 AAGCCCTCAT GCGGATGCTC GATAATCTGG GCTACAGAAC
1361 TGGCTACCCT TATCGATACC CTGCTCTGAG AGAGAAGTCT
1401 AAAAAATACA GCGATGTGGA GGTTCCTGCT AGTGTCACAG
1441 GTTACTCCTT TGCTAGTCAC GGTGATTCGG GCACTTGCTC
1481 CCCACTCAGA CACAGTTTTC AGAAGCAGCA GCGGGAGAAG
1521 ACAAGATGGC TGAACTCTGG CCGGGGCGAC GAAGCTTCCG
1561 AGGAAGGGCA GAATGGAAGC AGTCCCAAGT CGAAGACTAA
1601 GTGGACTAAA GAGGATGGAC ATAGAACTTC CACCTCTGCT
1641 GTCCCTAACC TGTTTGTTCC ATTGAACACT AACCCAAAAG
1681 AGGTCCAGGA GATGAGGAAC AAGATCCGAG AGCAGAATTT
1721 ACAGGACATT AAGACGGCTG GCCCTCAGTC CCAGGTTTTG
1761 TGTGGTGTAG TGATGGACAG GAGCCTCGTC CAGGGAGAGC
1801 TGGTGACGGC CTCCAAGGCC ATCATTGAAA AGGAGTACCA
1841 GCCCCACGTC ATTGTGAGCA CCACGGGCCC CAACCCCTTC
1881 ACCACACTCA CAGACCGTGA GCTGGAGGAG TACCGCAGGG
1921 AGGTGGAGAG GAAGCAGAAG GGCTCTGAAG AGAATCTGGA
1961 CGAGGCTAGA GAACAGAAAG AAAAGAGTCC TCCAGACCAG
2001 CCTGCGGTCC CCCACCCGCC TCCCAGCACT CCCATCAAGC
2041 TGGAGGAAGA CCTTGTGCCG GAGCCGACTA CTGGAGATGA
2081 CAGTGATGCT GCCACCTTTA AGCCAACTCT CCCCGATCTG
2121 TCCCCTGATG AACCTTCAGA AGCACTCGGC TTCCCAATGT
2161 TAGAGAAGGA GGAGGAAGCC CATAGACCCC CAAGCCCCAC
2201 TGAGGCCCCT ACTGAGGCCA GCCCCGAGCC AGCCCCAGAC
2241 CCAGCCCCGG TGGCTGAAGA GGCTGCCCCC TCAGCTGTCG
2281 AGGAGGGGGC CGCCGCGGAC CCTGGCAGCG ATGGGTCTCC
2321 AGGCAAGTCC CCGTCCAAAA AGAAGAAGAA GTTCCGTACC
2361 CCGTCCTTTC TGAAGAAGAG CAAGAAGAAG AGTGACTCCT
2401 GAAACCCCTG CGCTAACACT GTCCTGTCCG GAGCGACCCT
2441 GGCTCTGCCA GCGTCCCCGG CCACGTCTGT GCTCTGTCCT
```

-continued

```
2481 TGTGTAATGG AATGCAAAAA AGCCAAGCCC TCCGCCTAGA
2521 GGTCCCCTCA CGTGACCAGC CCCGTGTAGC CCCGGGCTGA
2561 CCCAGTGTGT GCTCAGCAGC CCCACCCCAC CCTGCCCCTT
2601 GTCCTCTCAG AGCCTCAGCT TCTGGGGGAG ACATGCTCTC
2641 CCCACAGGGG GGAGGCACTA AGTCATGGTC CTGGCTGGAA
2681 GGTACTGAAG GCTTCTGCAG CTTTGGCTGC ACGTCACCCT
2721 CCTGAGCCTC ACCTTTCCTG CCGTCCCTCC TGTTGTGAAA
2761 TCACCACATT CTGTCTCTGC TTGGCTTCCC CTCCACCCTA
2801 AAGTCTCAGG TGACGGACTC AGACTCCTGG CTTCATGTGG
2841 CATTCTCTCT GCTCAGTGAT CTCACTTAAA TCTATATACA
2881 AAGCCTTGGT CCCGTGAAAA CACTCGTGTG CCCACCAGCG
2921 GCCTTGAAGA GGCAGGTCTG GGCCAGATGC TGGGCAGGAA
2961 ACCCCAGCGG CAGATGGGCC TGTGTGCACC CAACGTGATG
3001 CTATGCATGT CTGACCGACG ATCCCTCGAC CAGAATCAGA
3041 TTCAGGAGCT CAGTTTCTTT TTCACTTGGG TCTCTGGATT
3081 CCTGTCATAG GGAAGGTATA TCAGGAGGGG AAGAGGCCTT
3121 TCTAGAATTT TCTTTGAGCA GGTTTACAAT TTAGCTTACA
3161 TTTTTCGACT GTGAACGTGA ATAGGCTGCT TTTTGCTTTC
3201 TTCTTTCCAG ACCCCACAGT AGAGCACTTT TCACTTATTT
3241 GGGGGAGGCT TCAGGGGACT GTTCTCACCT TAACTCAGCC
3281 AGAAAGATGC CCTAGTTGTG ATCAAAGGTA ACTCGAGGTG
3321 GAGGGTAGCC CTGGGGCCCC TCGACATCAC CGTCATTGAT
3361 GGAGCCTGAA CCGTGTGCTC CTCGGCAGAT GCTGTTGTTG
3401 TTACTTCCCT CCAAGAGGCT GGAAAAGGGC TCAGAGCTGC
3441 TGAGCAGGAA CCGGAGGGTG ACCCATTTCA GGAGGTGCCG
3481 GTACCACCCT GACTAGGTAC AGGCAAGCTT GTGTGGGCCC
3521 AACAGGCCCT TGGTAGAGCT GGTGCCAGAT GTGGGCTCAG
3561 ATCCTGGGCA TGATGGGCCG AGCCACCTCG GATCCCACTG
3601 ATTGGCCAGC CGAGCGAGAA CCAGGCTGCT GCATGGCACT
3641 GACCGCCGCT TCCAGCTTCC TCTGAGCCGC AGGGCCTGCT
3681 ACGCGGGCAA GCGTGCTGCC TCTCTTCTGT GTCGTTTTGT
3721 TGCCAAGGCA GAATGAAAAG TCCTTAACCG TGGACTCTTC
3761 CTTTATCCCC TCCTTTACCC CACATATGCA ATGACTTTTA
3801 ATTTTCACTT TTGTAGTTTA ATCCTTTGTA TTACAACATG
3841 AAATATAGTT GCATATATGG ACACCGACTT GGGAGGACAG
3881 GTCCTGAATG TCCTTTCTCC AGTGTAACAT GTTTTACTCA
3921 CAAATAAAAT TCTTTCAGCA AGTTCCTTGT CTAAAAAAAA
3961 AAAAAAAAAA
```

The rs4961 single nucleotide polymorphism (SNP) is present in the ADD1 gene, where the variable nucleotide is at about position 1566 in SEQ ID NO:26 (underlined), which can be guanine in some individuals and thymine in others. The rs4961 sequence (SEQ ID NO:27) is shown below, where the underlined G/T is the SNP.

CCGGGGCGACGAAGCTTCCGAGGAA[G/T]GGCACAATGGAGCAGTCCC AAGTC.

The human alpha adducin encoded by the ADD1 cDNA with SEQ ID NO:26 has the following sequence (SEQ ID NO:28).

```
  1 MNGDSRAAVV TSPPPTTAPH KERYFDRVDE NNPEYLRERN
 41 MAPDLRQDFN MMEQKKRVSM ILQSPAFCEE LESMIQEQFK
 81 KGKNPTGLLA LQQIADFMTT NVPNVYPAAP QGGMAALNMS
121 LGMVTPVNDL RGSDSIAYDK GEKLLRCKLA AFYRLADLFG
161 WSQLIYNHIT TRVNSEQEHF LIVPFGLLYS EVTASSLVKI
201 NLQGDIVDRG STNLGVNQAG FTLHSAIYAA RPDVKCVVHI
241 HTPAGAAVSA MKCGLLPISP EALSLGEVAY HDYHGILVDE
281 EEKVLIQKNL GPKSKVLILR NHGLVSVGES VEEAFYYIHN
321 LVVACEIQVR TLASAGGPDN LVLLNPEKYK AKSRSPGSPV
361 GEGTGSPPKW QIGEQEFEAL MRMLDNLGYR TGYPYRYPAL
401 REKSKKYSDV EVPASVTGYS FASDGDSGTC SPLRHSFQKQ
441 QREKTRWLNS GRGDEASEEG QNGSSPKSKT KWTKEDGHRT
481 STSAVPNLFV PLNTNPKEVQ EMRNKIREQN LQDIKTAGPQ
521 SQVLCGVVMD RSLVQGELVT ASKAIIEKEY QPHVIVSTTG
561 PNPFTTLTDR ELEEYRREVE RKQKGSEENL DEAREQKEKS
601 PPDQPAVPHP PPSTPIKLEE DLVPEPTTGD DSDAATFKPT
641 LPDLSPDEPS EALGFPMLEK EEEAHRPPSP TEAPTEASPE
681 PAPDPAPVAE EAAPSAVEEG AAADPGSDGS PGKSPSKKKK
721 KFRTPSFLKK SKKKSDS
```

Note that the underlined glycine at position 460 of the SEQ ID NO:28 alpha adducin protein is glycine because some individuals have nucleotide sequence SEQ ID NO:26, where the variable nucleotide at position 1566 is guanine. However, position 460 of SEQ ID NO:28 can be tryptophan in some individuals because those individuals have thymine as the variable nucleotide at position 1566 in sequence SEQ ID NO:28.

Individuals with the tryptophan variant of alpha adducin are more likely to be salt sensitive, more likely to have hypertension and have a greater response to diuretics.

Genetic variation of the sodium ($Na^+$) chloride ($Cl^-$) co-transporter (SLC12A3) also has blood pressure consequences. A cDNA sequence for the sodium ($Na^+$) chloride ($Cl^-$) co-transporter (SLC12A3) is available from the NCBI database as accession number NM_000339.2 (GI: 186910314). This SLC12A3 cDNA sequence is provided below as SEQ ID NO:29.

```
  1 CTGGCCCCTC CCTGGACACC CAGGCGACAA TGGCAGAACT
 41 GCCCACAACA GAGACGCCTG GGACGCCAC TTTGTGCAGC
```

-continued

```
  81 GGGCGCTTCA CCATCAGCAC ACTGCTGAGC AGTGATGAGC
 121 CCTCTCCACC AGCTGCCTAT GACAGCAGCC ACCCCAGCCA
 161 CCTGACCCAC AGCAGCACCT TCTGCATGCG CACCTTTGGC
 201 TACAACACGA TCGATGTGGT GCCCACATAT GAGCACTATG
 241 CCAACAGCAC CCAGCCTGGT GAGCCCCGGA AGGTCCGGCC
 281 CACACTGGCT GACCTGCACT CCTTCCTCAA GCAGGAAGGC
 321 AGACACCTGC ATGCCCTGGC CTTTGACAGC CGGCCCAGCC
 361 ACGAGATGAC TGATGGGCTG GTGGAGGGCG AGGCAGGCAC
 401 CAGCAGCGAG AAGAACCCCG AGGAGCCAGT GCGCTTCGGC
 441 TGGGTCAAGG GGGTGATGAT TCGTTGCATG CTCAACATTT
 481 GGGGCGTGAT CCTCTACCTG CGGCTGCCCT GGATTACGGC
 521 CCAGGCAGGC ATCGTCCTGA CCTGGATCAT CATCCTGCTG
 561 TCGGTCACGG TGACCTCCAT CACAGGCCTC TCCATCTCAG
 601 CCATCTCCAC CAATGGCAAG GTCAAGTCAG GTGGCACCTA
 641 CTTCCTCATC TCCCGGAGTC TGGGCCCAGA GCTTGGGGGC
 681 TCCATCGGCC TCATTTTCGC TTTCGCCAAT GCCGTGGGTG
 721 TGGCCATGCA CACGGTGGGC TTTGCAGAGA CCGTGCGGGA
 761 CCTGCTCCAG GAGTATGGGG CACCCATCGT GGACCCCATT
 801 AACGACATCC GCATCATTGG CGTGGTCTCG GTCACTGTGC
 841 TGCTGGCCAT CTCCCTGGCT GGCATGGAGT GGGAGTCCAA
 881 GGCCCAGGTG CTGTTCTTCC TTGTCATCAT GGTCTCCTTT
 921 GCCAACTATT TAGTGGGGAC GCTGATCCCC CCATCTGAGG
 961 ACAAGGCCTC CAAAGGCTTC TTCAGCTACC GGGCGGACAT
1001 TTTTGTCCAG AACTTGGTGC CTGACTGGCG GGGTCCAGAT
1041 GGCACCTTCT TCGGAATGTT CTCCATCTTC TTCCCCTCGG
1081 CCACAGGCAT CCTGGCAGGG GCCAACATAT CTGGTGACCT
1121 CAAGGACCCT GCTATAGCCA TCCCCAAGGG GACCCTCATG
1161 GCCATTTTCT GGACGACCAT TTCCTACCTG GCCATCTCAG
1201 CCACCATTGG CTCCTGCGTG GTGCGTGATG CCTCTGGGGT
1241 CCTGAATGAC ACAGTGACCC CTGGCTGGGG TGCCTGCGAG
1281 GGGCTGGCCT GCAGCTATGG CTGGAACTTC ACCGAGTGCA
1321 CCCAGCAGCA CAGCTGCCAC TACGGCCTCA TCAACTATTA
1361 CCAGACCATG AGCATGGTGT CAGGCTTCGC GCCCCTGATC
1401 ACGGCTGGCA TCTTCGGGGC CACCCTCTCC TCTGCCCTGG
1441 CCTGCCTTGT CTCTGCTGCC AAAGTCTTCC AGTGCCTTTG
1481 CGAGGACCAG CTGTACCCAC TGATCGGCTT CTTCGGCAAA
1521 GGCTATGGCA AGAACAAGGA GCCCGTGCGT GGCTACCTGC
1561 TGGCCTACGC CATCGCTGTG GCCTTCATCA TCATCGCTGA
1601 GCTCAACACC ATAGCCCCCA TCATTTCCAA CTTCTTCCTC
1641 TGCTCCTATG CCCTCATCAA CTTCAGCTGC TTCCACGCCT
1681 CCATCACCAA CTCGCCTGGG TGGAGACCTT CATTCCAATA
```

-continued

```
1721 CTACAACAAG TGGGCGGCGC TGTTTGGGGC TATCATCTCC
1761 GTGGTCATCA TGTTCCTCCT CACCTGGTGG GCGGCCCTCA
1801 TCGCCATTGG CGTGGTGCTC TTCCTCCTGC TCTATGTCAT
1841 CTACAAGAAG CCAGAGGTAA ATTGGGGCTC CTCGGTACAG
1881 GCTGGCTCCT ACAACCTGGC CCTCAGCTAC TCGGTGGGCC
1921 TCAATGAGGT GGAAGACCAC ATCAAGAACT ACCGCCCCCA
1961 GTGCCTGGTG CTCACGGGGC CCCCCAACTT CCGCCCGGCC
2001 CTGGTGGACT TTGTGGGCAC CTTCACCCGG AACCTCAGCC
2041 TGATGATCTG TGGCCACGTG CTCATCGGAC CCCACAAGCA
2081 GAGGATGCCT GAGCTCCAGC TCATCGCCAA CGGGCACACC
2121 AAGTGGCTGA ACAAGAGGAA GATCAAGGCC TTCTACTCGG
2161 ATGTCATTGC CGAGGACCTC CGCAGAGGCG TCCAGATCCT
2201 CATGCAGGCC GCAGGTCTCG GGAGAATGAA GCCCAACATT
2241 CTGGTGGTTG GGTTCAAGAA GAACTGGCAG TCGGCTCACC
2281 CGGCCACAGT GGAAGACTAC ATTGGCATCC TCCATGATGC
2321 CTTTGATTTC AACTATGGCG TGTGTGTCAT GAGGATGCGG
2361 GAGGGACTCA ACGTGTCCAA GATGATGCAG GCGCACATTA
2401 ACCCCGTGTT TGACCCAGCG GAGGACGGGA AGGAAGCCAG
2441 CGCCAGAGGT GCCAGGCCAT CAGTCTCTGG CGCTTTGGAC
2481 CCCAAGGCCC TGGTGAAGGA GGAGCAGGCC ACCACCATCT
2521 TCCAGTCGGA GCAGGGCAAG AAGACCATAG ACATCTACTG
2561 GCTCTTTGAC GATGGAGGCC TCACCCTCCT CATTCCCTAT
2601 CTCCTTGGCC GCAAGAGGAG GTGGAGCAAA TGCAAGATCC
2641 GTGTGTTCGT AGGCGGCCAG ATTAACAGGA TGGACCAGGA
2681 GAGAAAGGCG ATCATTTCTC TGCTGAGCAA GTTCCGACTG
2721 GGATTCCATG AAGTCCACAT CCTCCCTGAC ATCAACCAGA
2761 ACCCTCGGGC TGAGCACACC AAGAGGTTTG AGGACATGAT
2801 TGCACCCTTC CGTCTGAATG ATGGCTTCAA GGATGAGGCC
2841 ACTGTCAACG AGATGCGGCG GGACTGCCCC TGGAAGATCT
2881 CAGATGAGGA GATTACGAAG AACAGAGTCA AGTCCCTTCG
2921 GCAGGTGAGG CTGAATGAGA TTGTGCTGGA TTACTCCCGA
2961 GACGCTGCTC TCATCGTCAT CACTTTGCCC ATAGGGAGGA
3001 AGGGGAAGTG CCCCAGCTCG CTGTACATGG CCTGGCTGGA
3041 GACCCTGTCC CAGGACCTCA GACCTCCAGT CATCCTGATC
3081 CGAGGAAACC AGGAAAACGT GCTCACCTTT TACTGCCAGT
3121 AACTCCAGGC TTTGACATCC CTGTCCACAG CTCTGAGTGT
3161 GTGGGATAAG TTGGAACTTG ATTGCCTCTA GTCCACAGGG
3201 ATGAGACTCA TGTTCTGTTG CACTTTAAGT GGCAGCATCT
3241 GATGATCTCA CCGAAAAAGA TGGTAGATTT CCAAATCTGG
3281 CTGGACTCCA CTTCCATGGG ACACATTCCC TGGGTCTTGT
```

-continued

```
3321 GTTTATAGGC TAGAGAAATA GCAGATGGAG CTGCAAGGAA
3361 AACTCTCTAA AGCATCCTAT TCCTTTTAAA GGATTTCTTT
3401 TGATTTTGAT GACCATTAAT TAAGAGTTCA GTCTTTGATT
3441 TGTATGCAAA TTGGAGTCCC AATGCTGGGC GTGAATCTTG
3481 ACAGTTTCTA CAGACCTTCC TGGGTGAAAG TTCCTAAATC
3521 ATGCCCTGCT TCCTCCAATA GGAGAATGGG AGCCTCACCT
3561 GTAGGACCTA CAGGCTCTCT AAGGAATGCA GGTCTCTCTC
3601 TGAGCCTCCA CAGCCAGGCA AATACATATA TATATATTTT
3641 TTTTTTAGAT GAAGTTTTTT CTCTTGTTGC CCAGGCTAGG
3681 GTGTAATGGC ATGATCTCAG GTCACTGCAA CCTCCTCCCG
3721 GGTTCAAGCA TTTCTTCTGT CTCAGCCTCC CGAATAGCTG
3761 GGATTACAGG CACCTGCCAT CACACGAGCT AATTTTTGTA
3801 TTTTTAGTAG AGATGGGGTT TCACCATGTT GACCAGGCTG
3841 GTGTTGAGCT CCTGACCTCA GGTGATCCAC CCACCTCGGT
3881 CTCCCAAAGT GCTGGGGTTA CAGGCCTGAG CCACTGCGCC
3921 CGGCCCAGGC AAATTTCTTG AACCACTTCT CACTCCCGTC
3961 ACTTTCAATA AGGGGTCTTT GATGTCTTCA CTGGTTCTTT
4001 GGACCAGGGA CTTTTCGAAC TTTTTTGGTT GCAACACACA
4041 GTAAGAAATA TACTTCACAC TGAGACTTGC AGCGCACACA
4081 CACGGAAACG ACCAAAACAA AAATGTCACA AAACAATACT
4121 TACCCTTCCC TGGGGGACGT CCTCCAGTAT GTTCTGTTCT
4161 GTTTATTTTT CACTGTTGGT TGCAATCCAA TAAAATGACT
4201 TTGGGATCCA CTCATGGGTG GGGACCCACA CATTTGAAAG
4241 GCATGGCCAC CTTTCTGTTG TGCCTTGCAT TTGTCCACAC
4281 ACAGGGAGTC TGGCTGAGCT GGGGAAAGGC CACGCCTGGG
4321 TGTCATTGCC ATTTTCCCAG CTCATCTCAC CGGGAAGAAA
4361 AGCACATTGA CAGAACACGT GAGGAGGGGT ATTGATGGCA
4001 GGAGAGTCAA AAAAGAGTTT TAAAGAAGGG GCAAGGTTGA
4441 AGGAGTCTAG TGGCAAGGGT AAGATTTCAG GCATGGTTAA
4481 GAACAGACGA CAAGGATGTC AGGAATGAAG ATGTGGAGAG
4521 GGGTGTAGAG ATGGCAAGGT TGGCAAGGAA CAGATAGGCA
4561 GGAGCAGGTC CAAGCCAAGC CTAGCCCAAG ACCAGGTGAA
4601 AGGAGAGGGG AGGAGGAGCC ACCTGCAAGA GATGGAAAGA
4641 GCAGGCGGCA GAGGGGGCTG GCAGGGAGGG GCTGTTAAGA
4681 GTGGGGTTGG AGGTGGGAGA GAAGCTAGGA CAAGGGAGAT
4721 GGAGAAAGGA CCTATACCTG GCTCACGGAA GGCCTTCAGG
4761 TCACTACACG TTGAACATCC CCAGTGTTTG AGCCCCCAAA
4801 GCTAGGGTGC AAGAGCACTG CCATCGAATG CCAGTGGGTG
4841 AGGCCAAGTG AGGGTATTTG CAGCTCTAGA CATAACCAAG
4881 AAGCGTAAAG GTGAGTTGTT TGGTGGTACG ACTGCCTGTG
4921 CCTTCTTCCG ATGGCACTGG GGTGGCTGAA GGAACAGACA
```

-continued

```
4961 TCTTTGGGTT TCATCAGCCT CCTCCAAGAC TGCTGCAGTG
5001 CCTACACTTT AGACTTCAGA AGGAGACTAA AGACTTCTAG
5041 AATTTAGAAG GAGATCTGAA GTCTCCTTTC TGGAGTTACA
5081 ACCCAAAGGA TGTTAGCATT TCTCAGGTCA TCCCACTGCA
5121 AAGCCCAGAA GGCTTGGGGC TCCCAGGCTG CTCTGAAGCC
5161 CCACTGTCTG ACCGCCTCAG GGCTTGCTAC GAGGGACTGG
5201 GGCACGGCCA AGCTGACTAG GAACAGCTCT CGTGCTCCTG
5241 AGGGACCTGG AGGATGGGCC TGCCTCCCAG CCATTGAGCT
5281 GGATTCTGGG ATAATTCTTA ACTCGAAATA AGGGGAAGCA
5321 TCCATCAGGG AATGCTGGCC TTTCTAGAGC CACGTAGAAA
5361 ACAATTTTCT GGTTCTTCAA ACCTCAAAGA GTCCTTGGTC
5401 CAAAAAACAG AATGTTTTGG CTTCGGGTGT CAAAAAAAAA
5441 ATTTTCACGA TGTCAGAAAT AGTATGTTTT TAACAATAGT
5481 AATAGCTTTG TAAAAAAATA AAAAGCTTTA ACAGCGAGGC
5521 CATAAACAAT GAAATGAATA AAAACGGTGG TCATTCAGTC
5561 AACGGAAAAA AAAAAAAAAA AA
```

The rs1529927 single nucleotide polymorphism (SNP) is present in the SLC12A3 gene, where the variable nucleotide is at about position 820 in SEQ ID NO:29 (underlined), which can be guanine in some individuals and cytosine in others. The rs1529927 sequence (SEQ ID NO:30) is shown below, where the underlined C/G is the SNP.

CCCATTAACGACATCCGCATCATTG[C/G]CGTGGTCTCGGTCACTGTG CTGCTG.

The human the sodium ($Na^{+}$) chloride ($Cl^{-}$) co-transporter encoded by the SLC12A3 cDNA with SEQ ID NO:29 has the following sequence (SEQ ID NO:31).

```
   1 MAELPTTETP GDATLCSGRF TISTLLSSDE PSPPAAYDSS
  41 HPSHLTHSST FCMRTFGYNT IDVVPTYEHY ANSTQPGEPR
  81 KVRPTLADLH SFLKQEGRHL HALAFDSRPS HEMTDGLVEG
 121 EAGTSSEKNP EEPVPFGWVK GVMIRCMLNI WGVILYLRLP
 161 WITAQAGIVL TWIIILLSVT VTSITGLSIS AISTNGKVKS
 201 GGTYFLISRS LGPELGGSIG LIFAFANAVG VAMHTVGFAE
 241 TVRDLLQEYG APIVDPINDI RIIGVVSVTV LLAISLAGME
 281 WESKAQVLFF LVIMVSFANY LVGTLIPPSE DKASKGFFSY
 321 RADIFVQNLV PDWRGPDGTF FGMFSIFFPS ATGILAGANI
 361 SGDLKDPAIA IPKGTLMAIF WTTISYLAIS ATIGSCVVRD
 401 ASGVLNDTVT PGWGACEGLA CSYGWNFTEC TQQHSCHYGL
 441 INYYQTMSMV SGFAPLITAG IFGATLSSAL ACLVSAAKVF
 481 QCLCEDQLYP LIGFFGKGYG KNKEPVRGYL LAYAIAVAFI
 521 IIAELNTIAP IISNFFLCSY ALINFSCFHA SITNSPGWRP
```

-continued

```
 561 SFQYYNKWAA LFGAIISVVI MFLLTWWAAL IAIGVVLFLL
 601 LYVIYKKPEV NWGSSVQAGS YNLALSYSVG LNEVEDHIKN
 641 YRPQCLVLTG PPNFRPALVD FVGTFTRNLS LMICGHVLIG
 681 PHKQRMPELQ LIANGHTKWL NKRKIKAFYS DVIAEDLRRG
 721 VQILMQAAGL GRMKPNILVV GFKKNWQSAH PATVEDYIGI
 761 LHDAFDFNYG VCVMRMREGL NVSKMMQAHI NPVFDPAEDG
 801 KEASARGARP SVSGALDPKA LVKEEQATTI FQSEQGKKTI
 841 DIYWLFDDGG LTLLIPYLLG RKRRWSKCKI RVFVGGQINR
 881 MDQERKAIIS LLSKFRLGFH EVHILPDINQ NPRAEHTKRF
 921 EDMIAPFRLN DGFKDEATVN EMRRDCPWKI SDEEITKNRV
 961 KSLRQVRLNE IVLDYSRDAA LIVITLPIGR KGKCPSSLYM
1001 AWLETLSQDL RPPVILIRGN QENVLTFYCQ
```

Note that the underlined glycine at position 264 of the SEQ ID NO:31 sodium ($Na^{+}$) chloride ($Cl^{-}$) co-transporter protein is glycine because some individuals have nucleotide sequence SEQ ID NO:29, where the variable nucleotide at position 820 is guanine. However, position 264 of SEQ ID NO:29 can be alanine in some individuals because those individuals have cytosine as the variable nucleotide at position 820 in sequence SEQ ID NO:29.

Patients with the alanine variant of SLC12A3 (encoded by the rs1529927 site (SEQ ID NO:30)) exhibit a stronger diuretic effect to loop diuretics and demonstrate more excretion of $Cl^{-}$ and $K^{+}$ in response to therapy. Hence, subject with alanine or guanine at the rs1529927 site are more response to diuretics.

The WNK1 gene has functional and common polymorphisms that affect how a subject's blood pressure responds to drugs. Several cDNA sequences for the WNT1 gene are available from the NCBI database.

The rs2107614 single nucleotide polymorphism (SNP) is present in an intron of the WNK1 gene, where the variable nucleotide can be thymine in some individuals and cytosine in others. The rs2107614 sequence (SEQ ID NO:33) is shown below, where the underlined C/T is the SNP.

CACTTCCTCCAAAAAAAAAGAAAAC[C/T]CCATTTCCCCTCAACTCT TCCAGTT.

Another SNP, rs1159744, is present an intron of the WNK1 gene, where the variable nucleotide can be guanine in some individuals and cytosine in others. The rs1159744 sequence (SEQ ID NO:34) is shown below, where the underlined C/G is the SNP.

AATGTTAACAGTATAGAAAATTTTA[C/G]CTCAACAAATAGAGAATAT CAGTAA.

Patients with the cytosine variant of WNK1 at SNP positions rs1159744 and rs2107614 exhibit greater blood pressure reductions in response to loop diuretic therapy when compared to patients with the guanine or thymine variants at these two sites, respectively (Turner et al., *Hypertension* 46:758-765 (2005)).

Therapy

The methods, reagents, devices, and kits described herein can be used for determining whether a subject may benefit from treatment with a blood pressure medication, and which medication can be more effective for treating high blood pressure. For example, the methods described herein can be employed for determining whether a subject should be treated with a diuretic, an angiotensin converting enzyme (ACE) inhibitor, or a beta-blocker. Such determination is performed by identifying or detecting whether the subject has a genetic variant or single nucleotide polymorphism in his or her ADRB1, ADRB2, CYP2D6, angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1 polypeptides or nucleic acids. If testing of the subject's tissue sample shows that the subject has a genetic variant or single nucleotide polymorphism in his or her ADRB1, ADRB2, CYP2D6, angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1 polypeptides or nucleic acids, a suitable therapeutic regimen can be prescribed for the subject.

A diuretic promotes the production or urine. Diuretics are sometimes grouped into three categories: thiazides, loop, and potassium-sparing diuretics. Thiazide diuretics include chlorothiazide, hydrochlorothiazide, indapamide, metolazone, and chlorthalidone. Loop diuretics include furosemide, bumetanide, ethacrynic acid, and torsemide. Examples of potassium-sparing diuretics include amiloride, eplerenone, spironolactone, and triamterene.

Examples of diuretics that can be employed also include furosemide, thiazides, carbonic anhydrase inhibitors, potassium-sparing diuretics (e.g., aldosterone antagonists, spironolactone, eplerenone, potassium canreonate, amiloride, triamterene, aldactone, and combinations thereof), calcium-sparing diuretics, For example, the diuretic can be acetazolamide, amiloride, bumetanide, chlorthalidone, chlorothiazide, ethacrynic acid, furosemide, glycerin, hydrochlorothiazide, hydroflumethiazide, indapamide, isosorbide, mannitol, methazolamide, methylchlothiazide, metolazone, dichlorphenamide, spironolactone, torsemide, triamterene, urea, and combinations thereof.

The angiotensin converting enzyme inhibitor can be selected from enalapril, lisinopril, captopril alacipril, benazapril, cilazapril, delapril, fosinopril, perindopril, quinapril, ramipril, moveltipril, spirapril, ceronapril, imidapril, temocapril, trandolopril, utilbapril, zofenopril, CV5975, EMD 56855, libenzapril, zalicipril, HOE065, MDL 27088, AB47, DU 1777, MDL 27467A, Equaten™, Prentyl™, Synecor™, and Y23785; and the diuretic is selected from hydrochlorothiazide (HCTZ), furosemide, altizide, trichlormethazide, triflumethazide, bemetizide, cyclothiazide, methylchlothiazide, azosemide, chlorothiazide, butizide, bendroflumethazide, cyclopenthiazide, benzclortriazide, polythiazide, hydroflumethiazide, benzthiazide, ethiazide, penflutazide, and any combination thereof.

The angiotensin II receptor antagonists can, for example, be losartan, valsartan, candesartan, irbesartan, olmesartan, or any combination thereof.

The renin inhibitors can be urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES1005, ES 8891, SQ 34017, aliskiren ((2S,4S,5S,7S)—N-(2-carbamoyl-2-methylpropyl)-5-amino-4-hydroxy-2,7-diisopropyl-8-[4-methoxy-3-(3-methoxypropoxy) phenyl]-oetanamid hemifumarate) SPP600, SPP630 and SPP635), or any combination thereof.

Other therapeutic agents can also be administered including endothelin receptors antagonists, vasodilators, calcium channel blockers (e.g., amlodipine, nifedipine, verapamil, diltiazem, gallopamil, nifedipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartrate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetimibe, atorvastatin, pravastatin), metabolic altering agents including insulin sensitizing agents and related compounds (e.g., muraglitazar, glipizide, metformin, rosiglitazone) or with other drugs beneficial for the prevention or the treatment of disease including nitroprusside and diazoxide.

The therapeutic protocol can generally be conducted as follows. An assay of all sixteen genotypes (polymorphic sites) can be performed. The therapeutic decision tree of the results can be as follows.

To ascertain whether a diuretic should be administered to a subject, the following can be performed.

If the subject is (a) homozygous for cytosine at the rs1529927 (SEQ ID NO:30) variable site (expressing alanine at position 264 of the SLC12A3 gene product); (b) homozygous for adenine at the rs2228576 (SEQ ID NO:22) variable site (expressing threonine at about 663 or 722 of the SCNN1A protein); and/or (c) homozygous for thymine at the rs4961 (SEQ ID NO:27) variable site (expressing tryptophan at about position 460 of the adducin protein) then the patient should initially start with a diuretic as the first line of therapy. If the patient is heterozygous at these sites, then genetic variation within the polymorphic sites relating to vasodilator and beta-blocker drug class responses should initially be considered.

If the patient does not carry homozygous variants that are known to be functionally important within the vasodilator and beta-blocker classes, but are heterozygous at rs1529927, rs2228576, and rs4961, then diuretic therapy should initially be considered as first-line therapy.

If the subject is homozygous for cytosine at the WNK1 rs1159744 (SEQ ID NO:34) variable site and also homozygous for cytosine at the WNK1 rs2107614 (SEQ ID NO:33) variable site then the patient should start with a loop diuretic as first-line of therapy.

If the patient does not carry homozygous variants within the vasodilator and beta-blocker classes that are known to be functionally important, but are heterozygous at rs1529927, rs2228576, and rs4961, then loop diuretic therapy should initially be considered as first-line therapeutic agent.

To ascertain whether a vasodilator should be administered to a subject the following can be performed.

If the subject is homozygous for cytosine at the rs5186 (SEQ ID NO:16) variable site of AGT1R, and the subject is homozygous cytosine at the rs12750834 (SEQ ID NO:20) variable site of renin, then the patient should use an angiotensin II (AII) receptor blocker as a first line of therapy.

If the patient is heterozygous for cytosine at the rs5186 and rs12750834 variable sites, but does not present with other important functional genotypes within the diuretic and beta-blockade classes, then the patient should also use an angiotensin II receptor blocker as a first line of therapy.

If the patient is homozygous for cytosine at the rs699 (SEQ ID NO:14) variable site of AGT, or for the deletion at the rs1799752 (SEQ ID NO:12; SEQ ID NO:35) of ACE, then the patient will likely benefit most from an angiotensin-converting enzyme (ACE) inhibitor.

Patients who are homozygous for cytosine at the rs699 (SEQ ID NO:14) will likely benefit most from BOTH ACE inhibition and angiotensin II (AII) receptor blockade.

Patients who are heterozygous for the deletion at the rs1799752 (SEQ ID NO:12; SEQ ID NO:35) and heterozygous for cytosine at the rs699 (SEQ ID NO:14) variable site should be administered other drug classes (e.g., diuretic initially followed by beta-blockade). Although homozygosity at other sites has a greater impact on hypertension than heterozygosity at rs1799752 and rs699, this is generally true only if the patient has combined homozygosity at sites indicating that drug classes other than vasodilators should be administered.

To ascertain whether a beta-blocker should be administered to a subject the following can be performed.

Patients homozygous for adenine at the rs3892097 (SEQ ID NO: 10) variable site of the CYP2D6 gene should initially consider the use of atenolol and carvedilol as therapy. This is PARTICULARLY important if the patient is homozygous for cytosine at the rs1801253 (SEQ ID NO:3) variable site (and expresses arginine at position 389 of the $\beta_1$AR polypeptide), or if the patient is homozygous for adenine at the rs1801252 variable position (and expresses serine at position 49 of the $\beta_1$AR polypeptide).

The rs1042713 (SEQ ID NO:6) and rs1042714 (SEQ ID NO:7) variable sites are less important of the other polymorphism sites within the beta-blocker class of drugs and generally indicate patients who will likely respond to non-selective beta-blockade. Thus, subjects who are homozygous for guanine at the rs1042713 variable site (and express glycine at about position 16 of the ADRB2 gene product) as well as subjects who are homozygous for guanine at the rs1042714 position (and express glutamic acid at $\beta_2$AR position 27) are the most responsive to beta-blocker drugs.

If subjects are non-homozygous for polymorphisms in the beta-blockade class of variants, but are homozygous for cytosine at the rs1801253 (SEQ ID NO:3) variable site (and expresses arginine at position 389 of the $\beta_1$AR polypeptide), or if subjects are homozygous for adenine at the rs1801252 variable position (and expresses serine at position 49 of the $\beta_1$AR polypeptide), the beta-blockade class should be considered a possible line of therapy if they do not carry functional mutations within the diuretic and vasodilator classes of drugs.

Polymorphism Detection

The polymorphism present in genes such as ADRB1, ADRB2, cytochrome P450 2D6 (CYP2D6), angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1 can be detected by any available procedure. For example, samples of cDNA, genomic DNA, and/or mRNA can be obtained from a subject and the sequences of polymorphic or variant sites can be evaluated by procedures such as nucleic acid amplification (e.g., PCR), reverse transcription, insertion/deletion analysis, primer extension, probe hybridization, SNP analysis, sequencing, restriction fragment length polymorphism, Matrix-Assisted Laser Desorption/Ionization Time-Of-Flight mass spectrometry (MALDI-TOF MS), Sequenom MassArray genotyping, Sanger sequencing, polyacrylamide gel electrophoresis, agarose gel electrophoresis, probe array hybridization analysis, and combinations thereof.

The methods for detecting polymorphisms can therefore involve detecting an alteration in a nucleic acid. As used herein a "nucleic acid" is a DNA or RNA molecule. A nucleic acid can be a segment of genomic DNA (e.g., an entire gene, an intron of a gene, an exon of a gene, a segment that includes regulatory elements, a 5' non-coding segment, a 3' non-coding segment, or any combination thereof). The nucleic acid can also be a cDNA (having exons but not introns), an amplicon, an RNA, a primer, or probe.

Probes and/or primers can be used that can hybridize to nucleic acid segments flanking or including of any of SNPs, insertions, deletions, polymorphic, or other variant segments of ADRB1, ADRB2, cytochrome P450 2D6 (CYP2D6), angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1 genes. For example, probes and/or primers can be employed that hybridize to nucleic acid segments flanking or including any of the following polymorphisms: rs1801252 (ADRB1), rs1801253 (ADRB1), rs1042713 (ADRB2), rs1042714 (ADRB2), rs3892097 (CYP2D6), rs1799752 (ACE), rs699 (AGT), rs5186 (AGT1R), rs12750834 (renin), rs2228576 (SCNN1A), rs4961 (ADD1), rs1529927 (SLC12A3), rs2107614 (WNK1), or rs1159744 (WNK1). For example, the probes and/or primers can separately hybridize to segments of any of SEQ ID NO:2, 3, 6, 7, 10, 12, 14, 16, 19, 20, 22, 27, 30, 32, 33, 34, as well as to the complementary sequences, amplicons, cDNA, cRNA, and genomic sequences thereof. The probes and/or primers can hybridize to genomic, complementary, amplicon, or cDNA sequences that flank up to 50 nucleotides of any of SEQ ID NO:2, 3, 6, 7, 10, 12, 14, 16, 19, 20, 22, 27, 30, 33, or 34, on either or both of the 5' and 3' sides of the polymorphism.

Methods and devices described herein can detect at least two of these polymorphisms, or at least three of these polymorphisms, or at least of four of these polymorphisms, or at least five of these polymorphisms, or at least of six of these polymorphisms, or at least seven of these polymorphisms, or at least of eight of these polymorphisms, or at least nine of these polymorphisms, or at least often of these polymorphisms, or at least eleven of these polymorphisms, or at least of twelve of these polymorphisms, or at least thirteen of these polymorphisms, or at least fourteen of these polymorphisms, or at least fifteen of these polymorphisms or all of these polymorphisms. In some embodiments, the methods and devices described herein detect no other polymorphisms, although such methods and devices can include steps and probes for detecting 1-4 control target nucleic acids. For example, the methods, devices, and kits described herein can detect and evaluate about sixteen polymorphisms.

The probes and primers can be of any convenient length selected by one of skill in the art such as at least 12 nucleotides long, or at least 13 nucleotides long, or at least 14 nucleotides long, or at least 15 nucleotides long, or at least 16 nucleotides long, or at least 17 nucleotides long, or at least 18 nucleotides long, or at least 19 nucleotides long, or at least 20 nucleotides long. In some embodiments, the probes and primers can be less than 150 nucleotides in length, or less than 125 nucleotides in length, or less than 100 nucleotides in length, or less than 75 nucleotides in length, or less than 65 nucleotides in length, or less than 60 nucleotides in length, or less than 55 nucleotides in length, or less than 50 nucleotides in length, or less than 45 nucleotides in length, or less than 40 nucleotides in length.

To detect hybridization, it may be advantageous to employ probes, primers and other nucleic acids in combination with an appropriate detection means. Labels incorporated into primers, incorporated into the amplified product during amplification, or attached to probes that can hybridize to the target, or its amplified product, are useful in the identification of nucleic acid molecules. A number of different labels may be used for this purpose including, but not limited to, fluorophores, chromophores, radiolabels, enzymatic tags, antibodies, chemiluminescence, electroluminescence, and affinity labels. One of skill in the art will recognize that these and other labels can be used with success in this invention.

Examples of affinity labels include, but are not limited to the following: an antibody, an antibody fragment, a receptor protein, a hormone, biotin, dinitrophenyl (DNP), or any polypeptide/protein molecule that binds to an affinity label. Examples of enzyme tags include enzymes such as urease, alkaline phosphatase or peroxidase to mention a few. Colorimetric indicator substrates can be employed to provide a detection means visible to the human eye or spectrophotometrically, to identify specific hybridization with complementary nucleic acid-containing samples. Examples of fluorophores include, but are not limited to, Alexa 350. Alexa 430, AMCA, BODIPY 630/650, BODIPY 650/665, BODIPY-FL, BODIPY-R6G. BODIPY-TMR, BODIPY-TRX, Cascade Blue, Cy2, Cy3. Cy5, 6-FAM, Fluorescein, HEX, 6-JOE, Oregon Green 488, Oregon Green 500, Oregon Green 514. Pacific Blue, REG, Rhodamine Green, Rhodamine Red, ROX, TAMRA, TET, Tetramethylrhodamine, and Texas Red.

Means of detecting such labels are well known to those of skill in the art. For example, radiolabels may be detected using photographic film or scintillation counters. In other examples, fluorescent markers may be detected using a photodetector to detect emitted light. In still further examples, enzymatic labels are detected by providing the enzyme with a substrate and detecting the reaction product produced by the action of the enzyme on the substrate, and colorimetric labels are detected by simply visualizing the colored label or by use of spectrometer.

So called "direct labels" are detectable labels that are directly attached to or incorporated into a probe or primer, or to the target (sample) nucleic acid prior to hybridization to a probe that can, for example, be present on a plate, chip, microtiter plate, or microarray. In contrast, so called "indirect labels" are joined to the hybrid duplex after hybridization. In some embodiments, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin-bearing hybrid duplexes providing a label that is easily detected. For a detailed review of methods of labeling nucleic acids and detecting labeled hybridized nucleic acids see, for example, Peter C. van der Vliet & Shiv Pillai, eds., Laboratory Techniques in Biochemistry and Molecular Biology (1993).

Probe arrays, assay plates, and gene chip technology provide a means of rapidly screening a large number of nucleic acid samples for their ability to hybridize to a variety of probes immobilized on a solid substrate that is part of the probe array, assay plate, gene chip or microarray. The technology capitalizes on the complementary binding properties of single stranded nucleic acid probe to screen nucleic acid samples by hybridization (Pease et al., Proc. Natl. Acad. Sci. U.S.A. 91: 5022-5026 (1994); U.S. Patent to Fodor et al. (1991)). Basically, a nucleic acid probe array or gene chip consists of a solid substrate with an attached array of single-stranded probe molecules. In some embodiments, the probes can fold back on (i.e., hybridize to) themselves to quench a signal from an attached label, but the probes unfold to hybridize to a target nucleic acid, whereupon the signal from the attached label becomes detectable. In other embodiments, the probe can be complementary to the segment of a target nucleic acid but the 3' end of the probe terminates one nucleotide short of a SNP in the target nucleic acid. The target nucleic acid can be longer than the probe. A signal can be detected upon primer extension of the probe, where the assay mixture contains just one type of labeled nucleotide that can base pair with the variant nucleotide of the SNP. After washing, the presence or absence of the SNP is detectable by incorporation or non-incorporation of the labeled SNP nucleotide into specific probes of the array or plate.

For screening, the chip, plate, or array is contacted with a nucleic acid sample (e.g., genomic DNA, cRNA, cDNA, or amplified copies thereof), which is allowed to hybridize under stringent conditions. The chip, plate, or array is then scanned to determine which targets have hybridized to which probes. The probes are arrayed in known locations so a signal detected at a specific location indicates that its target has hybridized thereto.

Methods for directly synthesizing on or attaching nucleic acid probes to solid substrates are available in the art. See, e.g., U.S. Pat. Nos. 5,837,832 and 5,837,860, both of which are expressly incorporated by reference herein in their entireties. A variety of methods have been utilized to either permanently or removably attach the probes to the substrate. Exemplary methods include: the immobilization of biotinylated nucleic acid molecules to avidin/streptavidin coated supports (Holmstrom, (Anal. Biochem. 209: 278283 (1993)), the direct covalent attachment of short, 5'-phosphorylated primers to chemically modified polystyrene plates (Rasmussen et al., Anal. Biochem. 198: 138-142 (1991)), or the precoating of the polystyrene or glass solid phases with poly-L-Lys or poly L-Lys, Phe, followed by the covalent attachment of either amino- or sulfhydryl-modified oligonucleotides using bifunctional crosslinking reagents (Running et al., BioTechniques 8: 276 277 (1990); Newton, C. R. et al., Acids Res. 21: 1155-1162 (1993)). When immobilized onto a substrate, the probes are typically stabilized and therefore can be used repeatedly.

Hybridization can performed on an immobilized probe that is attached to a solid surface such as silicon, plastic, nitrocellulose, nylon or glass by addition of one or more target molecules. In some embodiments, the target nucleic acid can be attached to a solid surface and the probe can be added to the immobilized target nucleic acids. Numerous substrate and/or matrix materials can be used, including reinforced nitrocellulose membrane, activated quartz, activated glass, polyvinylidene difluoride (PVDF) membranes, polystyrene, polyacrylamide, poly(vinyl chloride), poly(methyl methacrylate), poly(dimethyl siloxane), photopolymers (which contain photoreactive species such as nitrenes, carbenes and ketyl radicals capable of forming covalent links with target molecules), and combinations thereof.

The term "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, primer extension, or the enzymatic cleavage of a polynucleotide by a ribozyme.

Hybridization reactions can be performed under conditions of different "stringency". The stringency of a hybridization reaction includes the difficulty with which any two nucleic acid molecules will hybridize to one another. Under low to medium stringent conditions, nucleic acid molecules at least 60%, 65%, 70%, 75% identical to each other remain hybridized to each other, whereas molecules with lower percent identity cannot remain hybridized. For detection of single base polymorphisms, higher stringency conditions can be used.

A preferred, non-limiting example of highly stringent hybridization conditions include hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C.

When hybridization occurs in an antiparallel configuration between two single-stranded polynucleotides, the reaction is called "annealing" and those polynucleotides are described as "complementary". A double-stranded polynucleotide can be "complementary" and/or "homologous" to another polynucleotide, if hybridization can occur between one of the strands of the first polynucleotide and the second.

Complementarity" or "homology" (the degree that one polynucleotide is identical or complementary to another) is quantifiable in terms of the proportion of bases in opposing strands that are expected to hydrogen bond with each other, according to generally accepted base-pairing rules.

Detection/Identification of Genetic Variants in Expressed Polypeptides

Genetic variants present in polypeptides such as ADRB1, ADRB2, cytochrome P450 2D6 (CYP2D6), angiotensin converting enzyme (ACE), angiotensinogen, angiotensin receptor, renin, $Na^-$ channels (such as SCNN1A), adducin, sodium ($Na^+$) chloride ($Cl^-$) co-transporters (such as SLC12A3), and/or WNK1 can be detected by use of binding entities such as antibodies. Detection of specific differences in these polypeptides can be used to evaluate which blood pressure mediation is more effective.

Altered polypeptides can be detected in a selected fluid or tissue sample (e.g., cell scrapings, saliva, hair follicle, blood, skin tissue, or any convenient sample of a subject's nucleic acids). Any available methods for detecting polypeptides can be employed. Examples of such methods include immunoassay, Western blotting, enzyme-linked immunosorbant assays (ELISAs), radioimmunoassay, immunocytochemistry, immunohistochemistry, flow cytometry, immunoprecipitation, one- and two-dimensional electrophoresis, mass spectroscopy and/or detection of enzymatic activity.

Altered polypeptides can be detected by binding entities.

Antibodies and other binding entities can be used to detect genetic variants present in ADRB1, ADRB2, cytochrome P450 2D6 (CYP2D6), angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1 polypeptides. Such antibodies and binding entities can be prepared by available methods. For example, available amino acid sequences of non-variant and genetic variant ADRB1, ADRB2, CYP2D6, angiotensin converting enzyme (ACE), angiotensinogen, angiotensin receptors, renin, $Na^-$ channels (such as SCNN1A), adducin, sodium ($Na^+$) chloride ($Cl^-$) co-transporters (such as SLC12A3), and/or WNK1, including those illustrated herein, can be used to make antibodies and binding entities. Suitable antibodies may include polyclonal, monoclonal, fragments (such as Fab fragments), single chain antibodies and other forms of specific binding molecules. Briefly, these polypeptide detection assays can include contacting a test sample with an antibody specific to the genetic variant site in the polypeptide, detecting the presence of a complex between the antibody and the polypeptide. In some embodiments, a signal from the polypeptide-antibody complex is detected.

Such antibody-based detection methods can any convenient immuno-detection method such as Western Blot, ELISA, radioimmunoassay, immunocytochemistry, immunohistochemistry, flow cytometry, and immunoprecipitation.

Antibodies can be used to detect or identify the presence of genetic variant forms of ADRB1, ADRB2, CYP2D6, angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1 polypeptides in a sample. The antibodies are specific for sites of genetic variations, and exhibit substantially no (or significantly less) binding to similar polypeptides that do not have the same genetic variation(s).

Generally speaking, such antibodies can be employed in any type of immunoassay, so long as the genetic variations in the polypeptides are reliably identified. This includes both the two-site sandwich assay and the single site immunoassay of the non-competitive type, as well as in traditional competitive binding assays.

For example, in a typical forward sandwich assay, unlabeled antibody is immobilized on a solid substrate, e.g., within microtiter plate wells, and the sample to be tested is brought into contact with the bound molecule. After a suitable period of incubation, for a period of time sufficient to allow formation of an antibody-antigen binary complex, a second antibody, labeled with a reporter molecule capable of emitting or inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantified by comparison with a control sample containing known amounts of antigen.

Variations on the forward sandwich assay include the simultaneous assay, in which both sample and antibody are added simultaneously to the bound antibody, or a reverse sandwich assay in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique.

For the sandwich assays, the only limiting factor is that both antibodies have different binding specificities for the genetic variant polypeptide. Thus, a number of possible combinations are possible. For example, a primary antibody can bind specifically to the variant epitope of one of the variant polypeptides. A secondary antibody can bind to a different site on the genetic variant polypeptide. As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay.

Conventional antibody binding processes can be employed. Following binding, the solid phase-antibody complex is washed in preparation for the test sample. An aliquot of the test sample is then added to the solid phase complex and incubated at about 25° C. for a period of time sufficient to allow binding of any genetic variant polypeptides present to the antibody. The primary antibody can bind specifically to the site of the genetic variant (e.g., the region of a variant amino acid and/or the structural changes associated therewith), but not to similar polypeptides that have no such genetic variant. After washing off unbound antibodies, the second antibody is then added to the solid phase complex and incubated at 25° C. for an additional period of time sufficient to allow the second antibody to bind to the primary antibody-antigen solid phase complex (e.g., to a different site on the genetic variant polypeptide than is bound by the primary antibody). The second antibody may be linked to a reporter molecule, the visible signal of which is used to indicate the binding of the second antibody to any antigen in the sample.

As used herein, a "reporter molecule" or "label" is a molecule that provides an analytically detectable signal, allowing the detection of antigen-bound antibody. In some embodiments, detection is preferably at least relatively quantifiable, to allow determination of the amount of antigen in the sample, this may be calculated in absolute terms, or may be done in comparison with a standard (or series of standards) containing a known normal level of antigen. The term "label" is used interchangeably with "reporter molecule."

Many commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labeled antibody is added to the first antibody-antigen complex and allowed to bind to the complex, and then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantified, usually spectrophotometrically, to give an evaluation of the amount of antigen that is present in the serum sample.

Additionally, fluorescent compounds, such as fluorescein or rhodamine, may be chemically coupled to antibodies without altering their binding capacity. When activated by illumination with light of a particular wavelength, the fluorophore-labeled antibody absorbs the light energy, inducing a state of excitability in the molecule, followed by emission of the light at a characteristic longer wavelength. The emission appears as a characteristic color visually detectable with a light microscope. As in the enzyme immunoassay (EIA), the fluorescent-labeled antibody is allowed to bind to the first antibody-tagged polypeptide complex. After washing the unbound reagent, the remaining ternary complex is then exposed to light of the appropriate wavelength, and the fluorescence observed indicates the presence of the antigen.

Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

In another embodiment, the sample to be tested may be used in a single site immunoassay wherein it is adhered to a solid substrate either covalently or non-covalently. An unlabeled antibody is brought into contact with the sample bound on the solid substrate. After a suitable period of incubation, for a period of time sufficient to allow formation of an antibody-antigen binary complex a second antibody, labeled with a reporter molecule capable of inducing a detectable signal is then added and incubation is continued allowing sufficient time for the formation of a ternary complex of antigen-antibody-labeled antibody. For the single site immunoassay, the second antibody may be a general antibody (i.e., xenogeneic antibody to immunoglobulin, particularly anti-(IgM and IgG) linked to a reporter molecule) that is capable of binding an antibody that is specific for the genetic variant polypeptide of interest.

Kits

Another aspect of the invention is one or more kits for evaluating blood pressure from a test sample provided by, or obtained from, a subject.

The kits can include any reagents, components and instructions useful for testing, assaying, detecting, identifying, and % or determining whether genetic variations are present in ADRB1, ADRB2, CYP2D6, angiotensin converting enzyme (ACE), angiotensinogen, angiotensin receptors, renin, $Na^+$ channels (such as SCNN1A), adducin, sodium ($Na^+$) chloride (CI) co-transporters (such as SLC12A3), and/or WNK1 polypeptides or nucleic acids that can be present in the test samples.

The kits can include reagents, components and instructions for detecting, identifying, and/or quantifying such polypeptides or nucleic acids. For example, the kits may include primers, probes, labels, enzymes and/or other components for detecting, and/or identifying genetic variations in such polypeptides or nucleic acids.

In other embodiments, the kits may include one or more antibody preparations that selectively bind to genetic variant ADRB1, ADRB2, CYP2D6, angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1 polypeptides, and a detection means for detecting an antibody complex that can form (e.g., a label or reporter molecule that is either bound to an antibody or is capable of binding to the antibody).

One type of kit can include components for obtaining a sample from a subject, and instructions for sample collection. For example, such a sample collection kit can include one or more containers for sample collection such as one or more vials, test tubes, or receptacles. The sample collection containers can include a solution for stabilizing samples placed in the containers. Such a stabilizing solution can include protease inhibitors, nuclease inhibitors, DNase inhibitors, RNase inhibitors, chelators, denaturants, salts, salts, and/or buffers. The sample collection kit can also include components for sample collection such as swabs, droppers, syringes, needles, scalpels, and/or catheters. The instructions can include steps for sample collection, storage of the sample, and submission of the sample.

The kits can include one or more probes and/or primers each capable of specifically binding to a nucleic acid segment of at least 13, 14, 15, 16, 17, 18, 19, 20, or 25 nucleotides. In some embodiments, probes and/or primers are each capable of specifically binding to a nucleic acid segment of 15-30, 15-40, 15-50 nucleotides, or any number of nucleotides between 13-50 nucleotides, in a target DNA or RNA. The probes may be part of an array, microarray, microchip, assay plate, or nanochip. Alternatively, the probes or primers may be packaged separately and/or individually. In some embodiments, the probes or primers may be detectably labeled. For example, labels can be included on immobilized probes, where the label signals are quenched until hybridization occurs and then, upon hybridization, the label emits a detectable signal. Alternatively, one or more labels can be included in the kit that can bind to a hybridized complex between a probe and a target DNA or RNA.

Additional reagents can be included in the kits. For example, the kits may also contain reagents for detecting or identifying a genetic variant in an ADRB1, ADRB2, CYP2D6, angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1 nucleic acid in a test sample. Such reagents can include reagents for isolating, storing and detecting nucleic acids. For example, the kits can include reagents and enzymes for nucleic acid amplification, primer extension, RNA reverse transcription, sequencing, restriction enzyme cleavage, and/or separation of nucleic acids. The kits may also include reagents such as solutions for stabilizing nucleic acids, solutions for purifying nucleic acids, nucleotide triphosphates, buffers, and/or other reagents that can be used in a test tissue sample.

Preservatives and/or antimicrobial agents can be included to stabilize reagents and prevent contamination, such as, for example, paraben, chlorobutanol, phenol sorbic acid, and the like.

It may also be desirable to include agents such as solvents for nucleic acids, reducing agents (e.g., beta-mercaptoethanol), stabilizing reagents (e.g., reagents for inhibiting nucleases, ribonucleases, disrupting tissues, precipitating nucleic acids, and the like).

In further embodiments, the kits can include a computer program product for use in conjunction with a computer system and the methods described herein. A computer program mechanism can be embedded in the computer program product. The computer program product can, for example, be a device with a computer program mechanism encoded thereon, where the computer program mechanism may be loaded into the memory of a computer and cause the computer to carry out at least one step of a method for assessing the malignant/benign status of a test thyroid tissue sample. For example, the device can be a computer readable storage medium, a flash memory, a compact disc (CD), a digital versatile disc, digital video disc, or an article of manufacture that tangibly includes one or more computer programs and memory storage. In some embodiments, the computer program product can be a computer readable storage medium. In such kits, the computer program mechanism can include instructions for determining, detecting, and/or identifying a genetic variant in an ADRB1, ADRB2, CYP2D6, angiotensin converting enzyme (ACE), angiotensinogen, angiotensin receptors, renin, $Na^+$ channel (such as SCNN1A), adducin, sodium ($Na^+$) chloride ($Cl^-$) co-transporter (such as SLC12A3), and/or WNK1 nucleic acid or polypeptide in a test sample.

In other embodiments, the kits can include a system, such as a computer, having a central processing unit and a memory coupled to the central processing unit. The memory may store instructions for determining, detecting, and/or identifying a genetic variant in an ADRB1, ADRB2, CYP2D6, angiotensin converting enzyme (ACE), angiotensinogen, angiotensin receptors, renin, $Na^+$ channel (such as SCNN1A), adducin, sodium ($Na^+$) chloride ($Cl^-$) co-transporter (such as SLC12A3), and/or WNK1 nucleic acid or polypeptide in a test sample. The memory can also store therapeutic options for different genotyping results.

The kits can also include one or more therapeutic agents, for example, any blood pressure medications described herein.

Definitions

Some definitions are provided below; other definitions are provided in the other sections of the applications.

As used herein, "obtaining a test sample" involves removing a sample of tissue from a patient, receiving a sample of tissue from a patient, receiving a patient's tissue sample from a physician, receiving a patient's tissue sample via mail delivery and/or removing a patient's tissue sample from a storage apparatus (e.g., a refrigerator or freezer) or a facility. Thus, obtaining a test sample can involve removal or receipt of the test sample directly from the patient, but obtaining a test sample can also include receipt of a test sample indirectly from a medical worker, from a storage apparatus/facility, from a mail delivery service after transportation from a medical facility, and any combination thereof. The test sample can therefore originate in one location, and be transported to another location where it is received and tested. Any of these activities or combinations of activities involves "obtaining a test sample."

As used herein a probe refers to a single DNA or RNA molecule (a nucleic acid oligomer) or a collection of nucleic acid molecules (nucleic acid oligomers) where the DNA molecules have at least one segment with a sequence that is complementary to a region of a target nucleic acid. The probe can hybridize with the target nucleic acid under stringent conditions. In some cases, the probe can hybridize with the target nucleic acid under highly stringent conditions. The probe is not identical to naturally available nucleic acids because has additional components such as one or more labels, one or more (engineered) restriction sites, one or more molecular barcodes, one or more tags for identification or retrieval of the probe (e.g., with or without the target hybridized thereto). In some instances the probe is attached to a solid surface such as a chip, an array, a bead, or other surface.

As used herein a primer contains a region that is designed to hybridize to a targeted locus (e.g., a targeted polymorphic locus or a nonpolymorphic locus). The primer and may contain a priming sequence designed to allow PCR amplification. The primer can have at least one segment with a sequence that is complementary to a region of a target nucleic acid. The primer can hybridize with the target nucleic acid under stringent conditions. In some cases, the primer can hybridize with the target nucleic acid under highly stringent conditions. The primer is not identical to naturally available nucleic acids because has additional components such as a molecular barcode, a tag, an engineered restriction site, or a combination thereof. A primer may contain a random region that differs for each individual molecule. The terms "test primer" and "candidate primer" are not meant to be limiting and may refer to any of the primers disclosed herein.

As used herein a "binding entity" is a molecule or molecular complex that can recognize and bind to selected target molecules. Such binding entities can be antibodies or any molecule that has a binding domain for a target molecule.

A number of proteins can serve as protein scaffolds to which binding domains for targets can be attached and thereby form a suitable binding entity. The binding domains bind or interact with the targets of the invention while the protein scaffold merely holds and stabilizes the binding domains so that they can bind. A number of protein scaffolds can be used. For example, phage capsid proteins can be used. See Review in Clackson & Wells, Trends Biotechnol. 12:173-184 (1994). Phage capsid proteins have been used as scaffolds for displaying random peptide sequences, including bovine pancreatic trypsin inhibitor (Roberts et al., PNAS 89:2429-2433 (1992)), human growth hormone (Lowman et al., Biochemistry 30:10832-10838 (1991)), Venturini et al., Protein Peptide Letters 1:70-75 (1994)), and the IgG binding domain of *Streptococcus* (O'Neil et al., Techniques in Protein Chemistry V (Crabb, L, ed.) pp. 517-524, Academic Press, San Diego (1994)). These scaffolds have displayed a single randomized loop or region that can be modified to include binding domains for selected targets.

Researchers have also used the small 74 amino acid α-amylase inhibitor Tendamistat as a presentation scaffold on the filamentous phage M13. McConnell, S. J & Hoess, R. H., J. Mol. Biol. 250:460-470 (1995). Tendamistat is a β-sheet protein from *Streptomyces tendae*. It has a number of features that make it an attractive scaffold for binding peptides, including its small size, stability, and the availability of high resolution NMR and X-ray structural data. The overall topology of Tendamistat is similar to that of an immunoglobulin domain, with two β-sheets connected by a series of loops. In contrast to immunoglobulin domains, the β-sheets of Tendamistat are held together with two rather than one disulfide bond, accounting for the considerable stability of the protein. The loops of Tendamistat can serve a similar function to the CDR loops found in immunoglobulins and can be easily randomized by in vitro mutagenesis. Tendamistat is derived from *Streptomyces tendae* and may be antigenic in humans. Hence, binding entities that employ Tendamistat are preferably employed in vitro.

Fibronectin type III domain has also been used as a protein scaffold to which binding entities can be attached. Fibronectin type III is part of a large subfamily (Fn3 family or s-type Ig family) of the immunoglobulin superfamily. Sequences, vectors and cloning procedures for using such a fibronectin type III domain as a protein scaffold for binding entities (e.g. CDR peptides) are provided, for example, in U.S. Patent Application Publication 20020019517. See also, Bork, P. & Doolittle, R. F. (1992) Proposed acquisition of an animal protein domain by bacteria. Proc. Natl. Acad. Sci. USA 89, 8990-8994; Jones, E. Y. (1993) The immunoglobulin superfamily Curr. Opinion Struct. Biol. 3, 846-852; Bork, P., Hom, L. & Sander, C. (1994) The immunoglobulin fold. Structural classification, sequence patterns and common core. J. Mol. Biol. 242, 309-320; Campbell, I. D. & Spitzfaden, C. (1994) Building proteins with fibronectin type III modules Structure 2, 233-337; Harpez, Y. & Chothia, C. (1994).

The following non-limiting examples further illustrate aspects of the invention.

Example 1: Sample Processing

Each patient is given a collection kit consisting of two buccal swabs and two uniquely barcoded tubes (termed A and B swabs) containing a proprietary lysis buffer consisting of 50 mM Tris pH 8.0, 50 mM EDTA, 25 mM Sucrose, 100 mM NaCl, and 1% SDS. The patient will use the swab to collect buccal cells by scraping the inside of their cheek and place the swab in the provided barcoded tube, one swab for each cheek. Once the swab has been placed into the lysis buffer the cells are no longer viable and therefore samples are now considered to be nucleic acids and safe to be shipped via standard mail. All samples are checked-in. The barcodes of the samples are scanned and their arrival in the laboratory is confirmed.

Figure 3A:
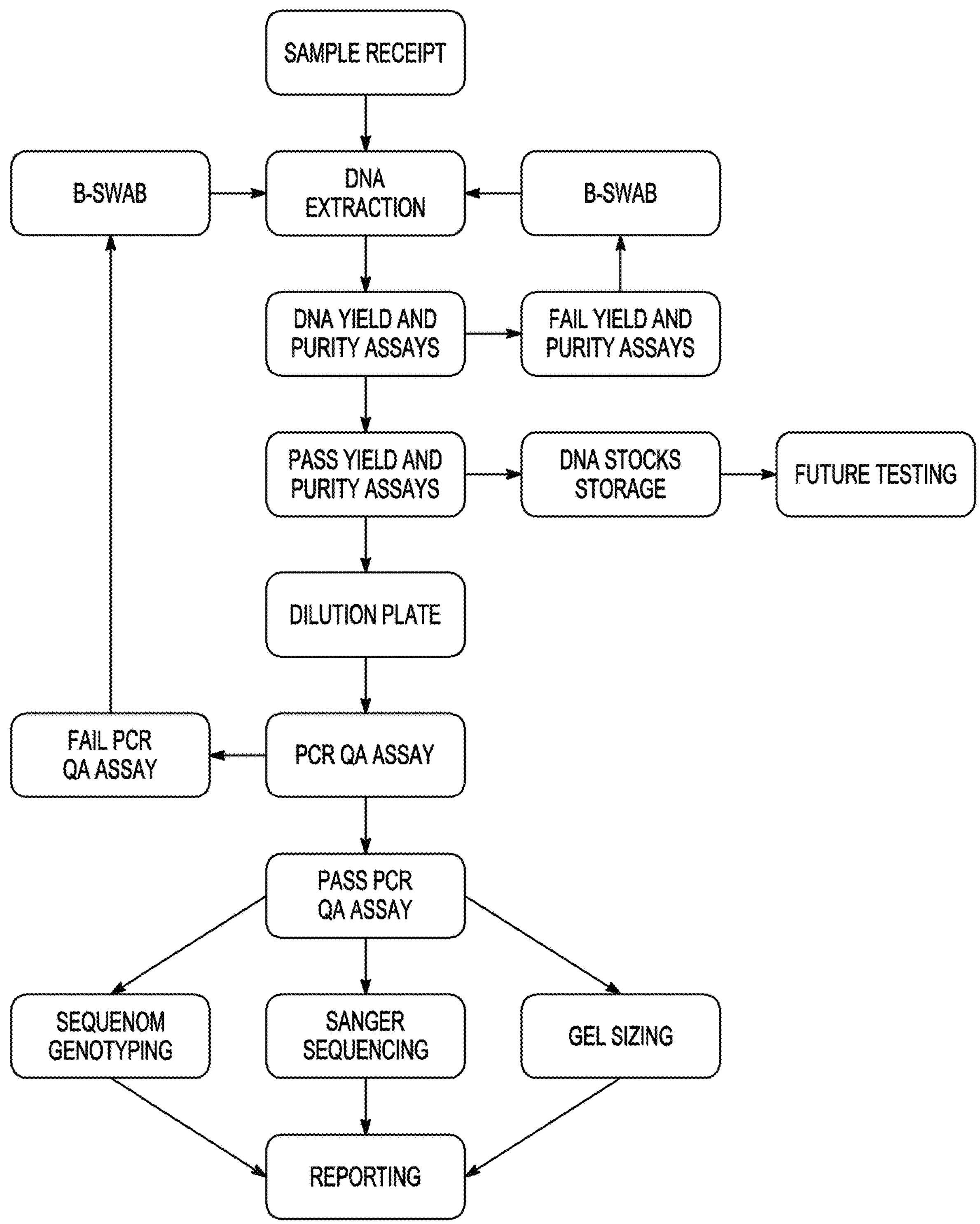
FIG. 3A-3B are schematic diagrams illustrating processing of test samples. For example, each subject can collect two swabs. The A swab can collect cell material from the inside of the right cheek, while the B swab can collect cell material from the left cheek. For FIG. 3A, the A swab can be the initial swab entered into the process (from DNA Extraction to Reporting). If the A swab fails, during DNA Yield and Purity Analysis. Genetic analysis, or the PCR QA Assay then the B swab can be entered into the system as illustrated.
Figure 3B:
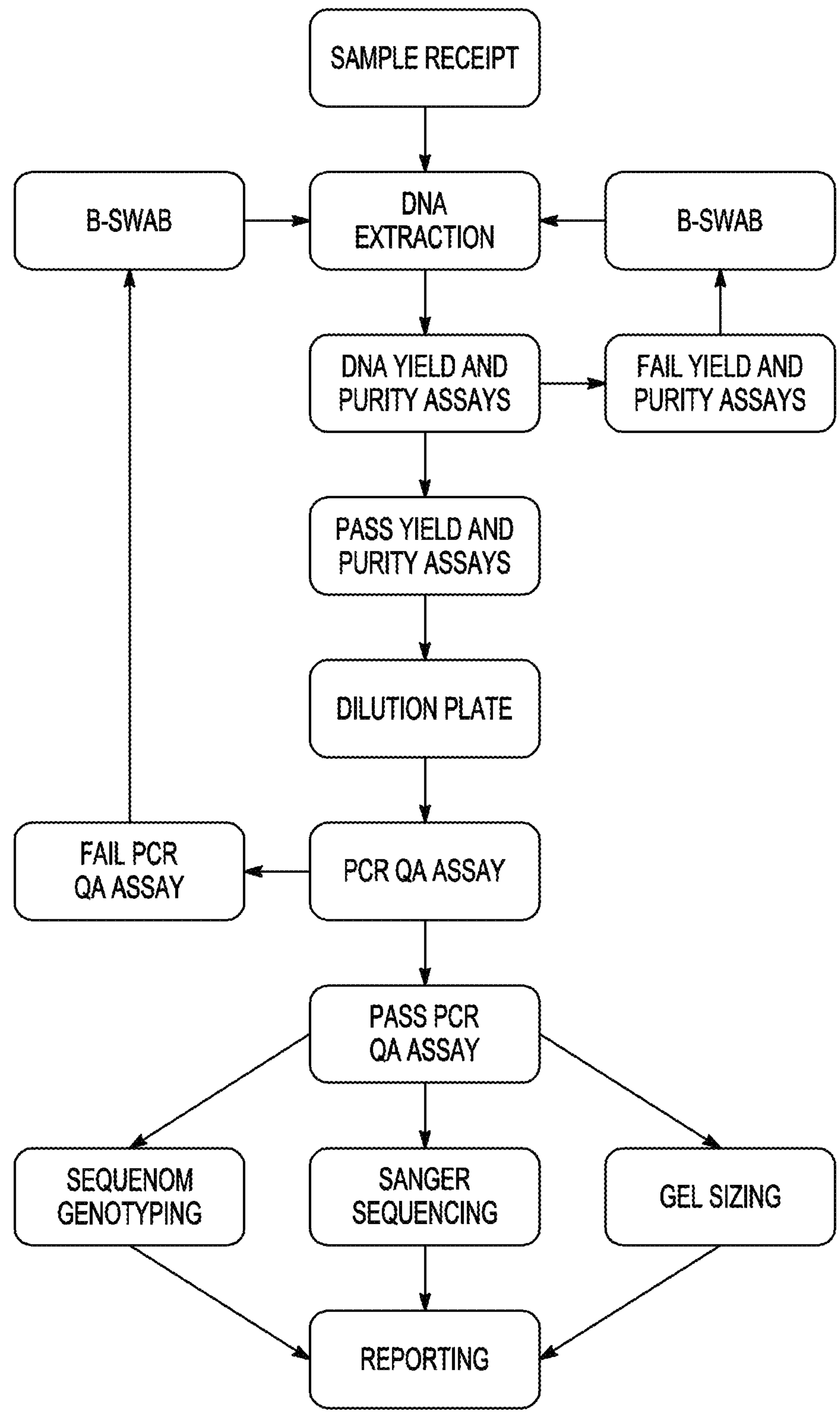
Figure 4:
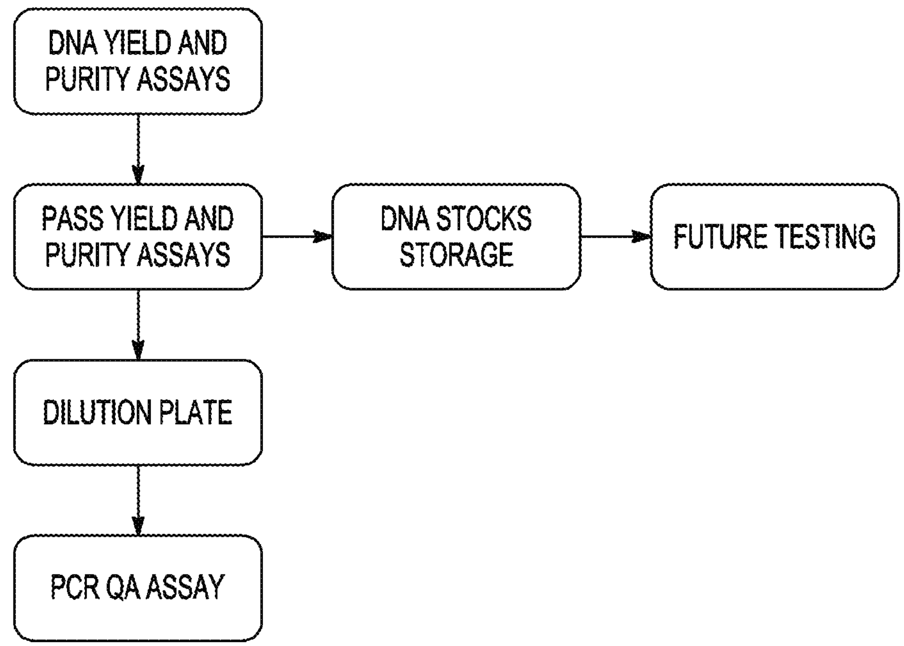
FIG. 4 is a schematic diagram illustrating handling of DNA samples.
Figure 5:
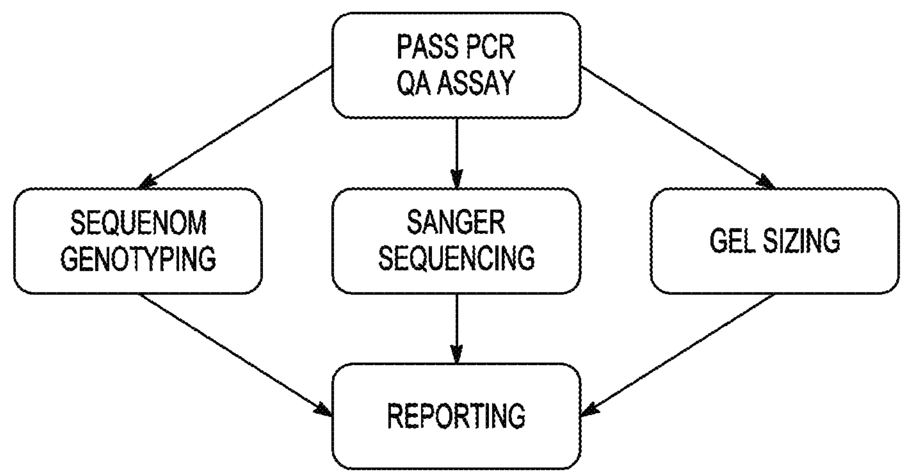
FIG. 5 is a schematic diagram illustrating processing of the sample after PCR amplification.

FIGS. 3A-3B show schematic diagrams illustrating slight variations in sample processing. In general, two samples (Swab A and Swab B) are taken. The Swab A sample is subjected to the process (DNA Extraction through Reporting) unless the Swab A sample fails either the DNA Yield and Purity Assays, Genomic Analysis, or the PCR QA Assay. If such failure occurs, then the other sample (Swab B) is subjected to the process, as illustrated in FIGS. 3A and/or 3B.

The samples are grouped into sets of 91 and assigned positions in 96 sample grids (12×8 grid layout) for DNA extraction. The remaining five positions in each grid can be extraction controls (four negative controls [$H_2O$] and one non-human positive). The five controls can be assigned random positions in each grid, giving each grid/plate a unique "plate fingerprint." The randomly assigned controls prevent possible plate swaps or 180° rotations as every plate is now identifiable simply by control positions. All samples are then normalized to a volume of 650 ul by addition of the above mentioned lysis buffer. Additionally, 25 ul of proteinase K (ProK) is added and each sample is incubated in a 55° C. oven for a minimum of 4 hours.

Following such incubation, the samples are extracted using a BioSprint96 (KingFisher96) Robotic workstation with magnetic-particle DNA purification chemistry to isolate genomic DNA (GenomicDNA) from tissue samples. This protocol utilizes the chemistry from the eVoMagDNA Extraction KF96 Kit (Verde Labs, Marietta, Ga.) and is run to specifications provided by the manufacturer.

Following DNA extraction and subsequent desiccation, the DNA is resuspended in HPLC water. Five microliters of each sample is then aliquoted to assay plates for the first pair of QA assays, both a PicoGreen fluorometric quantification and a spectrophotometric purity estimation. The fluorescence and absorbance data is analyzed for all samples in the 96 well plate, including the five controls. The positions of the negative controls is confirmed and accessed for possible plate contamination. The results for the positive control as well as the samples on the plate are analyzed for quality metrics using a systems analysis approach. The outliers are statistically assessed. After the quantification and purity evaluations, QA assay robotic systems are used to transfer the samples into racks of 96 sample septa sealed plates (to ensure there is no evaporative loss) and a fractional volume of each sample is used to create a daughter plate of the samples at a normalized concentration of 5 ng/μl for the PCR QA assays and subsequent genotyping. The creation of the normalized daughter plate serves two purposes. First, it allows the immediate storage of the primary stock of each sample at −80° C. avoiding the need for unnecessary freeze-thaw of samples and the potential contamination risks associated with repeated accessing of the stock. Second, it avoids unnecessary waste of the DNA associated with the use of full concentration stock for the PCR applications (this −80° C. stock DNA can be used at any time or saved for future testing).

Any samples that fail any of the QA assays can re-enter the pipeline and be sorted and re-processed from the B-swab, which is the second tube/swab in the kit sent to the customer mentioned above. By always having a backup sample it is not necessary to go back to the customer to ask for a re-swab. If the quantity and purity are still insufficient then whole genome amplification and/or organic re-extraction can be employed.

Following the passage of the QA thresholds normalized fractions of the samples are transferred to PCR plates for genotyping. Each sample is analyzed using three different methodologies, the Sequenom MassArray genotyping platform, Sanger sequencing using the ABI 3730xl genomic analyzer from Applied Biosystems, and classical PCR and gel sizing to determine insertion/deletion status. The Sequenom MassArray genotyping platform is used to analyze the following SNP sites: rs1042713, rs1042714, rs1159744, rs12750834, rs1801252, rs1801253, rs2107614, rs227869, rs4244285, rs4961, and rs699. Sanger sequencing is used to analyze the following SNPs: rs3892097, rs3758581, rs2228586, and rs5186. Finally classical gel sizing is used to determine the insertion/deletion status of the rs1799752 SNP.

Example 2: Sequenom MassArray Assay Design and Processing

The Sequenom platform is able to perform genotyping as a twelve-plex assay (testing 12 variable sites in one reaction) in a 96 well format using one aliquot of DNA. The AssayDesign software from Sequenom is used to generate both PCR and single base extension primers using the individual rs number of each variable site to create the final assay design. Table 1 shows examples of primers that can be used to detect various single nucleotide polymorphisms.

TABLE 1

Primers for Amplification of Nucleic Acid Variant Segments

| SNP ID | 2nd PCRP | SEQ ID | 1st PCRP | SEQ ID |
|---|---|---|---|---|
| rs1042714 | ACGTTGGATGAGACATGACGATGCCCATGC | NO: 36 | ACGTTGGATGAGCGCCTTCTTGCTGGCAC | NO: 37 |
| rs699 | ACGTTGGATGCTGTGACAGGATGGAAGACT | NO: 38 | ACGTTGGATGTGGACGTAGGTGTTGAAAGC | NO: 39 |
| rs4961 | ACGTTGGATGTGTTCGTCCACACCTTAGTC | NO: 40 | ACGTTGGATGACAAGATGGCTGAACTCTGG | NO: 41 |
| rs12750834 | ACGTTGGATGGGAATCCAGGAGAATAGGTC | NO: 42 | ACGTTGGATGACAGGCTACCTGGCTTTAAC | NO: 43 |
| rs1801252 | ACGTTGGATGGCCTCGTTGCTGCCTCCCG | NO: 44 | ACGTTGGATGATCAGCAGACCCATGCCCG | NO: 45 |
| rs1801253 | ACGTTGGATGAGCCCTGCGCGCGCAGCA | NO: 46 | ACGTTGGATGTCAACCCCATCATCTACTGC | NO: 47 |
| rs227869 | ACGTTGGATGCTGACATTGCCAGCTGTATC | NO: 48 | ACGTTGGATGGTAGTGGCACTGGCATATTC | NO: 49 |
| rs2107614 | ACGTTGGATGGCAACCATCACAGTACTAAG | NO: 50 | ACGTTGGATGCACAACTGGAAGAGTTGAGG | NO: 51 |
| rs1529927 | ACGTTGGATGTGGACCCCATTAACGACATC | NO: 52 | ACGTTGGATGTCACCTTGGACTCCCACTC | NO: 53 |
| rs4244285 | ACGTTGGATGCACTTTCCATAAAAGCAAGG | NO: 54 | ACGTTGGATGGCAATAATTTTCCCACTATC | NO: 55 |
| rs1042713 | ACGTTGGATGATGAGAGACATGACGATGCC | NO: 56 | ACGTTGGATGGAACGGCAGCGCCTTCCTG | NO: 57 |
| rs1159744 | ACGTTGGATGGAAACAGTGACAGCCAAATG | NO: 58 | ACGTTGGATGGTTTTTCAGTTCCTGAATTTG | NO: 59 |

DNA samples at a concentration of 5 ng/ul undergo a PCR using the above designed PCR primers and the Sequenom iPLEX Gold Reagent kit under the conditions described in Table 2.

TABLE 2

PCR Reaction Mixture

| Reagent | Final Concentration | Vol/rxn (uL) |
|---|---|---|
| Water, HPLC | n/a | 1.8 |
| 10x PCR Buffer with 20 mM $MgCl_2$ | 2 mM $MgCl_2$ | 0.5 |
| 25 mM $MgCl_2$ | 2 mM | 0.4 |
| 25 mM dNTP Mix | 500 uM | 0.1 |

TABLE 2-continued

| PCR Reaction Mixture | | |
|---|---|---|
| Reagent | Final Concentration | Vol/rxn (uL) |
| 0.5 mM Primer Mix | 0.1 uM | 1 |
| 5 U/uL PCR Enzyme | 1 unit | 0.2 |
| Volume | | 4 |
| 10 ng/uL DNA | 10 ng/rxn | 1 |
| Total Volume | | 5 |

The PCR reaction cycling conditions can be as illustrated in Table 3.

TABLE 3

| PCR Reaction Cycling<br>Cycler Program iPlex- PCR | | |
|---|---|---|
| Temp (° C.) | Time (min) | |
| 95 | 2:00 | |
| 95 | 0:30 | Repeat |
| 56 | 0:30 | 45 |
| 72 | 1:00 | Cycles |
| 72 | 5:00 | |
| 4 | ∞ | |

Directly following PCR amplification, excess primers and deoxynucleotide triphosphates are removed via a SAP (shrimp alkaline phosphatase) reaction under the conditions described in Table 4.

TABLE 4

| PCR Clean-Up | | |
|---|---|---|
| Reagent | Final Concentration | Vol/rxn (uL) |
| Water, HPLC | N/A | 1.53 |
| SAP Buffer (10x) | 0.24x | 0.17 |
| 5 U/uL PCR Enzyme | 1 unit | 0.2 |
| Volume | | 2 |
| PCR product | | 5 |
| Total Volume | | 7 |

The Shrimp Alkaline Phosphatase reaction is incubated at 37° C. for 40 min, followed by incubation at 85° C. for 5 min. The samples can be stored at 4° C. indefinitely.

After the SAP reaction is completed the samples can be subjected to single base extension reactions using the primers described in Table 5, and the conditions described in Table 6 and 7.

TABLE 5

| Single Base Extension Primers | | |
|---|---|---|
| SNP | Sequence | SEQ ID NO: |
| rs1042714 | ACACCTCGTCCCTTT | 60 |
| rs699 | CTGGCTGCTCCCTGA | 61 |
| rs4961 | ACTGCTTCCATTCTGCC | 62 |
| rs12750834 | AGTCTCTGTAAGTGCCC | 63 |
| rs1801252 | GTGCCTCCCGCCAGCGAA | 64 |
| rs1801253 | CGCGCGCAGCAGAGCAGT | 65 |

TABLE 5-continued

| Single Base Extension Primers | | |
|---|---|---|
| SNP | Sequence | SEQ ID NO: |
| rs227869 | AGCTGTATCTGCTCCATTCA | 66 |
| rs2107614 | TCCTCCAAAAAAAAAGAAAAC | 67 |
| rs1529927 | GTTACCGACATCCGCATCATTG | 68 |
| rs4244285 | TAAGTAATTTGTTATGGGTTCC | 69 |
| rs1042713 | GGAGGGGTCCGGCGCATGGCTTC | 70 |
| rs1159744 | CAAATGTTAACAGTATAGAAAATTTTA | 71 |

TABLE 6

| Single Base Extension Reaction Conditions | | |
|---|---|---|
| Reagents | Final Concentration | Vol/rxn(uL) |
| Water, HPLC | N/A | 0.619 |
| iPlex Gold Buffer | 0.222x | 0.200 |
| iPlex Termination Mix | 1x | 0.200 |
| iPlex Extend Primer Mix | varies | 0.940 |
| iPlex Enzyme | 1x | 0.041 |
| Volume | | 2.000 |
| PCR product | | 7 |
| Total Volume | | 9 |

TABLE 7

| Single Base Extension Reaction Cycling conditions | | | |
|---|---|---|---|
| Temp (∞ C.) | Time (min) | | |
| 94 | 0:30 | | |
| 94 | 0:05 | | 40 cycles |
| 52 | 0:05 | 5 cycles | ↓ |
| 80 | 0:05 | ↓ | |
| 72 | 3:00 | | |
| 4 | forever | | |

After completion of all of the above reactions, the samples are run through resin based clean-up to remove excess salts according to standard Sequenom protocols. The samples are then spotted onto the Sequenom provided SpectroChip using the Sequenom Nanodispenser according to manufacturer protocols and subsequently processed on the Sequenom MALDI-TOF platform.

A sample results report is provided in Table 7. The two letters for each polymorphism type are for the two alleles present in the subjects, illustrating that the subjects are homozygous for some polymorphisms (e.g., subject GCE0104 is homozygous (G/G) for the variable site in the rs1042713 polymorphism, but subject GCE0120 is heterozygous (GA) for that site).

TABLE 8

| Results | | |
|---|---|---|
| SNP | GCE0120 | GCE0104 |
| rs1042713 | GA | GG |
| rs1042714 | GC | GG |

TABLE 8-continued

| Results | | |
|---|---|---|
| SNP | GCE0120 | GCE0104 |
| rs1159744 | AA | AT |
| rs12750834 | GA | GG |
| rs1529927 | GG | GG |
| rs1801252 | AA | AA |
| rs1801253 | GG | GG |
| rs2107614 | CT | TT |
| rs227869 | AA | AG |
| rs4244285 | GG | GA |
| rs4961 | GG | GG |
| rs699 | CG | GG |

Example 3: Sanger Sequencing Primer Design and Workflow

All primers for Sanger sequencing were designed using the free, web-based primer design tool Primer3. 500 base pairs of flanking sequence for each SNP (single nucleotide polymorphism) were entered into Primer3. The top primer candidate for each site was chosen and optimized using a buffer panel with varying MgCl concentrations and a temperature gradient to determine the optimal cycling conditions for each primer pair.

TABLE 9

| Primers for Sequencing of SNPs | | | |
|---|---|---|---|
| Primer Name | Sequence | SEQ ID | Purpose |
| rs3892097_F | TTCAGTCCCTCCTGAGCTA | NO: 72 | SNP |
| rs3892097_R | AAGGTGGATGCACAAAGAG | NO: 73 | SNP |
| rs3758581_F | GTGCATCTGTAGCAGTCCTC | NO: 74 | SNP |
| rs3758581_R | CCAAACTGGAATCAACAGAA | NO: 75 | SNP |
| rs2228586_F | GAAGTGGTCTCGTCTAGCAA | NO: 76 | SNP |
| rs2228586_R | CAGAGAGAGAGGTCCCATTT | NO: 77 | SNP |
| rs5186_F | CCACTCAAACCTTTCAACAA | NO: 78 | SNP |
| rs5186_R | TGGACAGAACAATCTGGAAC | NO: 79 | SNP |

The region encompassing the SNP was amplified from sample nucleic acids by PCR using optimized individual cycling conditions for each SNP site. Directly after PCR amplification each sample is cleaned up using a size exclusion micro-filtration plate from Millipore and entered into the Sanger sequencing reaction. Each sample is sequenced in both the forward (3') and reverse (5') direction giving double conformation of the allelic state. These forward and reverse sequences from each patient are then aligned to the human reference sequence using the CLC DNA workbench program creating an alignment file from which the allele call is made and added to the final SNP call report.

Figure 6:
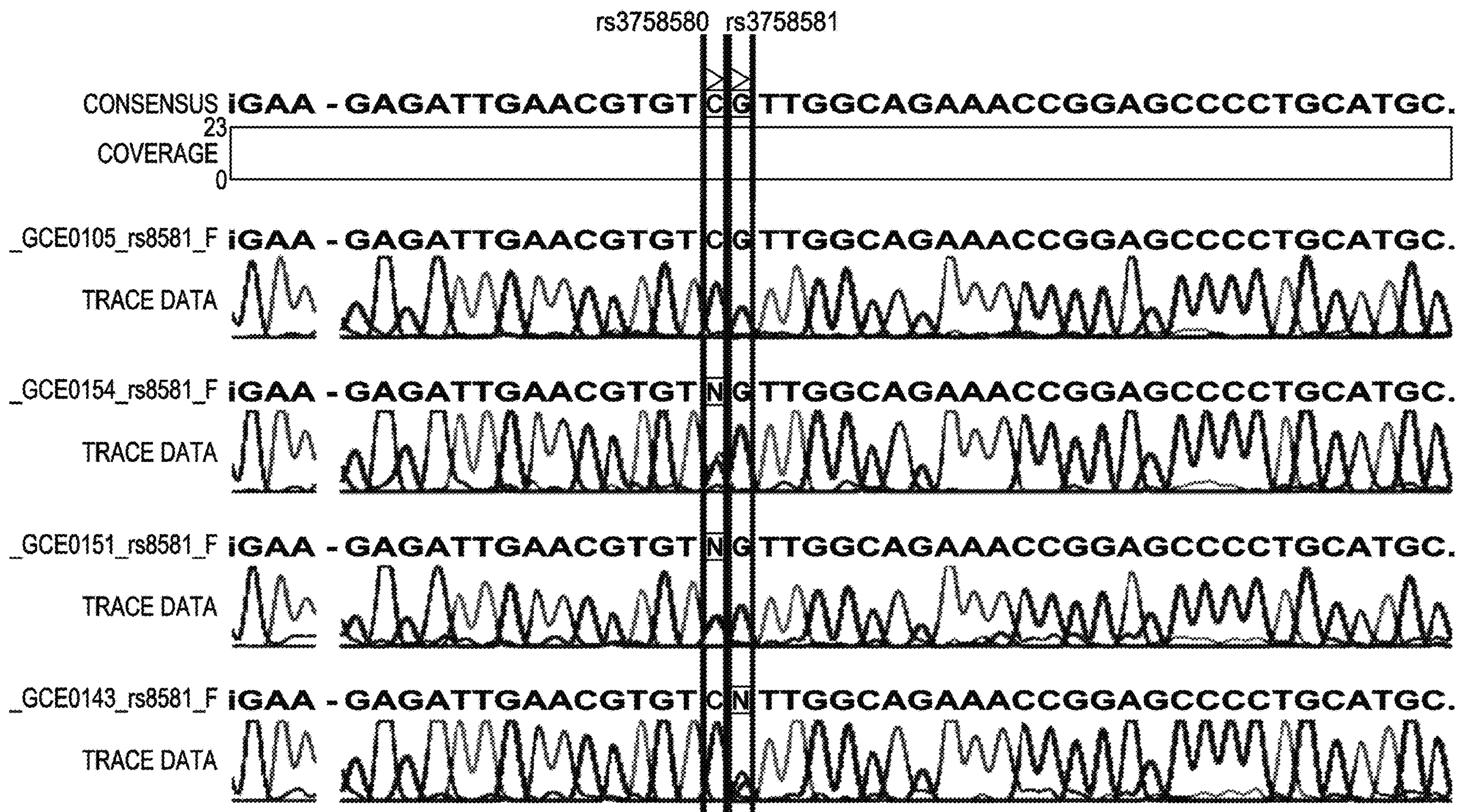
FIG. 6 illustrates alignment of sample results to a human reference sequence using the CLC DNA workbench program for creating an alignment file from which the allele call is made and added to the final SNP call report (SEQ ID Nos.: 82-85).

FIG. 6 illustrates the results from one such alignment.

Example 4: Gel Sizing Primer Design and Workflow

To accurately call the insertion % deletion status for site rs1799752, PCR amplification of sample nucleic acids is performed followed by gel electrophoresis. The PCR primers for this site were also designed and optimized using Primer3 and the above mentioned buffer and temperature gradient. The following primer sequences and PCR conditions were ultimately chosen:

TABLE 10

| Primer Sequences for PCR of rs1799752 Insertion/Deletion | | | |
|---|---|---|---|
| Primer Name | Sequence | SEQ ID | Purpose |
| rs1799752_F-2 | CCCATTTCTCTAGACCTGCT | NO: 80 | INDEL |
| rs1799752_R-2 | GGGATGGTGTCTCGTACATA | NO: 81 | INDEL |

Figure 7:
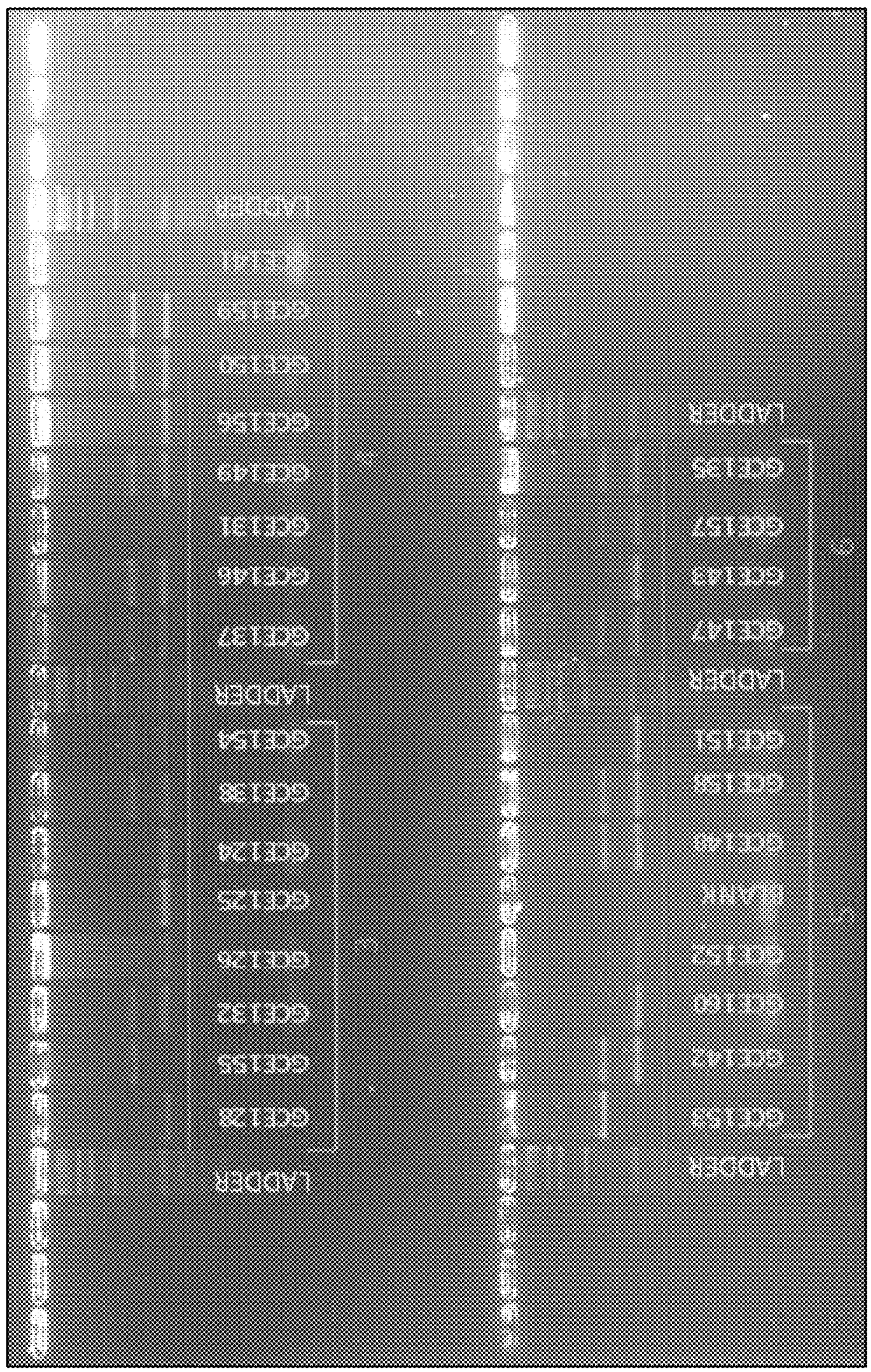
FIG. 7 is an example of 2% agarose gel used to score the presence or absence of a 288 bp ALU by visually examining the gel for either the higher molecular weight band (indicating the presence of the 288 bp ALU), the lower molecular weight band (indicating the absence of the 288 bp ALU), or both (indicating a heterozygous state).

Following PCR amplification, each sample is loaded into its own well of a 2% agarose gel and run at 150 mV for approximately 45 min and stained in a bath of GelRed for 2 hours prior to imaging with UV light. The resulting image is used to score the presence or absence of a 288 bp ALU visually by examining the gel for either the higher molecular weight band (indicating the presence of the 288 bp ALU), the lower molecular weight band (indicating the absence of the 288 bp ALU) or both (indicating a heterozygous state. A sample image of the gel is provided in FIG. 7.

Example 5: Genotyping Reports

Once all tests are performed a report is generated containing all results for each tested patient. One example of a report for subjects GCE0120 and GCE0104, is shown below. The two letters for each polymorphism type are for the two alleles present in the subjects, illustrating that the subjects are homozygous whereas other subjects are heterozygous for the variable site of each polymorphism.

TABLE 11

| Results from Analysis of Polymorphism | | |
|---|---|---|
| Polymorphism type | GCE0120 | GCE0104 |
| Sequenom Results | | |
| rs1042713 | GA | GG |
| rs1042714 | GC | GG |
| rs1159744 | CG | CG |
| rs12750834 | GA | GG |
| rs1529927 | GG | GG |
| rs1801252 | AA | AA |
| rs1801253 | GG | GG |
| rs2107614 | CT | TT |
| rs227869 | AA | AG |
| rs4244285 | GG | GA |
| rs4961 | GG | GG |
| rs699 | TT | TT |
| Sanger Sequencing Results | | |
| rs3892097 | CC | CC |
| rs3758581 | GG | GG |

TABLE 11-continued

| Results from Analysis of Polymorphism | | |
|---|---|---|
| Polymorphism type | GCE0120 | GCE0104 |
| rs3758580 | CC | CT |
| rs2228586 | TT | TT |
| rs5186 | AC | AA |
| Gel Results | | |
| rs1799752 | +/+ | +/- |

Example 6: Clinical Study Protocol

Clinical Protocol Summary

| | |
|---|---|
| Study Title: | Assessment of the Relationship between Genes that Encode Proteins Important in Blood Pressure Regulation and Blood Pressure Therapy in Patients with Hypertension. |
| Study Device: | The Geneticure Pharmacogenetic Testing Kit. The kit contains two buccal swabs with two buffer solution vials to stabilize DNA. These buccal swabs are used for DNA collection which is then extracted for analysis of genes important in high blood pressure. |
| Target Indication for Use: | The Geneticure Pharmacogenetic Testing Kit is a pharmacogenomic treatment decision support product that tests for clinically important genetic variants affecting a patient's response to antihypertensive medications. |
| Study Design: | This is a post-hoc association study of patients who have been diagnosed with high blood pressure and have been stable on medication treatment for at least 6 months. |
| Study Population: | To be enrolled in this study, subjects must meet ALL of the inclusion criteria and NONE of the exclusion criteria:<br>Inclusion Criteria<br>1. Subject is able and willing to provide informed consent<br>2. Subject is ≥30 and ≤70 years of age<br>3. Subject with diagnosis of Hypertension for a minimum of 1 year<br>4. Subject has been on the same class/classes of blood pressure medication for a minimum of 6 months. Note: A change in dosage, frequency, or specific medication is acceptable as long as there have been no changes to the class/classes of medications prescribed.<br>5. Subject with a Body Mass Index (BMI) ≥19 and ≤35<br>6. Subject is currently prescribed and taking one of the following classes of medications alone or in combination with each other or a Ca+ channel blocker.<br>Diuretics<br>ACE Inhibitors<br>Angiotensin Receptor Blocker (ARB)<br>Beta-blockers<br>Exclusion Criteria<br>1. Subject has clinically significant kidney disease as determined by the investigator.<br>2. Subject has clinically significant cardiac disease as determined by the investigator.<br>3. Subject has clinically significant vascular disease as determined by the investigator.<br>4. Subject has a diagnosis of secondary hypertension or is experiencing a complication of pregnancy.<br>5. Subject is currently prescribed and taking any additional class of medication(s) for high blood pressure not included in the list above, with the exception of a Ca+ channel blocker.<br>6. Subject has Systolic BP >190 or Diastolic BP >120 documented within the six months prior to visit.<br>7. Subject has a regular alcohol intake of greater than 21 units per week in the past 6 months<br>8. Subject has smoked greater than two packs of cigarettes (total) or equivalent nicotine intake in the past 6 months.<br>9. Subject has an anticipated survival less than 12 months.<br>10. Any other reason that the subject is inappropriate for study enrollment in the opinion of the Investigator. |
| Primary Study Objective: | To assess the relationship between the drug therapy class/combination of therapy classes that resulted in the best blood pressure control for a patient vs. what the Geneticure high blood pressure panel would have predicted. |
| Secondary Study Objectives: | To assess the clinical time to achieve optimal blood pressure treatment.<br>To assess the number of office visits required to achieve optimal blood pressure treatment. |

1 Introduction

Hypertension (high blood pressure) is one of the most important preventable contributors to disease and death in the United States and represents the most common condition seen in the primary care setting (The sixth report of the Joint National Committee on prevention, detection, evaluation, and treatment of high blood pressure. Arch Intern Med. 157(21):2413-2446 (1997); Chobanian et al. JAMA 289(19): 2560-2572 (2003)). According to the American Heart Association, approximately 78 million adults (1 in 3) living in the United States have hypertension with more than 5 million new diagnoses made each year (American Heart Association. Heart and Stroke Statistics—2004 Update. Paper presented at: Dallas: American Heart Association (2004); Roger et al. Circulation. 125(1):e2-e220 (2012)). Of these individuals, 82% are aware they have it, 75% are currently being treated for it, but only 52% have their blood pressure under control. Thus, about 48% of individuals with hypertension do not have adequate blood pressure control. Hypertension is known to lead to myocardial infarction (heart attack), stroke, renal failure, and death if not detected early and treated appropriately. In fact, in 2009, high blood pressure was listed as a primary or contributing cause of death in ~350,000 of the ~2.4 million U.S. deaths (14% of all deaths). From 1999-2009 the number of deaths attributable to hypertension increased by 44%.

Refractory (or resistant) hypertension is defined as blood pressure that remains above clinical guideline goals in spite of concurrent use of three antihypertensive agents of different classes (Akpunonu et al., Disease-a-month: DM. October 1996:42(10):609-722). Critically, refractory hypertension is noted in approximately 25-30% of all individuals being treated for hypertension. Refractory hypertension is a common clinical problem which contributes to the high levels of morbidity and mortality. The inability to gain control of blood pressure in these individuals may be related to the pharmacogenetics of the individual coupled with the specific classes of drugs and/or combination of classes chosen for that individual (Calhoun et al. Circulation 117 (25):e510-526 (2008); Johnson & Turner, Curr Opin Mol Ther 7(3):218-225 (2005)). In 2009, the direct and indirect economic burden on the United States health care system associated with hypertension was estimated at $51 billion. With the advent of improved diagnostic techniques, increased rates of health care utilization and screening, and the increasing age of the population, a continual upward trend in this expenditure is expected.

Globally, nearly 1 billion individuals have been diagnosed with hypertension with an estimate of an additional 400 million living with undiagnosed hypertension. *Hypertension* is the leading cause of premature death and the leading cause of cardiovascular disease worldwide. Similar to the continued upward trend in prevalence as seen in the United States, it is estimated that in 2025 approximately 1.56 billion adults will be living with hypertension. Because nearly two-thirds of the people living with hypertension worldwide reside in developing countries, providing optimal treatment at the lowest cost is critically important.

Unfortunately, despite a significant impulse in the medical community to move towards an "individualized medicine" approach to patient centered treatment, the current clinical treatment strategy is based on a set algorithm which does not take into account individual patient differences. Rather, physicians are guided to choose a drug (one out of many options) in a given class of drugs and use that specific drug as a "first line therapy" (typically initiating with the diuretic class) and titrate that specific drug of choice to therapeutic dosage regardless of efficacy (Chobanian et al. JAMA 289(19):2560-2572 (2003)). It is only after a prolonged course of treatment with that specific class of drug that clinical efficacy is determined (typically three months). At this stage, if clinical guideline goals for blood pressure have not been met, it is often recommended that the patient remain on the "first line therapy" whilst an additional drug from a different class of drugs (typically an Angiotensin converting enzyme inhibitor (ACE inhibitor) or Angiotensin II receptor blocker (ARB)) is added to the pharmacologic regimen. Again, this drug is titrated to recommended therapeutic dosage and another prolonged course of treatment is initiated before clinical efficacy is determined (an additional three months-six months since initiation of treatment). If at this point, clinical guideline goals for blood pressure have not been met, a third drug from a third class of drugs (typically a beta-blocker) is added and the process is repeated (another three months-nine months from initiation of treatment). Further, if clinical guideline goals have continued to be elusive, the diagnosis of refractory hypertension is added and the process is reinitiated with a different combination of drugs, different classes of drugs, different drug options within a given class of drugs, different dosages, or all of the above. Thus, from the time of initial diagnosis and the start of treatment to the point in which blood pressure is adequately controlled may take anywhere from three months to well over one year. This trial-and-error standard of care is clearly not optimal.

The blood pressure panel created by Geneticure has been created to comprehensively assess fourteen common genetic variants in the cardiac, vascular, and renal systems that can improve therapeutic guidance for the clinician based on known functional alterations of the protein through these genetic changes, as well as demonstrated effects of certain drug classes on these various genotypes. Based on this information, a clinician can guide therapy with knowledge specific to their patient, rather than "trial-and-error" based on population data and using drugs with least side effects initially.

1.1 Investigational Device: Geneticure Pharmacogenetic Testing Kit

The Geneticure pharmacogenetic testing kit contains two buccal swabs with two buffer solution vials to stabilize DNA. These buccal swabs are used for DNA collection which is then extracted for analysis of genes important in high blood pressure.

The Geneticure Pharmacogenetic Testing Kit is a pharmacogenomic treatment decision support product that tests for clinically important genetic variants affecting a patient's response to antihypertensive medications.

1.2 Genetic Analysis

Each sample can be analyzed for fourteen common genetic variants using 3 different methodologies, the Sequenom MassArray genotyping platform, Sanger sequencing using the ABI 3730xl genomic analyzer from Applied Biosystems, and classical PCR and gel sizing to determine insertion/deletion status (see. FIGS. 3A-3B).

2 Methodology 2.1 Study Design and Protocol Overview

This is a post-hoc association study of patients who have been diagnosed with high blood pressure and have been stable on medication treatment for at least 6 months. The purpose of this study is to evaluate the relationship between optimal medication therapy (or the therapy that has resulted in the most stable blood pressure for that particular patient) and the predicted optimal medication therapy based on a patient's genetic profile.

Chart reviews for the patient's history of antihypertensive therapy can be coupled with buccal swabs and blood pressure readings collected from eligible patients who have provided informed consent. The swab can be analyzed for fourteen genetic variants that are associated with antihypertensive therapy response (efficacy, side-effects).

2.2 Study Objective

To assess the relationship between the drug therapy class/combination of therapy classes that resulted in the best blood pressure control for a patient vs. what the Geneticure high blood pressure panel would have predicted.

2.3 Secondary Objectives

The secondary objectives are as follows:

To assess the clinical time to achieve optimal blood pressure treatment.

To assess the number of office visits required to achieve optimal blood pressure treatment.

3 Investigational Study Center

This study will be conducted at up to 5 study centers within the United States that have adequate resources for trial responsibilities.

4 Study Population

To be enrolled in this study, subjects must meet ALL of the inclusion criteria and NONE of the exclusion criteria:

4.1 Inclusion Criteria

1. Subject is able and willing to provide informed consent
2. Subject is ≤30 and ≤70 years of age
3. Subject with diagnosis of Hypertension for a minimum of 1 year
4. Subject has been on the same class/classes of blood pressure medication for a minimum of 6 months. Note: A change in dosage, frequency, or specific medication is acceptable as long as there have been no changes to the class/classes of medications prescribed.
5. Subject with a Body Mass Index (BMI) ≥19 and ≤35
6. Subject is currently prescribed and taking one of the following classes of medications alone or in combination with each other or a $Ca^{+}$ channel blocker.
   Diuretics
   ACE Inhibitors
   Angiotensin Receptor Blocker (ARB)
   Beta-blockers 4.2 Exclusion Criteria 1. Subject has clinically significant kidney disease as determined by the investigator.
2. Subject has clinically significant cardiac disease as determined by the investigator.
3. Subject has clinically significant vascular disease as determined by the investigator.

4. Subject has a diagnosis of secondary hypertension or is experiencing a complication of pregnancy.
5. Subject is currently prescribed and taking any additional class of medication(s) for high blood pressure not included in the list above, with the exception of a Ca+ channel blocker.
6. Subject has Systolic BP>190 or Diastolic BP>120 documented within the six months prior to visit.
7. Subject has a regular alcohol intake of greater than 21 units per week in the past 6 months
8. Subject has smoked greater than two packs of cigarettes (total) or equivalent nicotine intake in the past 6 months.
9. Subject has an anticipated survival less than 12 months.
10. Any other reason that the subject is inappropriate for study enrollment in the opinion of the Investigator.

5 Informed Consent

The investigator will prepare an informed consent form in accordance with this study protocol and all regulatory requirements (21 CFR Part 50) using the template informed consent form provided by the sponsor. The informed consent form must be submitted to the IRB and a copy of the final IRB-approved consent form must be submitted to the Study Management Center prior to the start of the study at that investigational site.

Prior to any study procedures, all subjects must document their consent for study participation and authorization for use and disclosure of health information by signing the IRB-approved Informed Consent Form. As part of the consent process, the subject will have the opportunity to ask questions of, and receive answers from the personnel conducting the study.

The investigator will notify the Study Management Center and the IRB within 5 working days if device use occurs without subject informed consent.

6 Study Assessments and Data Management 6.1 Screening

Identify Potential Study Subjects. Refer to the Inclusion and Exclusion Criteria sections of this protocol for a complete list of eligibility criteria.

Obtain Written Informed Consent. Each potential study participant must be given time to review the IRB-approved informed consent form, have his/her questions answered to their satisfaction and sign the form prior to any study procedures being performed. A subject will be given a copy of the informed consent form.

Review Inclusion/Exclusion Criteria. The investigator and/or designee will review all criteria to determine if the subject is eligible for enrollment. Eligibility of all subjects must personally be confirmed by the Investigator and will be documented on the CRF.

6.2 Enrollment

Assign Identification Number to Eligible Subjects. See Protocol section 6.3.

Record Demographics. Antihypertensive Medical History and current Blood Pressure. Data will be documented in the source document and recorded on the CRF, including but not limited to the following:

Age
Height
Weight
Race
Ethnicity
Length of Hypertension diagnosis
Previously and currently prescribed antihypertensive medications
Blood pressure measurements 6.3 Specimen Collection Collect Buccal Specimen.

Using the collection kit consisting of two buccal swabs and two uniquely barcoded tubes the investigator or designee will remove the first buccal brush and scrape the brush end across a Subject's right cheek repeatedly (for five seconds). The investigator/designee will place the brush end over the open buffer vial and press the opposite end of the swab stick to release the brush into the buffer and then close the vial. The process can be repeated on the left cheek. Each of the right and left cheek vial numbers must be recorded on the CRF and accountability log as right (R), or left (L).

Adverse Event Recording

Perform Product Accountability 6.4 Subject Numbering

Subjects meeting the criteria for enrollment (and their specimens) can be identified by unique numbers that can be assigned sequentially by order of enrollment. The pre-assigned investigational site number can be prefixed to the identification number and separated by a hyphen (e.g., site 01 would number their subjects sequentially as 01-001, 01-002, 01-003, etc.). Throughout the descriptions within the protocol the A swab will be referring to the swab that has originated from the right cheek, while the B swab will be that that has originated from the left cheek. To further clarify. Subject 01-001 can be given two barcoded tubes. These barcode numbers can be recorded for each patient. These can also be recorded as originating from the right cheek (A) or left cheek (B).

At no time should any study paperwork or specimens be marked with the subject's name or any other traceable identifier except for the informed consent form, which is signed by the subject and kept at the site. At no time should the original (signed) or a copy of this form be collected by the Sponsor or its representative.

6.5 Subject Completion and Withdrawal

Once subjects undergo the sampling procedure, their study participation is complete. There are no follow-up visits. Subjects will be instructed to notify the Investigator if they experience any symptoms or complications from the sampling procedure.

Subjects are free to withdraw consent and discontinue participation in the study at any time. A subject's participation in the study may be discontinued at any time at the discretion of the Investigator or Geneticure. The following may be justifiable reasons for the Investigator or Geneticure to remove a subject from the study:

The subject was erroneously included in the study or was found to have an exclusion criterion.

The subject was uncooperative.

The subject experienced an AE/SAE during the sample collection procedure that is considered intolerable by the subject or Investigator.

To the extent possible, safety data will be collected on subjects who discontinue participation in the study due to safety reasons.

The following may be justifiable reasons for the Investigator or Geneticure to remove a specimen from the study:

Sample is determined to be of poor or inadequate quality for analysis (e.g., contamination, insufficient material for analysis).

The sample was erroneously included in the study.

The specimen was not collected or processed per protocol procedures.

6.6 Concomitant Medications/Treatment/Procedures

This study protocol does not require change to any existing treatments or those prescribed during the course of the study by the Investigator or any other provider whom the subject sees for any medical reason. Outside of eligibility screening, there are no clinical evaluations as part of this study.

6.7 Data Management

The Investigator is responsible to ensure the accuracy, completeness, and timeliness of reported data.

All data will be sent to Geneticure who will enter it into the study database using a secure, protected Excel spreadsheet. The database will be validated prior to use in the study. All required data will be recorded on CRFs or paper facsimiles. Data collected within the CRFs will be supported by source documents as appropriate and may be updated to reflect the latest observations on the subjects participating in the study. Corrections to the source documentation can be made in a manner that does not obscure the original entry and will be dated and initialed by the Investigator or assigned designee. It is important for data entry to occur in a timely manner, therefore, data collected on source documents should be transferred into CRFs as soon as possible following study visits.

Study subject data can be reviewed at the investigational site by monitors at regular intervals throughout the study. Information on the CRFs can be compared to information originally recorded on source documents related to the study (i.e. professional notes, study-specific worksheets, etc.)

7 Genomic Core Laboratory

The subjects' cheek vials will be sent to the Geneticure processing center. The vials will then be batched and sent to the Genomic Core laboratory for DNA extraction and genetic analysis. Following analysis, results will be sent to Geneticure for statistical analysis and DNA will be destroyed.

A protocol for the extraction and analysis will be followed to ensure consistency and objectivity.

8 Adverse Events

The procedures outlined in this protocol do not involve significant risk to subject safety. Subjects will be provided the investigator's contact information and will be instructed to notify the investigator of any adverse events they experience during or secondary to the sample collection procedures.

8.1 Definitions 8.1.1 Adverse Event

For the purposes of this study, an adverse event is defined as any undesirable/unusual medical experience that occurs to a subject in conjunction with the use of the product, whether or not considered product related, including (but not limited to) those events that result from the use as stipulated in the protocol.

The following adverse events will not be collected in this study:

- Adverse events which, in the opinion of the Investigator, are unrelated to the swab collection procedure, but rather related to the subject's underlying medical conditions or status
- Adverse events that may be related to the sample collection procedure but result only in local, mild and transient discomforts.

The Investigator is responsible for documenting all Adverse Events on the Adverse Event CRF, except for those events noted above.

8.1.2 Serious Adverse Event

A Serious adverse event is an adverse event that:

- led to death.
- led to serious deterioration in the health of a subject that
  - resulted in a life-threatening illness or injury,
  - resulted in permanent impairment of a body structure or body function,
  - required inpatient hospitalization or prolongation of existing hospitalization,
  - resulted in medical or surgical intervention to prevent permanent impairment to a body structure or a body function.
- led to fetal distress, fetal death or a congenital anomaly or birth defect.

8.2 Event Reporting

Any AE, or SAE experienced by a subject after signing the informed consent until twenty-four (24) hours following study completion or termination will be recorded in the progress notes and on the CRF. The Investigator and/or designee will continue to monitor the subject with additional assessments until the AE is considered resolved, stabilized, or is lost to follow up.

A full description of an adverse event, including the nature, date and time of onset and resolution, determination of seriousness, frequency, severity, treatment, outcome, and relationship to the study will be recorded on the Adverse Event CRF.

SAEs must be reported to RCRI within 48 hours of the Investigator's first knowledge of the event.

9 Statistical Methods

Following is a summary of the Statistical Analysis Plan for the study. The following objectives have been prospectively defined; however, due to the nature of these data, additional analyses may be conducted or additional subsets may be identified that are not listed in this protocol.

9.1 Sample Size

Up to 300 subjects may be enrolled at each site. The minimum number of subjects for meaningful statistical analysis is 100 subjects.

9.2 Data Analysis

All data will be coded for statistical analysis (i.e. drug classes and genotypes will be coded numerically). All data will be analyzed with SPSS v.20. Normality of the data will be assessed using Levene's test prior to statistical analysis and any correction for non-normal data distribution will be used. Descriptive statistics will be computed (average time for blood pressure control, average number of visits to the clinician for blood pressure control, age, height, weight, BMI, etc.).

Data will be initially analysed following the collection of samples/data from 100 subjects. This will allow for direction for power calculations/etc. for future statistical analysis. Although some of the genes have been analysed individually, no mean or standard deviation data exists to allow for a true a priori power calculation. Data will be analysed again after two months or following 300 subjects for which data has been collected Statistical tests will be corrected for the number of tests run (preservation of alpha).

Ordinary least squares regression via univariate modelling will be used to estimate the magnitude of linearity between drug class that yielded the best blood pressure control and genetic profile of the subject. Multiple regression analysis will be performed to determine the impact of confounding variables (height, weight, age, race) on blood pressure control. For all statistical analyses an alpha level of 0.05 will be used to determine statistical significance 9.3 Other Statistical Considerations Justification of Pooling Data across Centers There is no need to keep the data from different centers separate for data collection Primary reasons for not pooling blood pressure data from different centers could include different races (which we are collecting as a demographic and analyzing as a co-variate in a multiple-regression) and different cultures (i.e. southern vs. northern habits of diet, exercise, etc.). The study will take race, height, weight, age into account as co-variates in a multiple regression model, but will not be powered to take into account possible geographic influences on the data.

Missing Data

All patients with available data will be included in the analyses of primary and secondary objectives. Because some of the data was not recorded as part of a prospective protocol, an unknown amount of data will be permanently missing. No patients will be contacted to retrieve missing data, and no sensitivity analyses will be performed on missing data.

10 Risk Analysis 10.1 Device Description

The procedures outlined in this protocol do not involve significant risk to subject safety. Subjects will be provided the investigator's contact information and will be instructed to notify the investigator of any adverse events they experience during or secondary to the specimen collection procedures.

The collection kit includes a small, soft, brush for cheek swabbing and a buffer solution in a small vial, one of each for each cheek, two in total. Once the swab has been placed into the lysis buffer the cells are no longer viable and therefore samples are now considered to be nucleic acids and safe to be shipped via standard mail.

11 Study Materials 11.1 Handling and Storage

The Investigator must ensure that the investigational product is stored in a controlled location with limited access.

11.2 Product Accountability

The investigator is responsible for investigational product accountability, reconciliation and record maintenance. The investigator must maintain investigational product accountability records throughout the course of the study.

Upon completion or termination of the study, all unused product, together with a copy of the product accountability form will be returned to Geneticure or its representative.

All supplies are to be used only for this protocol and not for any other purpose.

12 Study Administration 12.1 Subject Confidentiality

All information and data sent to Geneticure, and/or its designees concerning subjects and their participation in this study are considered confidential by Geneticure and it designees (subcontractors or contract research organization). Only authorized Geneticure personnel or approved contracted agents of Geneticure will have access to some portions of these confidential files and will act in accordance with applicable regulations as required by HIPAA. The IRBs and FDA also have the right to inspect and copy all records pertinent to this study. All data used in the reporting of the study will eliminate identifiable reference to the subjects.

12.2 Investigational Center Qualification

Investigational Center qualification visits or phone calls will be conducted by the Study Management Center prior to acceptance of the site into this study. The site qualification visit will be scheduled to include time with the Principal Investigator and other study personnel as applicable. Areas of discussion include a review of personnel training, investigator qualifications, adequacy of potential subject pool, FDA-regulated study experience, this study's specific requirements for procedures, and a review of staffing availability and appropriateness. A written report of the qualification visit will be drafted by the Study Management Center.

12.3 Site Training

Study-specific training of study personnel is the responsibility of the Sponsor or Study Management Center and the Principal Investigator. Study training will occur before the first device use. To ensure protocol and regulatory compliance as well as accurate data collection, site training will include a detailed review of the protocol, CRF completion, study specific procedures, monitoring logistics, and regulatory requirements.

12.4 Investigator Responsibilities

The investigator is responsible for ensuring that the study is conducted according to the investigational plan and all applicable FDA regulations, including reporting and record-keeping requirements, and controlling the devices undergoing investigation and HIPAA. In addition, the principal investigator is responsible for ensuring that informed consent is obtained from each subject prior to participating in the study, as well as protecting the rights, safety and welfare of participating subjects. Specific responsibilities are listed in this investigational plan.

Records and reports must remain on file at the investigational site for a minimum of two years after the later of either the completion/termination of the investigational study or the date it is determined the records are no longer required to support submissions to regulatory authorities. They may be discarded only upon approval from Geneticure. The Principal Investigator must contact Geneticure before destroying any records and reports pertaining to the study to ensure that they no longer need to be retained. In addition, Geneticure must be contacted if the investigator plans to leave the investigational site to ensure that arrangements for a new investigator or records transfer are made prior to investigator departure.

12.4.1 Records

Records to be maintained by the investigator in the designated investigational center's study file include:

- Investigational plan and all amendments
- Signed Financial Disclosure
- IRB approval letter including consent and HIPAA authorization form(s)
- IRB Membership list or Letter of Assurance
- All correspondence relating to the study between the site and Geneticure, and the Study Management Center
- CVs and professional licenses for all investigators
- Site personnel signature and responsibility list
- Clinical monitor sign-in log
- Blank set of each version of CRFs
- Subject Screening/Enrollment log
- Investigational device accountability log including: date, quantity, lot numbers of all devices, identification of all persons the device was used on and final disposition.

The following records are maintained for each subject enrolled in the study:

- Signed Consent Form and Authorization for the Use and Disclosure of Health Information
- Compete, accurate and current CRFs and DCFs Adverse event reports and any supporting documentation Protocol deviations Complete medical records, including procedure reports, lab reports, professional notes, etc.

Geneticure reserves the right to secure data clarification and additional medical documentation on subjects enrolled in this study at any time.

13 Abbreviations

AE=Event CRF=Case Report Form

DCF=Data Clarification Form FDA=Food and Drug Administration

HIPAA=Health Insurance Portability and Accountability Act of 1996

IRB/IEC=Institutional Review Board/Independent Ethics Committee

ITT=Intent-to-Treat PP=Per Protocol

SAE=Serious Adverse Event

UADE=Unanticipated Adverse Device Effect

Example 7: Results and Summary of Phase I Clinical Study

Introduction:

For this phase-I research study 14 genes within the Geneticure blood pressure (BP) panel were assessed as they relate to time to BP control and absolute BP values in 99 patients with hypertension. The study design utilized a post-hoc patient chart review carried out by two clinical sites through the direction of RCRI (a third-party clinical research firm) exploring genes important in drug metabolism, renal $Na^+$ handling, vascular function, and cardiac output (all of which can result differences in BP and response to BP therapy). Although the primary aim was BP control in response to therapy relative to genetic data, the time on average, it takes patients to achieve BP control without consideration of genetic information was also determined.

In summary, the study demonstrated that the genes in the Geneticure panel were predictive of time to BP control in patients with hypertension. In addition, there was an effect of several of the genes being predictive of BP taken within the clinic at the time of the research study. In addition, mechanistic data was gathered for the genes that encode the alpha subunit of the epithelial $Na^+$ channel (SCNN1A, rs #2228576) and found that SCNN1A was predictive of urinary $Na^+$ concentration and mean arterial BP.

Methods:

The BP history for patients was collected and the current BP levels were measured in patients with controlled hypertension. DNA was collected using a buccal swab and analyzed the genes within the Geneticure panel. The study sought to determine if patients with "functional" genotypes of proteins important in certain drug classes responded better if they were taking the drug that would inhibit the activity of that protein. As an example, the beta-1 adrenergic receptor (ADRB1) is important in heart rate control and patients who are on a beta-blocker can demonstrate a drop in BP because of inhibition of this protein. Therefore, one would hypothesize that if a patient with a functional protein of the ADRB1 is put on a beta-blocker early, they will demonstrate better BP control (because of a greater drop in heart rate and, therefore BP). This was assessed according to 14 genes and 3 major classes of BP drugs (diuretic, vasodilator, beta-blocker) and one drug metabolizing enzyme (CYP2D6).

Results: Subject Characteristics

Demographics (n=99)

| Variable | mean ± SEM |
|---|---|
| Age (yrs) | 58 ± 0.8 |
| Sex (% female) | 46 |
| Diabetes (% with) | 28 ± 4 |
| Weight (kg) | 86 ± 1.4 |
| Height (cm) | 169 ± 1 |
| BMI ($kg/m^2$) | 29.9 ± 0.4 |

Results: Blood Pressure Data (n=99)

| Variable | Mean ± SEM |
|---|---|
| Initial SBP (mmHg) | 151 ± 2 |
| Initial DBP (mmHg) | 91 ± 1 |
| Initial MAP (mmHg) | 111 ± 1 |
| Lowest SBP in past two years (mmHg) | 115 ± 1 |
| Lowest DBP in past two years (mmHg) | 72 ± 1 |
| Current SBP (mmHg) | 134 ± 2 |
| Current DBP (mmHg) | 82 ± 1 |
| Current MAP (mmHg) | 99 ± 1 |
| Time to BP control (months) | 22 ± 10 |
| Clinic Visits in the Past two years for HTN | 3.6 ± 0.3 |

Results: Current Blood Pressure Therapy Information

Drug Class Usage (n=99)

| Variable | mean ± SEM |
|---|---|
| Number of Classes of Drugs for HTN | 1.8 ± 0.08 |
| Diuretic (% taking) | 42 ± 5 |
| ACE Inhibitor (% taking) | 62 ± 5 |
| ARB (% taking) | 27 ± 5 |
| B-Blocker (% taking) | 33 ± 5 |
| $Ca^+$ Channel Blocker (% taking) | 16 ± 4 |

These data describe the number of different drug classes that the patients were taking. In addition, we assessed the percent of subjects who were on drugs within the vasodilator class (ACE-inhibitor and ARB), the cardiac class (B-blocker $Ca^+$ channel blocker), and the renal class (diuretic).

Time to Control According to Drug Class (n = 99)

| | Months For Control | | Clinic Visits/2 Years | |
|---|---|---|---|---|
| Drug Class | On the Drug Class | Not on the Drug Class | On the Drug Class | Not on the Drug Class |
| Diuretic | 39.5 ± 20.4 | 7.9 ± 4.2 | 4.5 ± 0.6 | 3.0 ± 0.4* |
| ACE Inhibitor | 22.2 ± 11.4 | 22.5 ± 16.4 | 3.1 ± 0.4 | 4.5 ± 0.6* |
| Antiotensin Receptor Blocker | 32.8 ± 23.1 | 17.1 ± 9.1 | 3.9 ± 0.6 | 3.5 ± 0.4 |
| B-Blocker | 24.5 ± 16.9 | 21.2 ± 12.0 | 4.9 ± 0.7 | 3.1 ± 0.4* |
| Ca+ Channel Blocker | 9.9 ± 4.5 | 25.0 ± 11.7 | 5.1 ± 0.7 | 3.3 ± 0.4 |

*$p < 0.05$ compared to those patients who were on the class of drugs

These data describe the time it took for BP control according to which class of drugs the patient was taking. While there are no significant differences in months taken for BP control according to drug class, there was an effect of number of clinic visits (specific to hypertension) within the past 2 years according to drug class. Patients using beta-blockade and diuretic therapy to control their BP had fewer clinic visits, when compared to those patients not on these therapies. Patients on an ACE-inhibitor had significantly more clinic visits per year, when compared to patients not on this therapy.

Blood Pressure Control According to Genotypes (n=86)

1. Genes important in renal $Na^+$ handling (and those that are differentially responsive to diuretic therapy).

| WNK1 (RS# 1159744) | | | | |
|---|---|---|---|---|
| | On Target Therapy (Diuretic) | | | |
| | No | | Yes | |
| Genotype | GG | C•containing | GG | C•containing |
| n | 26 | 24 | 19 | 15 |
| Systolic Blood Pressure (mm Hg) | 133.7 ± 3.2 | 133.5 ± 2.3 | 137.8 ± 4.1 | 132.1 ± 5.2 |
| Diastolic Blood Pressure | 79.7 ± 2.3 | 84.6 ± 2.0 | 88.7 ± 2.7* | 79.5 ± 3.7 |
| Mean Arterial Blood Pressure (mm Hg) | 97.7 ± 2.4 | 100.9 ± 1.81 | 105.1 ± 2.7* | 97.1 ± 3.6 |
| Months to BP Control | 3.6 ± 1.4 | 4.8 ± 2.6 | 8.2 ± 5.6 | 16.5 ± 6.2 |

*P < 0.05 compared to same genotype not on target therapy.

| SLC12A3 (RS# 1529927) | | | | |
|---|---|---|---|---|
| | On Target Therapy (Diuretic) | | | |
| | No | | Yes | |
| Genotype | GG | C•containing | GG | C•containing |
| n | 45 | 6 | 33 | 2 |
| Systolic Blood Pressure (mm Hg) | 134.2 ± 2.31 | 136.8 ± 5.9 | 136.4 ± 3.4 | 128.0 ± 8 |
| Diastolic Blood Pressure (mm Hg) | 81.8 ± 1.7 | 86.5 ± 2.3 | 85.9 ± 2.5 | 75.0 ± 5.0 |
| Mean Arterial Blood Pressure (mm Hg) | 99.3 ± 1.7 | 103.3 ± 3.1 | 102.7 ± 2.4 | 92.3 ± 6.0 |
| Months to BP Control | 2.5 ± 0.7 | 17.7 ± 7 | 10.5 ± 3.9 | 42 |

| WNK1 (RS# 2107614) | | | | |
|---|---|---|---|---|
| | On Target Therapy | | | |
| | No | | Yes | |
| Genotype | GG | C•containing | G | C•containing |
| n | 9 | 41 | 7 | 27 |
| Systolic Blood Pressure (mm Hg) | 130.3 ± 5.6 | 134.4 ± 2.1 | 147.7 ± 7.9 | 132.1 ± 3.3 |
| Diastolic Blood Pressure (mm Hg) | 80.4 ± 4.7 | 82.4 ± 1.6 | 84.6 ± 4 | 84.7 ± 2.8 |
| Mean Arterial Blood Pressure (mm Hg) | 97.1 ± 4.6 | 99.7 ± 1.6 | 106 ± 4.4 | 100.5 ± 2.6 |
| Months to BP Control | 10.5 ± 7.2 | 2.6 ± 0.9 | 10.5 ± 9.5 | 13.1 ± 4.8 |

| Alpha Adducin (RS# 4961) | | | | |
|---|---|---|---|---|
| | On Target Therapy | | | |
| | No | | Yes | |
| Genotype | GG | T•containing | GG | T•containing |
| n | 40 | 11 | 24 | 11 |
| Systolic Blood Pressure (mm Hg) | 134.2 ± 2.3 | 135.0 ± 5.3 | 135.3 ± 3.9 | 137.4 ± 5.9 |
| Diastolic Blood Pressure (mm Hg) | 83.1 ± 1.8 | 79.7 ± 3.3 | 85.8 ± 2.9 | 84.2 ± 4.3 |
| Mean Arterial Blood Pressure (mm Hg) | 100.2 ± 1.8 | 98.2 ± 3.6 | 102.3 ± 2.7 | 101.9 ± 4.5 |
| Months to BP Control | 4.4 ± 1.6 | 3.6 ± 15.1 | 10.5 ± 5.2 | 15.1 ± 6.7 |

Of the four genes explored in the clinical study RS #1159744 (the gene that encodes cytoplasmic serine-threonine kinase that is expressed in the kidney, WNK-1) was most predictive of response to therapy. Patients with the C genotype of WNK-1 had the best response to therapy demonstrating 8 mmHg lower DBP, when compared to patients with this genotype who were not on diuretic therapy. Subjects who were homozygous for G for this gene actually had a lower blood pressure if they were not on a diuretic, indicating that they may be benefiting from alternate therapy. Although just a trend (due to small sample size of the minor allele) the C polymorphism of SLC12A3 also may be predictive of response to diuretic therapy with patients demonstrating an 11 mmHg drop in DBP with therapy, compared to the G polymorphism which demonstrated a small increase in DBP with therapy.

Figure 8:
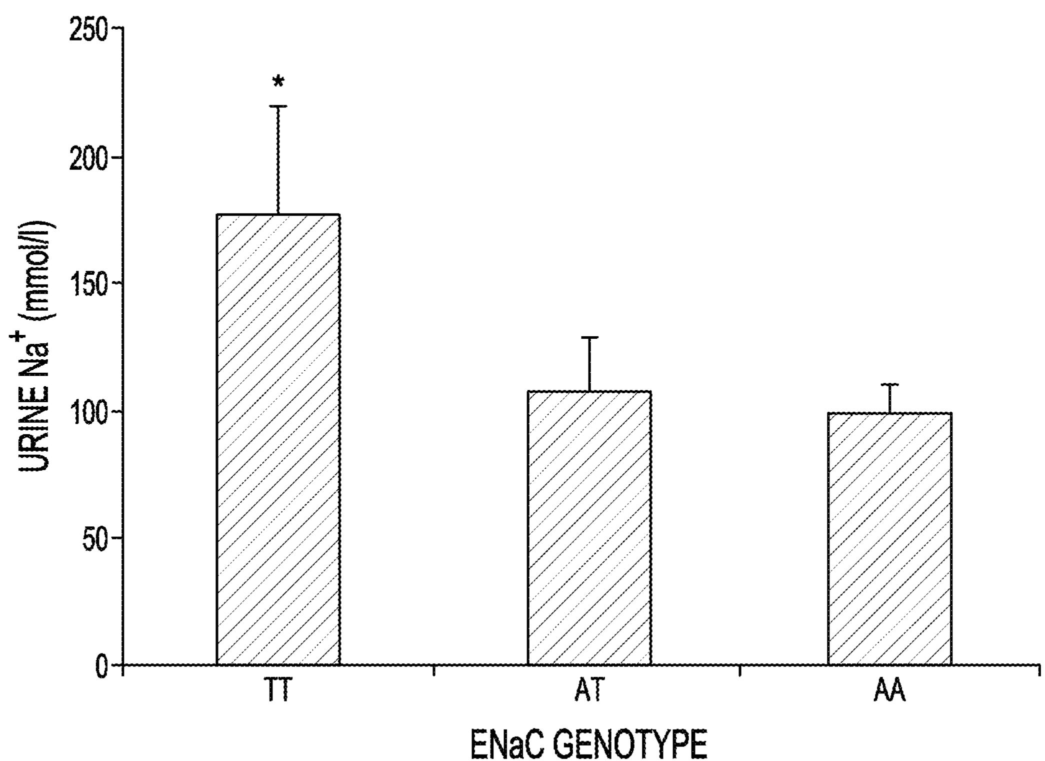
FIG. 8 is a bar graph of urinary sodium output as a function of genetic variation of SCNN1A.
Figure 9:
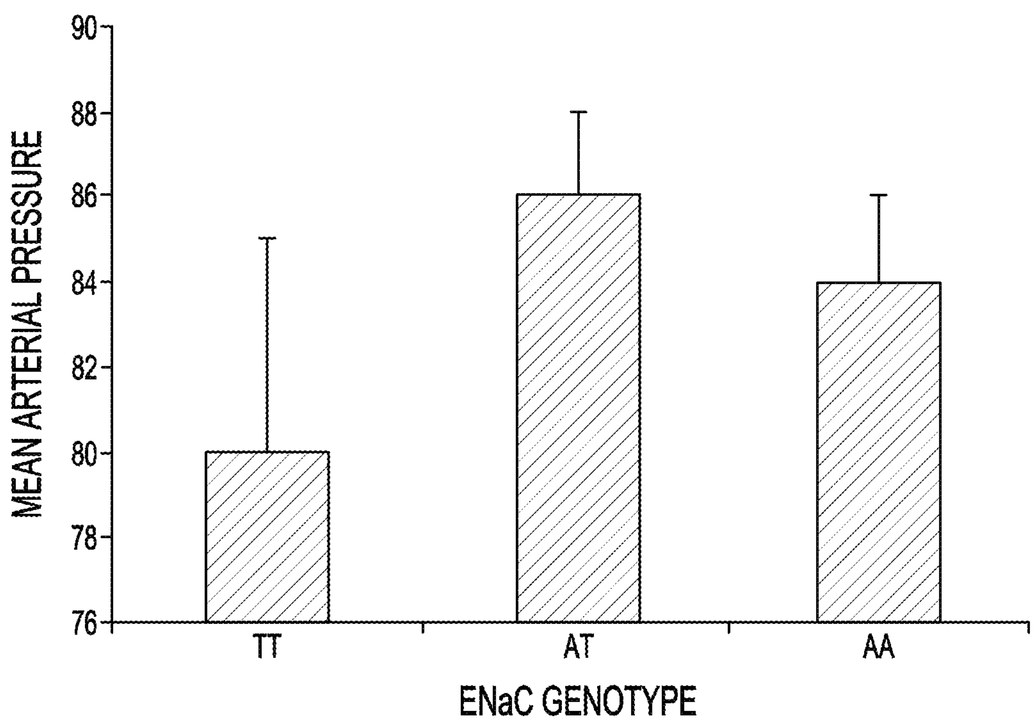
FIG. 9 is a bar graph of mean arterial blood pressure as a function of genetic variation of SCNN1A.

In addition to this clinical BP data 24-hour urinary and resting BP data were gathered according to genetic variation of the alpha sub-unit of the epithelial $Na^+$ channel (SCNN1A, RS #2228576). It was found that subjects homozygous for the T variant of SCNN1A demonstrated more $Na^+$ excretion from the kidneys and they also demonstrated lower mean arterial blood pressure, when compared to genotype groups containing the A variant (See FIGS. 8 and 9).

2. Genes important in cardiac function (and those that may respond differentially to beta-blocker therapy).

The beta-1 adrenergic receptor (ADRB1) is important in controlling heart rate and cardiac contractility.

Beta-1 Adrenergic Receptor 49 (RS# 1801252)

| | On Target Therapy (Beta-Blocker) | | | |
|---|---|---|---|---|
| | No | | Yes | |
| Genotype | Ser/Ser | Thr•containing | Ser/Ser | Thr•containing |
| n | 1 | 55 | 2 | 28 |
| Systolic Blood Pressure (mm Hg) Diastolic | 137 | 136.4 ± 2.3 | 136 ± 6 | 132.4 ± 3.2 |
| Diastolic Blood Pressure (mm Hg) | 86 | 85.5 ± 1.7 | 75 ± 3 | 80.3 ± 2.1* |
| Mean Arterial Blood Pressure (mm Hg) | 103 | 102.4 ± 1.7 | 95 ± 0 | 97.7 ± 2.1 |
| Months to BP Control | N/A | 7.0 ± 2.4 | N/A | 9.4 ± 3.8 |

*P < 0.05 compared to same genotype not on target therapy.

Beta-1 Adrenergic Receptor 389 (RS# 1801253)

| | On Target Therapy (Beta-Blocker) | | | |
|---|---|---|---|---|
| | No | | Yes | |
| Genotype | GG | C•containing | GG | C•containing |
| n | 56 | 0 | 30 | 0 |
| Systolic Blood Pressure (mm Hg) Diastolic | 136.4 ± 2.3 | | 132.6 ± 3.0 | |
| Diastolic Blood Pressure (mm Hg) | 85.5 ± 1.7 | | 80.0 ± 2.0* | |
| Mean Arterial Blood Pressure (mm Hg) | 102.4 ± 1.7 | | 97.5 ± 1.98 | |
| Months to BP Control | 7.0 ± 2.3 | | 8.8 ± 3.5 | |

*P < 0.05 compared to same genotype not on target therapy.

These data indicate a differential BP response to beta-blocker therapy according to genetic variation at position 49 of the ADRB1. Specifically, the inventors found that subjects with the Ser genotype at position 49 of ADRB1 benefit from beta-blocker therapy with an average drop in DBP of 11 mmHg, compared with a drop of 5 mmHg with Thr at this position. Therefore, although patients with the Thr polymorphism also demonstrated a drop in BP with beta-blocker therapy, the effect was most pronounced in patients with the Ser polymorphism.

The beta-2 adrenergic receptor (ADRB2) is important in cardiac contractility, which controls stroke volume, and can influence BP through differences in cardiac output.

Beta-2 Adrenergic Receptor 16 (RS# 1042713)

| | On Target Therapy (B-Blocker) | | | |
|---|---|---|---|---|
| | No | | Yes | |
| Genotype | Arg/Arg | Gly-containing | Arg/Arg | Gly-containing |
| n | 5 | 51 | 3 | 27 |
| Systolic Blood Pressure (mmHg) | 143.6 ± 5.9 | 135.7 ± 2.4 | 129 ± 5 | 133.3 ± 3 |
| Diastolic Blood Pressure (mmHg) | 84.0 ± 7.4 | 85.6 ± 1.8 | 80.3 ± 6.6 | 79.9 ± 2.1* |
| Mean Arterial Blood Pressure (mmHg) | 104.0 ± 6.82 | 102.3 ± 1.8 | 96.6 ± 5.9 | 97.6 ± 2.1 |
| Months to BP Control | 7 ± 5 | 7 ± 2.6 | 4.3 ± 3.8 | 9.9 ± 4.3 |

*P < 0.05 compared to same genotype not on target therapy

Beta-2 Adrenergic Receptor 27 (RS# 1042714)

| | On Target Therapy (B-Blocker) | | | |
|---|---|---|---|---|
| | No | | Yes | |
| Genotype | Gln/Gln | Glu-containing | Gln/Gln | Glu-containing |
| n | 6 | 48 | 4 | 24 |
| Systolic Blood Pressure (mmHg) | 142.0 ± 6.9 | 134.4 ± 2.2 | 125.5 ± 5.9 | 132.7 ± 3.6 |
| Diastolic Blood Pressure (mmHg) | 82.5 ± 2.7 | 85.1 ± 1.8 | 82.5 ± 2.7 | 79.5 ± 2.4 |
| Mean Arterial Blood Pressure (mmHg) | 102.3 ± 4.1 | 101.5 ± 1.8 | 102.3 ± 4.1 | 97.2 ± 2.3 |
| Months to BP Control | 8.5 ± 7.8 | 7 ± 2.8 | 5.3 ± 2.3 | 9.6 ± 4.4 |

These data demonstrate a generally favorable response to beta-blocker therapy with both genotype groups. However, the Gly16 genotype demonstrated a statistically significant difference in BP control if the patients were on a beta-blocker (drop in DBP of 5 mmHg), when compared to patients with the Arg16 genotype. Generally, there is a similar pattern for a greater drop in BP with subjects who have the most functional gene that encodes the ADRB2 (Gly at position 16 and Glu at position 27). There is strong linkage disequilibrium between these two sites (amino acids 16 and 27), so the similar response between the sites is expected.

Observations on Genetic Variation of Cytochrome P450 2D6 (CYP2D6), which is Important in Drug Metabolism, Especially of Particular Beta-Blockers.

| CYP 2D6 (RS#) | | | | |
|---|---|---|---|---|
| | On Target Therapy (B-Blocker) | | | |
| | No | | Yes | |
| Genotype | CC | T-Containing | CC | T-Containing |
| n | 35 | 22 | 23 | 7 |
| Systolic Blood Pressure (mmHg) | 140.6 ± 2.7 | 128.5 ± 3.1 | 133.4 ± 3.6 | 130.0 ± 5.7 |
| Diastolic Blood Pressure (mmHg) | 86.0 ± 2.4 | 83.2 ± 2.4 | 79.2 ± 2.1* | 82.6 ± 5.3 |
| Mean Arterial Blood Pressure (mmHg) | 104.2 ± 2.3 | 98.3 ± 2.4 | 97.3 ± 2.2* | 98.4 ± 4.8 |
| Months to BP Control | 7.8 ± 2.9 | 5.08 ± 3.7 | 6.25 ± 3.2 | 16.5 ± 10.8 |

*P < 0.05 compared to same genotype not on target therapy

These data demonstrate that the CC homozygous group of CYP2D6 demonstrates the greatest response to beta-blocker therapy, when compared to the CT and TT groups. Patients with the CC polymorphism had demonstrated a 6 mmHg lower DBP and a 7 mmHg lower MAP when on beta-blocker therapy, compared to this genotype not on beta-blocker therapy. In contrast, patients in the T-containing group (those with the CT and TT genotypes) did not respond to beta-blocker therapy.

3. Genes important in vascular function (and those that may respond differentially to vasodilator therapy).

The following are observations on the genetic variation of the angiotensin gene (encoding a precursor to angiotensin-II, a potent vasoconstrictor, which is converted via angiotensin converting enzyme, ACE) and the responses to various therapies.

| Angiotensin (RS# 699) | | | | |
|---|---|---|---|---|
| | On Target Therapy (Angiotensin Receptor Blocker) | | | |
| | No | | Yes | |
| Genotype | CC | T-containing | CC | T-containing |
| n | 15 | 50 | 4 | 17 |
| Systolic Blood Pressure (mmHg) | 135.3 ± 2.6 | 135.1+2.6 | 135.0 ± 7.4 | 135.1 ± 4.5 |
| Diastolic Blood Pressure (mmHg) | 89.5 ± 2.9 | 82.6 ± 1.7 | 77.5 ± 7.8 | 82.7 ± 3.4 |
| Mean Arterial Blood Pressure (mmHg) | 104.7 ± 2.6 | 100.1 ± 1.7 | 96.6 ± 7.5 | 100.2 ± 3.3 |
| Months to BP Control | 2.7 ± 1.3 | 6.7 ± 2.7 | 12 | 12.4 ± 4.8 |

-continued

| Angiotensin (RS# 699) | | | | |
|---|---|---|---|---|
| | On Target Therapy (ACE-Inhibitor) | | | |
| | No | | Yes | |
| Genotype | CC | T-containing | CC | T-containing |
| n | 6 | 24 | 13 | 43 |
| Systolic Blood Pressure (mmHg) | 131.7 ± 5.3 | 133.7 ± 3.5 | 136.8 ± 2.7 | 135.8 ± 2.9 |
| Diastolic Blood Pressure (mmHg) | 78.5 ± 5.0 | 80.4 ± 2.1 | 90.8 ± 3.2* | 83.9 ± 2.0 |
| Mean Arterial Blood Pressure (mmHg) | 96.2 ± 4.7 | 98.2± | 106.2 ± 2.8* | 101.1 ± 2.0 |
| Months to BP Control | 6.7 ± 3.1 | 7.7 ± 3.2 | 2.3 ± 1.7 | 9.9 ± 3.8 |

| All Receptor Type-1 (RS# 5186) | | | | |
|---|---|---|---|---|
| | On Target Therapy (Angiotensin Receptor Blocker) | | | |
| | No | | Yes | |
| Genotype | AA | C-containing | AA | C-containing |
| n | 39 | 28 | 9 | 11 |
| Systolic Blood Pressure (mmHg) | 137.3 ± 2.6 | 131.0 ± 3.1 | 136.3 ± 4.6 | 134.1 ± 6.5 |
| Diastolic Blood Pressure (mmHg) | 85.4 ± 2.1 | 80.9 ± 2.0 | 87.6 ± 3.9 | 77.9 ± 4.5 |
| Mean Arterial Blood Pressure (mmHg) | 102.7 ± 2.0 | 97.6 ± 2.1 | 103.8 ± 2.9 | 96.6 ± 4.9 |
| Months to BP Control | 7.3 ± 2.9 | 3.8 ± 2.5 | 13.4 ± 7.8 | 11.9 ± 5.7 |

*P < 0.05 compared to same genotype not on target therapy

These data indicate that patients homozygous for the C genotype of angiotensin may benefit from an angiotensin receptor blocker (ARB) When on an ARB, patients with the CC genotype demonstrated a 12 mmHg lower DBP when compared to patients with this genotype who were not on this therapy. In contrast, patients in the T-containing group (those with the CT or TT genotypes) did not show a response to ARB therapy. Furthermore, inhibition of ACE (which converts angiotensin-1 to angiotensin-II) results in higher BP levels, possibly due to a “build-up” of angiotensin. Therefore, these data indicate that patients homozygous for C should be given an angiotensin receptor blocker with an ACE inhibitor.

Angiotensin Converting Enzyme (ACE) Genotype and ACE-Inhibition

| ACE (RS# 1799752) | | | | |
|---|---|---|---|---|
| | On Target Therapy (ACE-Inhibition) | | | |
| | No | | Yes | |
| Genotype | Ins/Ins | Del•Containing | Ins/Ins | Del•Containing |
| n | 3 | 27 | 12 | 47 |
| Systolic Blood Pressure (mm Hg) | 142.7 ± 11.1 | 132.3 ± 3.1 | 129.5 ± 3.5 | 137.1 ± 2.6 |
| Diastolic Blood Pressure (mm Hg) | 79.6 ± 6.1 | 80.0 ± 2.1 | 80.4 ± 4.4 | 85.7 ± 1.9* |
| Mean Arterial Blood Pressure (mm Hg) | 100.7 ± 7.7 | 97.4 ± 2.1 | 96.8 ± 3.8 | 102.8 ± 1.8 |
| Months to BP Control | 4.7 ± 3.7 | 8.0 ± 3 | 7.4 ± 5.8 | 7.3 ± 3.0 |

*P < 0.05 compared to same genotype not on target therapy.

These data indicate that those with the Insertion polymorphism (Ins) of the ACE gene will respond best to ACE-inhibition. Patients with the Del polymorphism actually demonstrated higher DBP with ACE-inhibition, when compared to this patient group not on ACE-inhibitors.

Observations on Renin Genotype and Angiotensin Receptor Blocker

Renin is a precursor to angiotensin and, therefore, patients with a functional genotype of renin may benefit from Angiotensin Receptor Blocker (ARB) therapy because a more functional genotype can lead to greater angiotensin levels which can result in high BP.

| Renin (RS# 12750834) | | | | |
|---|---|---|---|---|
| | On Target Therapy (Angiotensin Receptor Blocker) | | | |
| | No | | Yes | |
| Genotype | G/G | A•containing | G/G | A•containing |
| n | 48 | 17 | 14 | 7 |
| Systolic Blood Pressure (mm Hg) | 134.8 ± 2.3 | 135.9 ± 4.4 | 136.4 ± 4.6 | 132.2 ± 7.3 |
| Diastolic Blood Pressure (mm Hg) | 83.8 ± 1.7 | 85.1 ± 2.9 | 82.0 ± 2.9 | 81.0 ± 7.4 |
| Mean Arterial Blood Pressure (mm Hg) | 100.8 ± 1.7 | 102.1 ± 2.9 | 100.2 ± 3.2 | 98.1 ± 6.6 |
| Months to BP Control | 4.75 ± 1.9 | 8.0 ± 5.8 | 15.5 ± 5.3* | 1.3 ± 0.7 |

*P < 0.05 compared to same genotype not on target therapy.

These data indicate that the functional genotype of renin (A) may benefit from ARB therapy. Specifically, the BP response to therapy was not significant, however, the response to therapy time was pronounced. Patients who have the functional genotype of renin (the AG and AA genotype groups) demonstrate a much shorter time to BP control, when compared to patients within this group who do not take this therapy. In contrast, patients in the GG group demonstrate a longer time to control if they take this therapy, possibly due to greater response to another class of drugs.

REFERENCES

1. Kearney P M, Whelton M, Reynolds K, Muntner P, Whelton P K, He J. Global burden of hypertension: Analysis of worldwide data. *Lancet* 2005; 365:217-223.
2. Brodde O E. The functional importance of beta 1 and beta 2 adrenoceptors in the human heart. *Am J Cardiol* 1988; 62:24C-29C.
3. Snyder E M, Wong E C, Foxx-Lupo W T, Wheatley C M, Cassuto N A, Patanwala A E. Effects of an inhaled beta2-agonist on cardiovascular function and sympathetic activity in healthy subjects. *Pharmacotherapy* 2011; 31:748-756.
4. Johnson J A, Turner S T. Hypertension pharmacogenomics: Current status and future directions. *Curr Opin Mol Ther* 2005; 7:218-225.
5. La Rosee K, Huntgeburth M, Rosenkranz S, Bohm M, Schnabel P. The arg389gly beta1-adrenoceptor gene polymorphism determines contractile response to catecholamines. *Pharmacogenetics* 2004; 14:711-716.
6. Liu J. Liu Z-Q, Tan Z-R, Chen X-P, Wang L-S. Zhou G, Zhou H-H. Gly389arg polymorphism of [beta]1-adrenergic receptor is associated with the cardiovascular response to metoprolol[ast]. *Clin Pharmacol Ther* 2003; 74:372-379.
7. Snyder E M, Beck K C, Dietz N M, Eisenach J H, Joyner M J, Turner S T, Johnson B D. Arg16gly polymorphism of the {beta}2-adrenergic receptor is associated with differences in cardiovascular function at rest and during exercise in humans. *J Physiol* 2006; 571:121-130.
8. Snyder E M, Hulsebus M L, Turner S T, Joyner M J, Johnson B D. Genotype related differences in beta2 adrenergic receptor density and cardiac function. *Med Sci Sports Exerc* 2006; 38:882-886.
9. Snyder E M, Johnson B D, Joyner M J. Genetics of beta2-adrenergic receptors and the cardiopulmonary response to exercise. *Exerc Sport Sci Rev* 2008; 36:98-105.
10. Snyder E M, Joyner M J, Turner S T, Johnson B D. Blood pressure variation in healthy humans: A possible interaction with beta-2 adrenergic receptor genotype and renal epithelial sodium channels. *Med Hypotheses* 2005; 65:296-299.
11. Snyder E M, Turner S T. Joyner M J, Eisenach J H, Johnson B D. The arg16gly polymorphism of the {beta}2-adrenergic receptor and the natriuretic response to rapid saline infusion in humans. *J Physiol* 2006; 574:947-954.
12. Ulgen M S, Ozturk O, Alan S, Kayrak M, Turan Y, Tekes S, Toprak N. The relationship between angiotensin-converting enzyme (insertion/deletion) gene polymorphism and left ventricular remodeling in acute myocardial infarction. *Coron Artery Dis* 2007; 18:153-157.
13. McNamara D M, Holubkov R, Postava L, Janosko K, MacGowan G A, Mathier M, Murali S. Feldman A M, London B. Pharmacogenetic interactions between angiotensin-converting enzyme inhibitor therapy and the angiotensin-converting enzyme deletion polymorphism in patients with congestive heart failure. *J Am Coll Cardiol* 2004; 44:2019-2026.
14. Pilati M, Cicoira M, Zanolla L, Nicoletti I, Muraglia S, Zardini P. The role of angiotensin-converting enzyme polymorphism in congestive heart failure. *Congest Heart Fail* 2004:10:87-93: quiz 94-85.

15. Pilbrow A P, Palmer B R, Frampton C M, Yandle T G, Troughton R W, Campbell E, Skelton L, Lainchbury J G, Richards A M, Cameron V A. Angiotensinogen m235t and t174m gene polymorphisms in combination doubles the risk of mortality in heart failure. *Hypertension* 2007:49: 322-327.
16. Tang W, Devereux R B, Rao D C, Oberman A, Hopkins P N, Kitzman D W, Arnett D K. Associations between angiotensinogen gene variants and left ventricular mass and function in the hypergen study. *Am Heart j* 2002; 143:854-860.
17. Miller J A, Thai K, Scholey J W. Angiotensin ii type 1 receptor gene polymorphism predicts response to losartan and angiotensin ii. *Kidney Int* 1999; 56:2173-2180.
18. Baudin B. Angiotensin ii receptor polymorphisms in hypertension. Pharmacogenomic considerations. *Pharmacogenomics* 2002; 3:65-73.
19. Vangjeli C, Clarke N, Quinn U, Dicker P, Tighe O, Ho C, O'Brien E, Stanton A V. Confirmation that the renin gene distal enhancer polymorphism ren-5312c/t is associated with increased blood pressure. *Circulation Cardiovascular genetics* 2010; 3:53-59.
20. Meisler M H, Barrow L L, Canessa C M, Rossier B C. Scnn1, an epithelial cell sodium channel gene in the conserved linkage group on mouse chromosome 6 and human chromosome 12. *Genomics* 1994:24:185-186.
21. Jin H S, Hong K W, Lim J E, Hwang S Y, Lee S H, Shin C, Park H K, Oh B. Genetic variations in the sodium balance-regulating genes enac, nedd41, ndfip2 and usp2 influence blood pressure and hypertension. *Kidney Blood Press Res* 2010:33:15-23.
22. Pratt J H. Central role for enac in development of hypertension. *J Am Soc Nephrol* 2005; 16:3154-3159.
23. Zhang L N, Ji L D, Fei L J, Yuan F, Zhang Y M, Xu J. Association between polymorphisms of alpha-adducin gene and essential hypertension in chinese population. *BioMed research international* 2013:2013:451094.
24. Psaty B M, Smith N L, Heckbert S R, Vos H L, Lemaitre R N, Reiner A P, Siscovick D S, Bis J, Lumley T, Longstreth W T, Jr., Rosendaal F R. Diuretic therapy, the alpha-adducin gene variant, and the risk of myocardial infarction or stroke in persons with treated hypertension. *JAMA* 2002:287:1680-1689.
25. Turner S T, Schwartz G L, Chapman A B, Boerwinkle E. Wnk1 kinase polymorphism and blood pressure response to a thiazide diuretic. *Hypertension* 2005; 46:758-765.
26. The sixth report of the Joint National Committee on prevention, detection, evaluation, and treatment of high blood pressure. Arch Intern Med. Nov. 24, 1997; 157(21): 2413-2446.
27. Chobanian A V, Bakris G L, Black H R, et al. The Seventh Report of the Joint National Committee on Prevention, Detection, Evaluation, and Treatment of High Blood Pressure: the JNC 7 report. Jama. May 21, 2003; 289(19):2560-2572.
29. American Heart Association. Heart and Stroke Statistics—2004 Update. Paper presented at: Dallas: American Heart Association 2004.
30. Roger V L, Go A S, Lloyd-Jones D M, et al. Heart disease and stroke statistics—2012 update: a report from the American Heart Association. Circulation. Jan. 3, 2012; 125(1):e2-e220.
31. Akpunonu B E, Mulrow P J, Hoffman E A. Secondary hypertension: evaluation and treatment. Disease-a-month: DM. October 1996; 42(10):609-722.
32. Calhoun D A, Jones D, Textor S, et al. Resistant hypertension: diagnosis, evaluation, and treatment: a scientific statement from the American Heart Association Professional Education Committee of the Council for High Blood Pressure Research. Circulation. Jun. 24, 2008; 117(25):e510-526.
33. Johnson J A, Turner S T. Hypertension pharmacogenomics: current status and future directions. Curr Opin Mol Ther. June 2005; 7(3):218-225.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods, devices, and kits described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed:

1. A method for treating an individual patient having hypertension, the method comprising administering to the individual patient a first line therapy antihypertensive drug selected from the group consisting of a diuretic drug, a vasodilator drug and a beta blocker drug, wherein the diuretic drug includes a thiazide diuretic drug, a loop diuretic drug or an amiloride potassium sparing diuretic drug, and the vasodilator drug includes an angiotensin II receptor antagonist drug or an ACE inhibitor drug, comprising determining the individual patient's genotype for each of fourteen single nucleotide polymorphisms: rs1159744: rs2107614; rs4961; rs1529927; rs3892097; rs1801253; rs1801252; rs12750834; rs5186; rs1799752; rs699; rs2228576; rs1042714; and rs1042713, by the steps of:

obtaining the patient's DNA from a tissue or fluid sample from the patient, conducting a polymerase amplification of segments of the patient's DNA using primers relating to the fourteen single nucleotide polymorphisms to produce nucleotide fragments of the patient's genotype, introducing the nucleotide fragments into a time-of-flight mass spectrometer to identify the nucleotide sequences of the patient's genotype, and administering to the individual patient the first line therapy antihypertensive drug according to one of the following procedures a, b, c, d, e, f or g:

a) administering the diuretic drug when the patient's genotype is homozygous for cytosine at the variable position of rs1159744 or rs2107614;

b) administering the thiazide or a thiazide-like diuretic drug when the patient's genotype is homozygous for thymine at the variable position of rs4961 or rs1529927;

c) administering the beta-blocker drug when the patient's genotype is homozygous for any one of the snps selected from adenine at the variable position of rs3892097, cytosine at the variable position of rs1801253, adenine at the variable position of rs1801252, guanine at the variable position of rs1042714 or guanine at the variable position of rs1042713;

d) administering the angiotensin II receptor antagonist vasodilator drug when the patient's genotype is homozygous for cytosine at the variable position of rs12750834 or rs5186;

e) administering the ACE inhibitor vasodilator drug when the patient's genotype is homozygous for a deletion in rs1799752 or cytosine at the variable position of rs699;

f) administering an amiloride potassium sparing diuretic drug when the patient's genotype is homozygous for adenine at the variable position of rs2228576; and g) administering the loop diuretic drug when the patient's genotype is not homozygous for the snps with the variable position nucleotides of procedures a, b, c, d, e, and f.

2. A method according to claim 1 wherein the fourteen single nucleotide polymorphisms are determined sequentially or simultaneously.

3. A method according to claim 2 wherein the single nucleotide polymorphisms are determined simultaneously.

4. A method according to claim 1 wherein the patient's genotype of procedures c, d, e and f does not have the homozygous single nucleotide sequences of procedures a and b.

5. A method according to claim 1 wherein the polymerase amplification comprises a first step of a PCR amplification using PCR primers corresponding to portions of the fourteen snp's and a second step of an SNE extension using SNE primers and all four nucleotide terminators with the SNE primers corresponding to portions of the fourteen snps extending from the variable nucleotide toward the 5' end, to produce fourteen SNE extended sequences with each SNE extended sequence having as its 3'terminus the variable nucleotide of the corresponding snp.

6. A method according to claim 5 wherein the fourteen single nucleotide polymorphisms are determined sequentially or simultaneously.

7. A method according to claim 6 wherein the fourteen single nucleotide polymorphisms are determined simultaneously.

* * * * *

SEQUENCE LISTING

<160> NUMBER OF SEQ ID NOS: 85

<210> SEQ ID NO 1
<211> LENGTH: 2862
<212> TYPE: DNA
<213> ORGANISM: Homo sapiens

<400> SEQUENCE: 1

```
gcaccacgcc gcccgggctt ctggggtgtt ccccaaccac ggcccagccc tgccacaccc     60
cccgcccccg gcctccgcag ctcggcatgg gcgcgggggt gctcgtcctg ggcgcctccg    120
agcccggtaa cctgtcgtcg gccgcaccgc tccccgacgg cgcggccacc gcggcgcggc    180
tgctggtgcc cgcgtcgccg cccgcctcgt tgctgcctcc cgccagcgaa agccccgagc    240
cgctgtctca gcagtggaca gcgggcatgg gtctgctgat ggcgctcatc gtgctgctca    300
tcgtggcggg caatgtgctg gtgatcgtgg ccatcgccaa gacgccgcgg ctgcagacgc    360
tcaccaacct cttcatcatg tccctggcca gcgccgacct ggtcatgggg ctgctggtgg    420
tgccgttcgg ggccaccatc gtggtgtggg gccgctggga gtacggctcc ttcttctgcg    480
agctgtggac ctcagtggac gtgctgtgcg tgacggccag catcgagacc ctgtgtgtca    540
ttgccctgga ccgctacctc gccatcacct cgcccttccg ctaccagagc ctgctgacgc    600
gcgcgcgggc gcggggcctc gtgtgcaccg tgtgggccat ctcggccctg gtgtccttcc    660
tgcccatcct catgcactgg tggcgggcgg agagcgacga ggcgcgccgc tgctacaacg    720
accccaagtg ctgcgacttc gtcaccaacc gggcctacgc catcgcctcg tccgtagtct    780
ccttctacgt gcccctgtgc atcatggcct tcgtgtacct gcgggtgttc cgcgaggccc    840
agaagcaggt gaagaagatc gacagctgcg agcgccgttt cctcggcggc ccagcgcggc    900
cgccctcgcc ctcgccctcg cccgtccccg cgcccgcgcc gccgcccgga cccccgcgcc    960
ccgccgccgc cgccgccacc gccccgctgg ccaacgggcg tgcgggtaag cggcggccct   1020
cgcgcctcgt ggccctgcgc gagcagaagg cgctcaagac gctgggcatc atcatgggcg   1080
tcttcacgct ctgctggctg cccttcttcc tggccaacgt ggtgaaggcc ttccaccgcg   1140
agctggtgcc cgaccgcctc ttcgtcttct tcaactggct gggctacgcc aactcggcct   1200
tcaaccccat catctactgc cgcagccccg acttccgcaa ggccttccag ggactgctct   1260
gctgcgcgcg cagggctgcc cgccggcgcc acgcgaccca cggagaccgg ccgcgcgcct   1320
cgggctgtct ggcccggccc ggacccccgc catcgcccgg ggccgcctcg gacgacgacg   1380
acgacgatgt cgtcggggcc acgccgcccg cgcgcctgct ggagccctgg gccggctgca   1440
acggcggggc ggcggcggac agcgactcga gcctggacga gccgtgccgc cccggcttcg   1500
cctcggaatc caaggtgtag ggcccggcgc ggggcgcgga ctccgggcac ggcttcccag   1560
gggaacgagg agatctgtgt ttacttaaga ccgatagcag gtgaactcga agcccacaat   1620
cctcgtctga atcatccgag gcaaagagaa aagccacgga ccgttgcaca aaaaggaaag   1680
tttgggaagg gatgggagag tggcttgctg atgttccttg ttgttttttt tttcttttct   1740
tttctttctt cttctttttt tttttttttt ttttttctgt ttgtggtccg gccttctttt   1800
gtgtgtgcgt gtgatgcatc tttagatttt tttcccccac caggtggttt ttgacactct   1860
ctgagaggac cggagtggaa gatgggtggg ttaggggaag ggagaagcat taggagggga   1920
ttaaaatcga tcatcgtggc tcccatccct ttcccgggaa caggaacaca ctaccagcca   1980
gagagaggag aatgacagtt tgtcaagaca tatttccttt tgctttccag agaaatttca   2040
ttttaatttc taagtaatga tttctgctgt tatgaaagca aagagaaagg atggaggcaa   2100
```

```
aataaaaaaa aatcacgttt caagaaatgt taagctcttc ttggaacaag ccccaccttg   2160

ctttccttgt gtagggcaaa cccgctgtcc cccgcgcgcc tgggtggtca ggctgaggga   2220

tttctacctc acactgtgca tttgcacagc agatagaaag acttgtttat attaaacagc   2280

ttatttatgt atcaatatta gttggaagga ccaggcgcag agcctctctc tgtgacatgt   2340

gactctgtca attgaagaca ggacattaaa agagagcgag agagagaaac agttcagatt   2400

actgcacatg tggataaaaa caaaaacaaa aaaaaggagt ggttcaaaat gccatttttg   2460

cacagtgtta ggaattacaa aatccacaga agatgttact tgcacaaaaa gaaattaaat   2520

atttttaaa gggagagggg ctgggcagat cttaaataaa attcaaactc tacttctgtt   2580

gtctagtatg ttattgagct aatgattcat tgggaaaata cctttttata ctcctttatc   2640

atggtactgt aactgtatcc atattataaa tataattatc ttaaggattt tttattttt   2700

tttatgtcca agtgcccacg tgaatttgct ggtgaaagtt agcacttgtg tgtaaattct   2760

acttcctctt gtgtgtttta ccaagtattt atactctggt gcaactaact actgtgtgag   2820

gaattggtcc atgtgcaata aataccaatg aagcacaatc aa                      2862


<210> SEQ ID NO 2
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = A or G

<400> SEQUENCE: 2

ctcgttgctg cctcccgcca gcgaangccc cgagccgctg tctcagcagt g              51


<210> SEQ ID NO 3
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or G

<400> SEQUENCE: 3

ccccgacttc cgcaaggcct tccagngact gctctgctgc gcgcgcaggg c              51


<210> SEQ ID NO 4
<211> LENGTH: 477
<212> TYPE: PRT
<213> ORGANISM: Homo sapiens

<400> SEQUENCE: 4

Met Gly Ala Gly Val Leu Val Leu Gly Ala Ser Glu Pro Gly Asn Leu
1               5                   10                  15

Ser Ser Ala Ala Pro Leu Pro Asp Gly Ala Ala Thr Ala Ala Arg Leu
            20                  25                  30

Leu Val Pro Ala Ser Pro Pro Ala Ser Leu Leu Pro Pro Ala Ser Glu
        35                  40                  45

Ser Pro Glu Pro Leu Ser Gln Gln Trp Thr Ala Gly Met Gly Leu Leu
    50                  55                  60

Met Ala Leu Ile Val Leu Leu Ile Val Ala Gly Asn Val Leu Val Ile
65                  70                  75                  80

Val Ala Ile Ala Lys Thr Pro Arg Leu Gln Thr Leu Thr Asn Leu Phe
```

```
                85                  90                  95

Ile Met Ser Leu Ala Ser Ala Asp Leu Val Met Gly Leu Leu Val Val
            100                 105                 110

Pro Phe Gly Ala Thr Ile Val Val Trp Gly Arg Trp Glu Tyr Gly Ser
        115                 120                 125

Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Ser Pro Phe Arg Tyr Gln Ser Leu Leu Thr Arg Ala Arg Ala Arg
                165                 170                 175

Gly Leu Val Cys Thr Val Trp Ala Ile Ser Ala Leu Val Ser Phe Leu
            180                 185                 190

Pro Ile Leu Met His Trp Trp Arg Ala Glu Ser Asp Glu Ala Arg Arg
        195                 200                 205

Cys Tyr Asn Asp Pro Lys Cys Cys Asp Phe Val Thr Asn Arg Ala Tyr
    210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                245                 250                 255

Lys Ile Asp Ser Cys Glu Arg Arg Phe Leu Gly Gly Pro Ala Arg Pro
            260                 265                 270

Pro Ser Pro Ser Pro Ser Pro Val Pro Ala Pro Ala Pro Pro Pro Gly
        275                 280                 285

Pro Pro Arg Pro Ala Ala Ala Ala Ala Thr Ala Pro Leu Ala Asn Gly
    290                 295                 300

Arg Ala Gly Lys Arg Arg Pro Ser Arg Leu Val Ala Leu Arg Glu Gln
305                 310                 315                 320

Lys Ala Leu Lys Thr Leu Gly Ile Ile Met Gly Val Phe Thr Leu Cys
                325                 330                 335

Trp Leu Pro Phe Phe Leu Ala Asn Val Val Lys Ala Phe His Arg Glu
            340                 345                 350

Leu Val Pro Asp Arg Leu Phe Val Phe Phe Asn Trp Leu Gly Tyr Ala
        355                 360                 365

Asn Ser Ala Phe Asn Pro Ile Ile Tyr Cys Arg Ser Pro Asp Phe Arg
    370                 375                 380

Lys Ala Phe Gln Gly Leu Leu Cys Cys Ala Arg Arg Ala Ala Arg Arg
385                 390                 395                 400

Arg His Ala Thr His Gly Asp Arg Pro Arg Ala Ser Gly Cys Leu Ala
                405                 410                 415

Arg Pro Gly Pro Pro Pro Ser Pro Gly Ala Ala Ser Asp Asp Asp Asp
            420                 425                 430

Asp Asp Val Val Gly Ala Thr Pro Pro Ala Arg Leu Leu Glu Pro Trp
        435                 440                 445

Ala Gly Cys Asn Gly Gly Ala Ala Ala Asp Ser Asp Ser Ser Leu Asp
    450                 455                 460

Glu Pro Cys Arg Pro Gly Phe Ala Ser Glu Ser Lys Val
465                 470                 475
```

<210> SEQ ID NO 5
<211> LENGTH: 2058
<212> TYPE: DNA
<213> ORGANISM: Homo sapiens

<400> SEQUENCE: 5

```
gcacataacg ggcagaacgc actgcgaagc ggcttcttca gagcacgggc tggaactggc     60
aggcaccgcg agcccctagc acccgacaag ctgagtgtgc aggacgagtc cccaccacac    120
ccacaccaca gccgctgaat gaggcttcca ggcgtccgct cgcggcccgc agagccccgc    180
cgtgggtccg cccgctgagg cgcccccagc cagtgcgctc acctgccaga ctgcgcgcca    240
tggggcaacc cgggaacggc agcgccttct tgctggcacc caatagaagc catgcgccgg    300
accacgacgt cacgcagcaa agggacgagg tgtgggtggt gggcatgggc atcgtcatgt    360
ctctcatcgt cctggccatc gtgtttggca atgtgctggt catcacagcc attgccaagt    420
tcgagcgtct gcagacggtc accaactact tcatcacttc actggcctgt gctgatctgg    480
tcatgggcct ggcagtggtg ccctttgggg ccgcccatat tcttatgaaa atgtggactt    540
ttggcaactt ctggtgcgag ttttggactt ccattgatgt gctgtgcgtc acggccagca    600
ttgagaccct gtgcgtgatc gcagtggatc gctactttgc cattacttca cctttcaagt    660
accagagcct gctgaccaag aataaggccc gggtgatcat tctgatggtg tggattgtgt    720
caggccttac ctccttcttg cccattcaga tgcactggta ccgggccacc caccaggaag    780
ccatcaactg ctatgccaat gagacctgct gtgacttctt cacgaaccaa gcctatgcca    840
ttgcctcttc catcgtgtcc ttctacgttc ccctggtgat catggtcttc gtctactcca    900
gggtctttca ggaggccaaa aggcagctcc agaagattga caaatctgag ggccgcttcc    960
atgtccagaa ccttagccag gtggagcagg atgggcggac ggggcatgga ctccgcagat   1020
cttccaagtt ctgcttgaag gagcacaaag ccctcaagac gttaggcatc atcatgggca   1080
ctttcaccct ctgctggctg cccttcttca tcgttaacat tgtgcatgtg atccaggata   1140
acctcatccg taaggaagtt tacatcctcc taaattggat aggctatgtc aattctggtt   1200
tcaatcccct tatctactgc cggagcccag atttcaggat tgccttccag gagcttctgt   1260
gcctgcgcag gtcttctttg aaggcctatg ggaatggcta ctccagcaac ggcaacacag   1320
gggagcagag tggatatcac gtggaacagg agaaagaaaa taaactgctg tgtgaagacc   1380
tcccaggcac ggaagacttt gtgggccatc aaggtactgt gcctagcgat aacattgatt   1440
cacaagggag gaattgtagt acaaatgact cactgctgta aagcagtttt tctactttta   1500
aagacccccc cccccaacag aacactaaac agactattta acttgagggt aataaactta   1560
gaataaaatt gtaaaattgt atagagatat gcagaaggaa gggcatcctt ctgccttttt   1620
tattttttta agctgtaaaa agagagaaaa cttatttgag tgattatttg ttatttgtac   1680
agttcagttc ctctttgcat ggaatttgta agtttatgtc taaagagctt tagtcctaga   1740
ggacctgagt ctgctatatt ttcatgactt ttccatgtat ctacctcact attcaagtat   1800
taggggtaat atattgctgc tggtaatttg tatctgaagg agattttcct tcctacaccc   1860
ttggacttga ggattttgag tatctcggac ctttcagctg tgaacatgga ctcttccccc   1920
actcctctta tttgctcaca cggggtattt taggcaggga tttgaggagc agcttcagtt   1980
gttttcccga gcaaagtcta aagtttacag taaataaatt gtttgaccat gccttcattg   2040
caaaaaaaaa aaaaaaaa                                                 2058
```

<210> SEQ ID NO 6
<211> LENGTH: 51
<212> TYPE: DNA
<213> ORGANISM: Homo sapiens
<220> FEATURE:

```
<221> NAME/KEY: misc_feature
<222> LOCATION: 26
<223> OTHER INFORMATION: n = A or G

<400> SEQUENCE: 6

cagcgccttc ttgctggcac ccaatngaag ccatgcgccg gaccacgacg t              51


<210> SEQ ID NO 7
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or G

<400> SEQUENCE: 7

tgcgccggac cacgacgtca cgcagnaaag ggacgaggtg tgggtggtgg g              51


<210> SEQ ID NO 8
<211> LENGTH: 413
<212> TYPE: PRT
<213> ORGANISM: Homo sapiens

<400> SEQUENCE: 8

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
```

```
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
    290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
        355                 360                 365

Glu Gln Glu Lys Glu Asn Lys Leu Leu Cys Glu Asp Leu Pro Gly Thr
    370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410


<210> SEQ ID NO 9
<211> LENGTH: 1673
<212> TYPE: DNA
<213> ORGANISM: Homo sapiens

<400> SEQUENCE: 9

gtgctgagag tgtcctgcct ggtcctctgt gcctggtggg gtgggggtgc caggtgtgtc      60

cagaggagcc catttggtag tgaggcaggt atggggctag aagcactggt gcccctggcc     120

gtgatagtgg ccatcttcct gctcctggtg gacctgatgc accggcgcca acgctgggct     180

gcacgctacc caccaggccc cctgccactg cccgggctgg gcaacctgct gcatgtggac     240

ttccagaaca caccatactg cttcgaccag ttgcggcgcc gcttcgggga cgtgttcagc     300

ctgcagctgg cctggacgcc ggtggtcgtg ctcaatgggc tggcggccgt gcgcgaggcg     360

ctggtgaccc acggcgagga caccgccgac cgcccgcctg tgcccatcac ccagatcctg     420

ggtttcgggc cgcgttccca aggggtgttc ctggcgcgct atgggcccgc gtggcgcgag     480

cagaggcgct tctccgtgtc caccttgcgc aacttgggcc tgggcaagaa gtcgctggag     540

cagtgggtga ccgaggaggc cgcctgcctt tgtgccgcct tcgccaacca ctccggacgc     600

ccctttcgcc ccaacggtct cttggacaaa gccgtgagca acgtgatcgc ctccctcacc     660

tgcgggcgcc gcttcgagta cgacgaccct cgcttcctca ggctgctgga cctagctcag     720

gagggactga aggaggagtc gggctttctg cgcgaggtgc tgaatgctgt ccccgtcctc     780

ctgcatatcc cagcgctggc tggcaaggtc ctacgcttcc aaaaggcttt cctgacccag     840

ctggatgagc tgctaactga gcacaggatg acctgggacc cagcccagcc cccccgagac     900

ctgactgagg ccttcctggc agagatggag aaggccaagg ggaaccctga gagcagcttc     960

aatgatgaga acctgcgcat agtggtggct gacctgttct ctgccgggat ggtgaccacc    1020

tcgaccacgc tggcctgggg cctcctgctc atgatcctac atccggatgt gcagcgccgt    1080

gtccaacagg agatcgacga cgtgataggg caggtgcggc gaccagagat gggtgaccag    1140

gctcacatgc cctacaccac tgccgtgatt catgaggtgc agcgctttgg ggacatcgtc    1200

cccctgggtg tgacccatat gacatcccgt gacatcgaag tacagggctt ccgcatccct    1260
```

```
aagggaacga cactcatcac caacctgtca tcggtgctga aggatgaggc cgtctgggag   1320

aagcccttcc gcttccaccc cgaacacttc ctggatgccc agggccactt tgtgaagccg   1380

gaggccttcc tgcctttctc agcaggccgc cgtgcatgcc tcggggagcc cctggcccgc   1440

atggagctct tcctcttctt cacctccctg ctgcagcact tcagcttctc ggtgcccact   1500

ggacagcccc ggcccagcca ccatggtgtc tttgctttcc tggtgagccc atccccctat   1560

gagctttgtg ctgtgccccg ctagaatggg gtacctagtc cccagcctgc tccctagcca   1620

gaggctctaa tgtacaataa agcaatgtgg tagttccaaa aaaaaaaaaa aaa          1673
```

<210> SEQ ID NO 10
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = A or G

<400> SEQUENCE: 10

```
cccttacccg catctcccac ccccangacg cccctttcgc cccaacggtc t              51
```

<210> SEQ ID NO 11
<211> LENGTH: 497
<212> TYPE: PRT
<213> ORGANISM: Homo sapiens

<400> SEQUENCE: 11

```
Met Gly Leu Glu Ala Leu Val Pro Leu Ala Val Ile Val Ala Ile Phe
1               5                   10                  15

Leu Leu Leu Val Asp Leu Met His Arg Arg Gln Arg Trp Ala Ala Arg
            20                  25                  30

Tyr Pro Pro Gly Pro Leu Pro Leu Pro Gly Leu Gly Asn Leu Leu His
        35                  40                  45

Val Asp Phe Gln Asn Thr Pro Tyr Cys Phe Asp Gln Leu Arg Arg Arg
    50                  55                  60

Phe Gly Asp Val Phe Ser Leu Gln Leu Ala Trp Thr Pro Val Val Val
65                  70                  75                  80

Leu Asn Gly Leu Ala Ala Val Arg Glu Ala Leu Val Thr His Gly Glu
                85                  90                  95

Asp Thr Ala Asp Arg Pro Pro Val Pro Ile Thr Gln Ile Leu Gly Phe
            100                 105                 110

Gly Pro Arg Ser Gln Gly Val Phe Leu Ala Arg Tyr Gly Pro Ala Trp
        115                 120                 125

Arg Glu Gln Arg Arg Phe Ser Val Ser Thr Leu Arg Asn Leu Gly Leu
    130                 135                 140

Gly Lys Lys Ser Leu Glu Gln Trp Val Thr Glu Glu Ala Ala Cys Leu
145                 150                 155                 160

Cys Ala Ala Phe Ala Asn His Ser Gly Arg Pro Phe Arg Pro Asn Gly
                165                 170                 175

Leu Leu Asp Lys Ala Val Ser Asn Val Ile Ala Ser Leu Thr Cys Gly
            180                 185                 190

Arg Arg Phe Glu Tyr Asp Asp Pro Arg Phe Leu Arg Leu Leu Asp Leu
        195                 200                 205

Ala Gln Glu Gly Leu Lys Glu Glu Ser Gly Phe Leu Arg Glu Val Leu
    210                 215                 220

Asn Ala Val Pro Val Leu Leu His Ile Pro Ala Leu Ala Gly Lys Val
```

```
225                 230                 235                 240

Leu Arg Phe Gln Lys Ala Phe Leu Thr Gln Leu Asp Glu Leu Leu Thr
                245                 250                 255

Glu His Arg Met Thr Trp Asp Pro Ala Gln Pro Pro Arg Asp Leu Thr
            260                 265                 270

Glu Ala Phe Leu Ala Glu Met Glu Lys Ala Lys Gly Asn Pro Glu Ser
        275                 280                 285

Ser Phe Asn Asp Glu Asn Leu Arg Ile Val Val Ala Asp Leu Phe Ser
    290                 295                 300

Ala Gly Met Val Thr Thr Ser Thr Thr Leu Ala Trp Gly Leu Leu Leu
305                 310                 315                 320

Met Ile Leu His Pro Asp Val Gln Arg Arg Val Gln Gln Glu Ile Asp
                325                 330                 335

Asp Val Ile Gly Gln Val Arg Arg Pro Glu Met Gly Asp Gln Ala His
            340                 345                 350

Met Pro Tyr Thr Thr Ala Val Ile His Glu Val Gln Arg Phe Gly Asp
        355                 360                 365

Ile Val Pro Leu Gly Val Thr His Met Thr Ser Arg Asp Ile Glu Val
    370                 375                 380

Gln Gly Phe Arg Ile Pro Lys Gly Thr Thr Leu Ile Thr Asn Leu Ser
385                 390                 395                 400

Ser Val Leu Lys Asp Glu Ala Val Trp Glu Lys Pro Phe Arg Phe His
                405                 410                 415

Pro Glu His Phe Leu Asp Ala Gln Gly His Phe Val Lys Pro Glu Ala
            420                 425                 430

Phe Leu Pro Phe Ser Ala Gly Arg Arg Ala Cys Leu Gly Glu Pro Leu
        435                 440                 445

Ala Arg Met Glu Leu Phe Leu Phe Phe Thr Ser Leu Leu Gln His Phe
    450                 455                 460

Ser Phe Ser Val Pro Thr Gly Gln Pro Arg Pro Ser His His Gly Val
465                 470                 475                 480

Phe Ala Phe Leu Val Ser Pro Ser Pro Tyr Glu Leu Cys Ala Val Pro
                485                 490                 495

Arg
```

<210> SEQ ID NO 12
<211> LENGTH: 100
<212> TYPE: DNA
<213> ORGANISM: Artificial Sequence
<220> FEATURE:
<223> OTHER INFORMATION: A synthetic oligonucleotide

<400> SEQUENCE: 12

```
tcccatttct ctagacctgc tgcctataca gtcacttttt tttttttttt gagacggagt     60

ctcgctctgt cgcccataca gtcactttta tgtggtttcg                          100
```

<210> SEQ ID NO 13
<211> LENGTH: 2587
<212> TYPE: DNA
<213> ORGANISM: Homo sapiens

<400> SEQUENCE: 13

```
atcccatgag cgggcagcag ggtcagaagt ggcccccgtg ttgcctaagc aagactctcc     60

cctgccctct gccctctgca cctccggcct gcatgtccct gtggcctctt gggggtacat    120

ctcccggggc tgggtcagaa ggcctgggtg gttggcctca ggctgtcaca cacctaggga    180
```

```
gatgctcccg tttctgggaa ccttggcccc gactcctgca aacttcggta aatgtgtaac    240
tcgaccctgc accggctcac tctgttcagc agtgaaactc tgcatcgatc actaagactt    300
cctggaagag gtcccagcgt gagtgtcgct tctggcatct gtccttctgg ccagcctgtg    360
gtctggccaa gtgatgtaac cctcctctcc agcctgtgca caggcagcct gggaacagct    420
ccatccccac ccctcagcta taaatagggc atcgtgaccc ggccggggga agaagctgcc    480
gttgttctgg gtactacagc agaagggtat gcggaagcga gcaccccagt ctgagatggc    540
tcctgccggt gtgagcctga gggccaccat cctctgcctc ctggcctggg ctggcctggc    600
tgcaggtgac cgggtgtaca tacacccctt ccacctcgtc atccacaatg agagtacctg    660
tgagcagctg gcaaaggcca atgccgggaa gcccaaagac ccccaccttca tacctgctcc    720
aattcaggcc aagacatccc ctgtggatga aaaggcccta caggaccagc tggtgctagt    780
cgctgcaaaa cttgacaccg aagacaagtt gagggccgca atggtcggga tgctggccaa    840
cttcttgggc ttccgtatat atggcatgca cagtgagcta tggggcgtgg tccatggggc    900
caccgtcctc tccccaacgg ctgtctttgg caccctggcc tctctctatc tgggagcctt    960
ggaccacaca gctgacaggc tacaggcaat cctgggtgtt ccttggaagg acaagaactg   1020
cacctcccgg ctggatgcgc acaaggtcct gtctgccctg caggctgtac agggcctgct   1080
agtggcccag ggcagggctg atagccaggc ccagctgctg ctgtccacgg tggtgggcgt   1140
gttcacagcc ccaggcctgc acctgaagca gccgtttgtg cagggcctgg ctctctatac   1200
ccctgtggtc ctcccacgct ctctggactt cacagaactg gatgttgctg ctgagaagat   1260
tgacaggttc atgcaggctg tgacaggatg gaagactggc tgctccctga tgggagccag   1320
tgtggacagc accctggctt tcaacaccta cgtccacttc caagggaaga tgaagggctt   1380
ctccctgctg gccgagcccc aggagttctg ggtggacaac agcacctcag tgtctgttcc   1440
catgctctct ggcatgggca ccttccagca ctggagtgac atccaggaca acttctcggt   1500
gactcaagtg cccttcactg agagcgcctg cctgctgctg atccagcctc actatgcctc   1560
tgacctggac aaggtggagg gtctcacttt ccagcaaaac tccctcaact ggatgaagaa   1620
actatctccc cggaccatcc acctgaccat gccccaactg gtgctgcaag gatcttatga   1680
cctgcaggac ctgctcgccc aggctgagct gcccgccatt ctgcacaccg agctgaacct   1740
gcaaaaattg agcaatgacc gcatcagggt gggggaggtg ctgaacagca ttttttttga   1800
gcttgaagcg gatgagagag agcccacaga gtctacccaa cagcttaaca agcctgaggt   1860
cttggaggtg accctgaacc gcccattcct gtttgctgtg tatgatcaaa gcgccactgc   1920
cctgcacttc ctgggccgcg tggccaaccc gctgagcaca gcatgaggcc agggccccag   1980
aacacagtgc ctggcaaggc ctctgcccct ggcctttgag gcaaaggcca gcagcagata   2040
acaaccccgg acaaatcagc gatgtgtcac cccagtctc ccacctttttc ttctaatgag   2100
tcgactttga gctggaaagc agccgtttct ccttggtcta agtgtgctgc atggagtgag   2160
cagtagaagc ctgcagcggc acaaatgcac ctcccagttt gctgggttta ttttagagaa   2220
tgggggtggg gaggcaagaa ccagtgttta gcgcgggact actgttccaa aaagaattcc   2280
aaccgaccag cttgtttgtg aaacaaaaaa gtgttccctt ttcaagttga gaacaaaaat   2340
tgggttttaa aattaaagta tacatttttg cattgccttc ggtttgtatt tagtgtcttg   2400
aatgtaagaa catgacctcc gtgtagtgtc tgtaatacct tagtttttttc cacagatgct   2460
tgtgattttt gaacaatacg tgaaagatgc aagcacctga atttctgttt gaatgcggaa   2520
```

```
ccatagctgg ttatttctcc cttgtgttag taataaacgt cttgccacaa taagcctcca   2580

aaaaaaa                                                             2587


<210> SEQ ID NO 14
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or T

<400> SEQUENCE: 14

ggatggaaga ctggctgctc cctganggga gccagtgtgg acagcaccct g              51


<210> SEQ ID NO 15
<211> LENGTH: 485
<212> TYPE: PRT
<213> ORGANISM: Homo sapiens

<400> SEQUENCE: 15

Met Arg Lys Arg Ala Pro Gln Ser Glu Met Ala Pro Ala Gly Val Ser
1               5                   10                  15

Leu Arg Ala Thr Ile Leu Cys Leu Leu Ala Trp Ala Gly Leu Ala Ala
            20                  25                  30

Gly Asp Arg Val Tyr Ile His Pro Phe His Leu Val Ile His Asn Glu
        35                  40                  45

Ser Thr Cys Glu Gln Leu Ala Lys Ala Asn Ala Gly Lys Pro Lys Asp
    50                  55                  60

Pro Thr Phe Ile Pro Ala Pro Ile Gln Ala Lys Thr Ser Pro Val Asp
65                  70                  75                  80

Glu Lys Ala Leu Gln Asp Gln Leu Val Leu Val Ala Ala Lys Leu Asp
                85                  90                  95

Thr Glu Asp Lys Leu Arg Ala Ala Met Val Gly Met Leu Ala Asn Phe
            100                 105                 110

Leu Gly Phe Arg Ile Tyr Gly Met His Ser Glu Leu Trp Gly Val Val
        115                 120                 125

His Gly Ala Thr Val Leu Ser Pro Thr Ala Val Phe Gly Thr Leu Ala
    130                 135                 140

Ser Leu Tyr Leu Gly Ala Leu Asp His Thr Ala Asp Arg Leu Gln Ala
145                 150                 155                 160

Ile Leu Gly Val Pro Trp Lys Asp Lys Asn Cys Thr Ser Arg Leu Asp
                165                 170                 175

Ala His Lys Val Leu Ser Ala Leu Gln Ala Val Gln Gly Leu Leu Val
            180                 185                 190

Ala Gln Gly Arg Ala Asp Ser Gln Ala Gln Leu Leu Leu Ser Thr Val
        195                 200                 205

Val Gly Val Phe Thr Ala Pro Gly Leu His Leu Lys Gln Pro Phe Val
    210                 215                 220

Gln Gly Leu Ala Leu Tyr Thr Pro Val Val Leu Pro Arg Ser Leu Asp
225                 230                 235                 240

Phe Thr Glu Leu Asp Val Ala Ala Glu Lys Ile Asp Arg Phe Met Gln
                245                 250                 255

Ala Val Thr Gly Trp Lys Thr Gly Cys Ser Leu Met Gly Ala Ser Val
            260                 265                 270

Asp Ser Thr Leu Ala Phe Asn Thr Tyr Val His Phe Gln Gly Lys Met
        275                 280                 285
```

```
Lys Gly Phe Ser Leu Leu Ala Glu Pro Gln Glu Phe Trp Val Asp Asn
    290                 295                 300

Ser Thr Ser Val Ser Val Pro Met Leu Ser Gly Met Gly Thr Phe Gln
305                 310                 315                 320

His Trp Ser Asp Ile Gln Asp Asn Phe Ser Val Thr Gln Val Pro Phe
                325                 330                 335

Thr Glu Ser Ala Cys Leu Leu Leu Ile Gln Pro His Tyr Ala Ser Asp
            340                 345                 350

Leu Asp Lys Val Glu Gly Leu Thr Phe Gln Gln Asn Ser Leu Asn Trp
        355                 360                 365

Met Lys Lys Leu Ser Pro Arg Thr Ile His Leu Thr Met Pro Gln Leu
    370                 375                 380

Val Leu Gln Gly Ser Tyr Asp Leu Gln Asp Leu Leu Ala Gln Ala Glu
385                 390                 395                 400

Leu Pro Ala Ile Leu His Thr Glu Leu Asn Leu Gln Lys Leu Ser Asn
                405                 410                 415

Asp Arg Ile Arg Val Gly Glu Val Leu Asn Ser Ile Phe Phe Glu Leu
            420                 425                 430

Glu Ala Asp Glu Arg Glu Pro Thr Glu Ser Thr Gln Gln Leu Asn Lys
        435                 440                 445

Pro Glu Val Leu Glu Val Thr Leu Asn Arg Pro Phe Leu Phe Ala Val
    450                 455                 460

Tyr Asp Gln Ser Ala Thr Ala Leu His Phe Leu Gly Arg Val Ala Asn
465                 470                 475                 480

Pro Leu Ser Thr Ala
                485


<210> SEQ ID NO 16
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = A or C

<400> SEQUENCE: 16

tgcagcactt cactaccaaa tgagcnttag ctacttttca gaattgaagg a              51


<210> SEQ ID NO 17
<211> LENGTH: 720
<212> TYPE: DNA
<213> ORGANISM: Homo sapiens

<400> SEQUENCE: 17

attcaactag gcatcatacg tgactgtaga attgcagata ttgtggacac ggccatgcct     60

atcaccattt gtatagctta ttttaacaat tgcctgaatc ctctttttta tggctttctg    120

gggaaaaaat ttaaaagata ttttctccag cttctaaaat atattccccc aaaagccaaa    180

tcccactcaa acctttcaac aaaaatgagc acgctttcct accgcccctc agataatgta    240

agctcatcca ccaagaagcc tgcaccatgt tttgaggttg agtgacatgt tcgaaacctg    300

tccataaagt aattttgtga aagaaggagc aagagaacat tcctctgcag cacttcacta    360

ccaaatgagc attagctact tttcagaatt gaaggagaaa atgcattatg tggactgaac    420

cgacttttct aaagctctga acaaaagctt ttctttcctt ttgcaacaag acaaagcaaa    480

gccacatttt gcattagaca gatgacggct gctcgaagaa caatgtcaga aactcgatga    540
```

```
atgtgttgat ttgagaaatt ttactgacag aaatgcaatc tccctagcct gcttttgtcc    600

tgttattttt tatttccaca taaaggtatt tagaatatat taaatcgtta gaggagcaac    660

aggagatgag agttccagat tgttctgtcc agtttccaaa gggcagtaaa gttttcgtgc    720
```

<210> SEQ ID NO 18
<211> LENGTH: 2185
<212> TYPE: DNA
<213> ORGANISM: Homo sapiens

<400> SEQUENCE: 18

```
ggcagcagcg agtgacagga cgtctggacc ggcgcgccgc tagcagctct gccgggccgc     60

ggcggtgatc gatgggagcg gctggagcgg acccagcgag tgagggcgca cagccggacg    120

ccgaggcggc gggcgggaga ccgcaccgcg acgccggccc tcggcggacg agtcgagcgc    180

ccgggcgcgg gtgtatttga tatagtgttt gcaacaaatt cgacccaggt gatcaaaatg    240

attctcaact cttctactga agatggtatt aaaagaatcc aagatgattg tcccaaagct    300

ggaaggcata attacatatt tgtcatgatt cctactttat acagtatcat ctttgtggtg    360

ggaatatttg gaaacagctt ggtggtgata gtcatttact tttatatgaa gctgaagact    420

gtggccagtg tttttctttt gaatttagca ctggctgact tatgcttttt actgactttg    480

ccactatggg ctgtctacac agctatggaa taccgctggc cctttggcaa ttacctatgt    540

aagattgctt cagccagcgt cagtttcaac ctgtacgcta gtgtgtttct actcacgtgt    600

ctcagcattg atcgatacct ggctattgtt cacccaatga agtcccgcct tcgacgcaca    660

atgcttgtag ccaaagtcac ctgcatcatc atttggctgc tggcaggctt ggccagtttg    720

ccagctataa tccatcgaaa tgtatttttc attgagaaca ccaatattac agtttgtgct    780

ttccattatg agtcccaaaa ttcaaccctc ccgatagggc tgggcctgac caaaaatata    840

ctgggtttcc tgtttccttt tctgatcatt cttacaagtt atactcttat ttggaaggcc    900

ctaaagaagg cttatgaaat tcagaagaac aaaccaagaa atgatgatat ttttaagata    960

attatggcaa ttgtgctttt ctttttcttt tcctggattc cccaccaaat attcactttt   1020

ctggatgtat tgattcaact aggcatcata cgtgactgta gaattgcaga tattgtggac   1080

acggccatgc ctatcaccat ttgtatagct tattttaaca attgcctgaa tcctcttttt   1140

tatggctttc tggggaaaaa atttaaaaga tattttctcc agcttctaaa atatattccc   1200

ccaaaagcca aatcccactc aaacctttca acaaaaatga gcacgctttc ctaccgcccc   1260

tcagataatg taagctcatc caccaagaag cctgcaccat gttttgaggt tgagtgacat   1320

gttcgaaacc tgtccataaa gtaattttgt gaaagaagga gcaagagaac attcctctgc   1380

agcacttcac taccaaatga gcattagcta cttttcagaa ttgaaggaga aaatgcatta   1440

tgtggactga accgactttt ctaaagctct gaacaaaagc ttttctttcc ttttgcaaca   1500

agacaaagca aagccacatt ttgcattaga cagatgacgg ctgctcgaag aacaatgtca   1560

gaaactcgat gaatgtgttg atttgagaaa ttttactgac agaaatgcaa tctccctagc   1620

ctgcttttgt cctgttattt tttatttcca cataaaggta tttagaatat attaactcgt   1680

tagaggagca acaggagatg agagttccag attgttctgt ccagtttcca aagggcagta   1740

aagttttcgt gcctgttttc agctattagc aactgtgcct acacttgcac ctggtctgca   1800

cattttgtac aaagatatgc ttaagcagta gtcgtcaagt tgcagatctt tgttgtgaaa   1860

ttcaacctgt gtcttatagg tttacactgc caaaacaatg cccgtaagat ggcttatttg   1920
```

```
tataatggtg ttacctaaag tcacatataa aagttaaact acttgtaaag gtgctgcact   1980

ggtcccaagt agtagtgtct tcctagtata ttagtttgat ttaatatctg agaagtgtat   2040

atagtttgtg gtaaaaagat tatatatcat aaagtatgcc ttcctgttta aaaaaagtat   2100

atattctaca catatatgta tatgtatatc tatatctcta aactgctgtt aattgattaa   2160

aatctggcaa agttatattt acccc                                         2185


<210> SEQ ID NO 19
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = A or G

<400> SEQUENCE: 19

agaacaccaa agcaggctta atctgngggc acttacagag actgctttaa a              51


<210> SEQ ID NO 20
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or T

<400> SEQUENCE: 20

tttaaagcag tctctgtaag tgcccncaga ttaagcctgc tttggtgttc t              51


<210> SEQ ID NO 21
<211> LENGTH: 3497
<212> TYPE: DNA
<213> ORGANISM: Homo sapiens

<400> SEQUENCE: 21

aaacagaagg cagatagaga gggagtgaga ggcaggagct gagacacaga tcctggagga     60

agaagaccaa aggaaggggg cagagacaga aagggaggtg ctaggacaaa actcgaaagg    120

tggccctatc agggaagcag aggagaggcc gttctaggga agcccagctc cggcactttt    180

ggccccaact cccgcaggtc tgctggctcc aggaaaggtg gaggagggag ggaggagtgg    240

gagaatgtgg gcgcagggtg ggacatgggc atggccaggg gcagcctcac tcgggttcca    300

ggggtgatgg gagagggcac tcagggccca gagctcagcc ttgaccctga cccttgctct    360

ccccaatcca ctccggggct catgaagggg aacaagctgg aggagcagga ccctagacct    420

ctgcagccca taccaggtct catggagggg aacaagctgg aggagcagga ctctagccct    480

ccacagtcca ctccagggct catgaagggg aacaagcgtg aggagcaggg gctgggcccc    540

gaacctgcgg cgccccagca gcccacggcg gaggaggagg ccctgatcga gttccaccgc    600

tcctaccgag agctcttcga gttcttctgc aacaacacca ccatccacgg cgccatccgc    660

ctggtgtgct cccagcacaa ccgcatgaag acggccttct gggcagtgct gtggctctgc    720

acctttggca tgatgtactg gcaattcggc ctgcttttcg gagagtactt cagctacccc    780

gtcagcctca acatcaacct caactcggac aagctcgtct tccccgcagt gaccatctgc    840

accctcaatc cctacaggta cccggaaatt aaagaggagc tggaggagct ggaccgcatc    900

acagagcaga cgctctttga cctgtacaaa tacagctcct tcaccactct cgtggccggc    960

tcccgcagcc gtcgcgacct gcgggggact ctgccgcacc ccttgcagcg cctgagggtc   1020
```

```
ccgcccccgc ctcacggggc ccgtcgagcc cgtagcgtgg cctccagctt gcgggacaac   1080

aacccccagg tggactggaa ggactggaag atcggcttcc agctgtgcaa ccagaacaaa   1140

tcggactgct tctaccagac atactcatca ggggtggatg cggtgaggga gtggtaccgc   1200

ttccactaca tcaacatcct gtcgaggctg ccagagactc tgccatccct ggaggaggac   1260

acgctgggca acttcatctt cgcctgccgc ttcaaccagg tctcctgcaa ccaggcgaat   1320

tactctcact tccaccaccc gatgtatgga aactgctata ctttcaatga caagaacaac   1380

tccaacctct ggatgtcttc catgcctgga atcaacaacg gtctgtccct gatgctgcgc   1440

gcagagcaga atgacttcat tcccctgctg tccacagtga ctggggcccg ggtaatggtg   1500

cacgggcagg atgaacctgc ctttatggat gatggtggct ttaacttgcg gcctggcgtg   1560

gagacctcca tcagcatgag gaaggaaacc ctggacagac ttgggggcga ttatggcgac   1620

tgcaccaaga atggcagtga tgttcctgtt gagaaccttt acccttcaaa gtacacacag   1680

caggtgtgta ttcactcctg cttccaggag agcatgatca aggagtgtgg ctgtgcctac   1740

atcttctatc cgcggcccca gaacgtggag tactgtgact acagaaagca cagttcctgg   1800

gggtactgct actataagct ccaggttgac ttctcctcag accacctggg ctgtttcacc   1860

aagtgccgga agccatgcag cgtgaccagc taccagctct ctgctggtta ctcacgatgg   1920

ccctcggtga catcccagga atgggtcttc cagatgctat cgcgacagaa caattacacc   1980

gtcaacaaca agagaaatgg agtggccaaa gtcaacatct tcttcaagga gctgaactac   2040

aaaaccaatt ctgagtctcc ctctgtcacg atggtcaccc tcctgtccaa cctgggcagc   2100

cagtggagcc tgtggttcgg ctcctcggtg ttgtctgtgg tggagatggc tgagctcgtc   2160

tttgacctgc tggtcatcat gttcctcatg ctgctccgaa ggttccgaag ccgatactgg   2220

tctccaggcc gagggggcag ggtgctcag gaggtagcct ccaccctggc atcctcccct   2280

ccttcccact tctgccccca ccccatgtct ctgtccttgt cccagccagg ccctgctccc   2340

tctccagcct tgacagcccc tccccctgcc tatgccaccc tgggcccccg cccatctcca   2400

gggggctctg caggggccag ttcctccacc tgtcctctgg gggggccctg agagggaagg   2460

agaggtttct cacaccaagg cagatgctcc tctggtggga gggtgctggc cctggcaaga   2520

ttgaaggatg tgcagggctt cctctcagag ccgcccaaac tgccgttgat gtgtggaggg   2580

gaagcaagat gggtaagggc tcaggaagtt gctccaagaa cagtagctga tgaagctgcc   2640

cagaagtgcc ttggctccag ccctgtaccc cttggtactg cctctgaaca ctctggtttc   2700

cccacccaac tgcggctaag tctctttttc ccttggatca gccaagcgaa acttggagct   2760

ttgacaagga actttcctaa gaaaccgctg ataaccagga caaaacacaa ccaagggtac   2820

acgcaggcat gcacgggttt cctgcccagc gacggcttaa gccagccccc gactggcctg   2880

gccacactgc tctccagtag cacagatgtc tgctcctcct cttgaacttg ggtgggaaac   2940

cccacccaaa agcccccttt gttacttagg caattcccct tccctgactc ccgagggcta   3000

gggctagagc agacccgggt aagtaaaggc agacccaggg ctcctctagc ctcatacccg   3060

tgccctcaca gagccatgcc ccggcacctc tgccctgtgt ctttcatacc tctacatgtc   3120

tgcttgagat atttcctcag cctgaaagtt tccccaacca tctgccagag aactcctatg   3180

catcccttag aaccctgctc agacaccatt acttttgtga acgcttctgc cacatcttgt   3240

cttccccaaa attgatcact ccgccttctc ctgggctccc gtagcacact ataacatctg   3300

ctggagtgtt gctgttgcac catactttct tgtacatttg tgtctccctt cccaactaga   3360
```

```
ctgtaagtgc cttgcggtca gggactgaat cttgcccgtt tatgtatgct ccatgtctag   3420

cccatcatcc tgcttggagc aagtaggcag gagctcaata aatgtttgtt gcatgaagga   3480

aaaaaaaaaa aaaaaaa                                                  3497


<210> SEQ ID NO 22
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = A or G

<400> SEQUENCE: 22

gggctctgca ggggccagtt cctccncctg tcctctgggg gggccctgag a              51


<210> SEQ ID NO 23
<211> LENGTH: 728
<212> TYPE: PRT
<213> ORGANISM: Homo sapiens

<400> SEQUENCE: 23

Met Gly Met Ala Arg Gly Ser Leu Thr Arg Val Pro Gly Val Met Gly
1               5                   10                  15

Glu Gly Thr Gln Gly Pro Glu Leu Ser Leu Asp Pro Asp Pro Cys Ser
            20                  25                  30

Pro Gln Ser Thr Pro Gly Leu Met Lys Gly Asn Lys Leu Glu Glu Gln
        35                  40                  45

Asp Pro Arg Pro Leu Gln Pro Ile Pro Gly Leu Met Glu Gly Asn Lys
    50                  55                  60

Leu Glu Glu Gln Asp Ser Ser Pro Pro Gln Ser Thr Pro Gly Leu Met
65                  70                  75                  80

Lys Gly Asn Lys Arg Glu Glu Gln Gly Leu Gly Pro Glu Pro Ala Ala
                85                  90                  95

Pro Gln Gln Pro Thr Ala Glu Glu Glu Ala Leu Ile Glu Phe His Arg
            100                 105                 110

Ser Tyr Arg Glu Leu Phe Glu Phe Phe Cys Asn Asn Thr Thr Ile His
        115                 120                 125

Gly Ala Ile Arg Leu Val Cys Ser Gln His Asn Arg Met Lys Thr Ala
    130                 135                 140

Phe Trp Ala Val Leu Trp Leu Cys Thr Phe Gly Met Met Tyr Trp Gln
145                 150                 155                 160

Phe Gly Leu Leu Phe Gly Glu Tyr Phe Ser Tyr Pro Val Ser Leu Asn
                165                 170                 175

Ile Asn Leu Asn Ser Asp Lys Leu Val Phe Pro Ala Val Thr Ile Cys
            180                 185                 190

Thr Leu Asn Pro Tyr Arg Tyr Pro Glu Ile Lys Glu Glu Leu Glu Glu
        195                 200                 205

Leu Asp Arg Ile Thr Glu Gln Thr Leu Phe Asp Leu Tyr Lys Tyr Ser
    210                 215                 220

Ser Phe Thr Thr Leu Val Ala Gly Ser Arg Ser Arg Arg Asp Leu Arg
225                 230                 235                 240

Gly Thr Leu Pro His Pro Leu Gln Arg Leu Arg Val Pro Pro Pro Pro
                245                 250                 255

His Gly Ala Arg Arg Ala Arg Ser Val Ala Ser Ser Leu Arg Asp Asn
            260                 265                 270
```

```
Asn Pro Gln Val Asp Trp Lys Asp Trp Lys Ile Gly Phe Gln Leu Cys
        275                 280                 285

Asn Gln Asn Lys Ser Asp Cys Phe Tyr Gln Thr Tyr Ser Ser Gly Val
    290                 295                 300

Asp Ala Val Arg Glu Trp Tyr Arg Phe His Tyr Ile Asn Ile Leu Ser
305                 310                 315                 320

Arg Leu Pro Glu Thr Leu Pro Ser Leu Glu Glu Asp Thr Leu Gly Asn
                325                 330                 335

Phe Ile Phe Ala Cys Arg Phe Asn Gln Val Ser Cys Asn Gln Ala Asn
            340                 345                 350

Tyr Ser His Phe His His Pro Met Tyr Gly Asn Cys Tyr Thr Phe Asn
        355                 360                 365

Asp Lys Asn Asn Ser Asn Leu Trp Met Ser Ser Met Pro Gly Ile Asn
    370                 375                 380

Asn Gly Leu Ser Leu Met Leu Arg Ala Glu Gln Asn Asp Phe Ile Pro
385                 390                 395                 400

Leu Leu Ser Thr Val Thr Gly Ala Arg Val Met Val His Gly Gln Asp
                405                 410                 415

Glu Pro Ala Phe Met Asp Asp Gly Gly Phe Asn Leu Arg Pro Gly Val
            420                 425                 430

Glu Thr Ser Ile Ser Met Arg Lys Glu Thr Leu Asp Arg Leu Gly Gly
        435                 440                 445

Asp Tyr Gly Asp Cys Thr Lys Asn Gly Ser Asp Val Pro Val Glu Asn
    450                 455                 460

Leu Tyr Pro Ser Lys Tyr Thr Gln Gln Val Cys Ile His Ser Cys Phe
465                 470                 475                 480

Gln Glu Ser Met Ile Lys Glu Cys Gly Cys Ala Tyr Ile Phe Tyr Pro
                485                 490                 495

Arg Pro Gln Asn Val Glu Tyr Cys Asp Tyr Arg Lys His Ser Ser Trp
            500                 505                 510

Gly Tyr Cys Tyr Tyr Lys Leu Gln Val Asp Phe Ser Ser Asp His Leu
        515                 520                 525

Gly Cys Phe Thr Lys Cys Arg Lys Pro Cys Ser Val Thr Ser Tyr Gln
    530                 535                 540

Leu Ser Ala Gly Tyr Ser Arg Trp Pro Ser Val Thr Ser Gln Glu Trp
545                 550                 555                 560

Val Phe Gln Met Leu Ser Arg Gln Asn Asn Tyr Thr Val Asn Asn Lys
                565                 570                 575

Arg Asn Gly Val Ala Lys Val Asn Ile Phe Phe Lys Glu Leu Asn Tyr
            580                 585                 590

Lys Thr Asn Ser Glu Ser Pro Ser Val Thr Met Val Thr Leu Leu Ser
        595                 600                 605

Asn Leu Gly Ser Gln Trp Ser Leu Trp Phe Gly Ser Ser Val Leu Ser
    610                 615                 620

Val Val Glu Met Ala Glu Leu Val Phe Asp Leu Leu Val Ile Met Phe
625                 630                 635                 640

Leu Met Leu Leu Arg Arg Phe Arg Ser Arg Tyr Trp Ser Pro Gly Arg
                645                 650                 655

Gly Gly Arg Gly Ala Gln Glu Val Ala Ser Thr Leu Ala Ser Ser Pro
            660                 665                 670

Pro Ser His Phe Cys Pro His Pro Met Ser Leu Ser Leu Ser Gln Pro
        675                 680                 685

Gly Pro Ala Pro Ser Pro Ala Leu Thr Ala Pro Pro Pro Ala Tyr Ala
```

```
    690                 695                 700

Thr Leu Gly Pro Arg Pro Ser Pro Gly Gly Ser Ala Gly Ala Ser Ser
705                 710                 715                 720

Ser Thr Cys Pro Leu Gly Gly Pro
                725


<210> SEQ ID NO 24
<211> LENGTH: 3345
<212> TYPE: DNA
<213> ORGANISM: Homo sapiens

<400> SEQUENCE: 24

cttgcctgtc tgcgtctaaa gcccctgccc agagtccgcc ttctcaggtc cagtactccc     60

agttcacctg ccctcgggag ccctccttcc ttcggaaaac tcccggctct gactcctcct    120

cagcccctcc ccccgccctg ctcaccttta attgagatgc taatgagatt cctgtcgctt    180

ccatccctgg ccggccagcg ggcgggctcc ccagccaggc cgctgcacct gtcaggggaa    240

caagctggag gagcaggacc ctagacctct gcagcccata ccaggtctca tggaggggaa    300

caagctggag gagcaggact ctagccctcc acagtccact ccagggctca tgaaggggaa    360

caagcgtgag gagcaggggc tgggccccga acctgcggcg ccccagcagc ccacggcgga    420

ggaggaggcc ctgatcgagt tccaccgctc ctaccgagag ctcttcgagt tcttctgcaa    480

caacaccacc atccacggcg ccatccgcct ggtgtgctcc cagcacaacc gcatgaagac    540

ggccttctgg gcagtgctgt ggctctgcac ctttggcatg atgtactggc aattcggcct    600

gcttttcgga gagtacttca gctaccccgt cagcctcaac atcaacctca actcggacaa    660

gctcgtcttc cccgcagtga ccatctgcac cctcaatccc tacaggtacc cggaaattaa    720

agaggagctg gaggagctgg accgcatcac agagcagacg ctctttgacc tgtacaaata    780

cagctccttc accactctcg tggccggctc ccgcagccgt cgcgacctgc gggggactct    840

gccgcacccc ttgcagcgcc tgagggtccc gcccccgcct cacggggccc gtcgagcccg    900

tagcgtggcc tccagcttgc gggacaacaa cccccaggtg gactggaagg actggaagat    960

cggcttccag ctgtgcaacc agaacaaatc ggactgcttc taccagacat actcatcagg   1020

ggtggatgcg gtgagggagt ggtaccgctt ccactacatc aacatcctgt cgaggctgcc   1080

agagactctg ccatccctgg aggaggacac gctgggcaac ttcatcttcg cctgccgctt   1140

caaccaggtc tcctgcaacc aggcgaatta ctctcacttc caccacccga tgtatggaaa   1200

ctgctatact ttcaatgaca agaacaactc caacctctgg atgtcttcca tgcctggaat   1260

caacaacggt ctgtccctga tgctgcgcgc agagcagaat gacttcattc ccctgctgtc   1320

cacagtgact ggggcccggg taatggtgca cgggcaggat gaacctgcct ttatggatga   1380

tggtggcttt aacttgcggc ctggcgtgga gacctccatc agcatgagga aggaaaccct   1440

ggacagactt gggggcgatt atggcgactg caccaagaat ggcagtgatg ttcctgttga   1500

gaacctttac ccttcaaagt acacacagca ggtgtgtatt cactcctgct tccaggagag   1560

catgatcaag gagtgtggct gtgcctacat cttctatccg cggccccaga acgtggagta   1620

ctgtgactac agaaagcaca gttcctgggg gtactgctac tataagctcc aggttgactt   1680

ctcctcagac cacctgggct gtttcaccaa gtgccggaag ccatgcagcg tgaccagcta   1740

ccagctctct gctggttact cacgatggcc ctcggtgaca tcccaggaat gggtcttcca   1800

gatgctatcg cgacagaaca attacaccgt caacaacaag agaaatggag tggccaaagt   1860

caacatcttc ttcaaggagc tgaactacaa aaccaattct gagtctccct ctgtcacgat   1920
```

```
ggtcaccctc ctgtccaacc tgggcagcca gtggagcctg tggttcggct cctcggtgtt   1980

gtctgtggtg gagatggctg agctcgtctt tgacctgctg gtcatcatgt tcctcatgct   2040

gctccgaagg ttccgaagcc gatactggtc tccaggccga gggggcaggg gtgctcagga   2100

ggtagcctcc accctggcat cctcccctcc ttcccacttc tgcccccacc ccatgtctct   2160

gtccttgtcc cagccaggcc ctgctccctc tccagccttg acagcccctc cccctgccta   2220

tgccaccctg ggcccccgcc catctccagg gggctctgca ggggccagtt cctccacctg   2280

tcctctgggg gggccctgag agggaaggag aggtttctca caccaaggca gatgctcctc   2340

tggtgggagg gtgctggccc tggcaagatt gaaggatgtg cagggcttcc tctcagagcc   2400

gcccaaactg ccgttgatgt gtggagggga agcaagatgg gtaagggctc aggaagttgc   2460

tccaagaaca gtagctgatg aagctgccca gaagtgcctt ggctccagcc ctgtacccct   2520

tggtactgcc tctgaacact ctggtttccc cacccaactg cggctaagtc tctttttccc   2580

ttggatcagc caagcgaaac ttggagcttt gacaaggaac tttcctaaga aaccgctgat   2640

aaccaggaca aaacacaacc aagggtacac gcaggcatgc acgggtttcc tgcccagcga   2700

cggcttaagc cagcccccga ctggcctggc cacactgctc tccagtagca cagatgtctg   2760

ctcctcctct tgaacttggg tgggaaaccc cacccaaaag ccccctttgt tacttaggca   2820

attccccttc cctgactccc gagggctagg gctagagcag acccgggtaa gtaaaggcag   2880

acccagggct cctctagcct catacccgtg ccctcacaga gccatgcccc ggcacctctg   2940

ccctgtgtct ttcatacctc tacatgtctg cttgagatat ttcctcagcc tgaaagtttc   3000

cccaaccatc tgccagagaa ctcctatgca tcccttagaa ccctgctcag acaccattac   3060

ttttgtgaac gcttctgcca catcttgtct tccccaaaat tgatcactcc gccttctcct   3120

gggctcccgt agcacactat aacatctgct ggagtgttgc tgttgcacca tactttcttg   3180

tacatttgtg tctcccttcc caactagact gtaagtgcct tgcggtcagg gactgaatct   3240

tgcccgttta tgtatgctcc atgtctagcc catcatcctg cttggagcaa gtaggcagga   3300

gctcaataaa tgtttgttgc atgaaggaaa aaaaaaaaaa aaaaa                   3345
```

<210> SEQ ID NO 25
<211> LENGTH: 669
<212> TYPE: PRT
<213> ORGANISM: Homo sapiens

<400> SEQUENCE: 25

```
Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
            20                  25                  30

Pro Glu Pro Ala Ala Pro Gln Gln Pro Thr Ala Glu Glu Glu Ala Leu
        35                  40                  45

Ile Glu Phe His Arg Ser Tyr Arg Glu Leu Phe Glu Phe Phe Cys Asn
    50                  55                  60

Asn Thr Thr Ile His Gly Ala Ile Arg Leu Val Cys Ser Gln His Asn
65                  70                  75                  80

Arg Met Lys Thr Ala Phe Trp Ala Val Leu Trp Leu Cys Thr Phe Gly
                85                  90                  95

Met Met Tyr Trp Gln Phe Gly Leu Leu Phe Gly Glu Tyr Phe Ser Tyr
            100                 105                 110

Pro Val Ser Leu Asn Ile Asn Leu Asn Ser Asp Lys Leu Val Phe Pro
```

```
        115                 120                 125

Ala Val Thr Ile Cys Thr Leu Asn Pro Tyr Arg Tyr Pro Glu Ile Lys
    130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
                165                 170                 175

Arg Arg Asp Leu Arg Gly Thr Leu Pro His Pro Leu Gln Arg Leu Arg
            180                 185                 190

Val Pro Pro Pro Pro His Gly Ala Arg Arg Ala Arg Ser Val Ala Ser
        195                 200                 205

Ser Leu Arg Asp Asn Asn Pro Gln Val Asp Trp Lys Asp Trp Lys Ile
    210                 215                 220

Gly Phe Gln Leu Cys Asn Gln Asn Lys Ser Asp Cys Phe Tyr Gln Thr
225                 230                 235                 240

Tyr Ser Ser Gly Val Asp Ala Val Arg Glu Trp Tyr Arg Phe His Tyr
                245                 250                 255

Ile Asn Ile Leu Ser Arg Leu Pro Glu Thr Leu Pro Ser Leu Glu Glu
            260                 265                 270

Asp Thr Leu Gly Asn Phe Ile Phe Ala Cys Arg Phe Asn Gln Val Ser
        275                 280                 285

Cys Asn Gln Ala Asn Tyr Ser His Phe His His Pro Met Tyr Gly Asn
    290                 295                 300

Cys Tyr Thr Phe Asn Asp Lys Asn Asn Ser Asn Leu Trp Met Ser Ser
305                 310                 315                 320

Met Pro Gly Ile Asn Asn Gly Leu Ser Leu Met Leu Arg Ala Glu Gln
                325                 330                 335

Asn Asp Phe Ile Pro Leu Leu Ser Thr Val Thr Gly Ala Arg Val Met
            340                 345                 350

Val His Gly Gln Asp Glu Pro Ala Phe Met Asp Asp Gly Gly Phe Asn
        355                 360                 365

Leu Arg Pro Gly Val Glu Thr Ser Ile Ser Met Arg Lys Glu Thr Leu
    370                 375                 380

Asp Arg Leu Gly Gly Asp Tyr Gly Asp Cys Thr Lys Asn Gly Ser Asp
385                 390                 395                 400

Val Pro Val Glu Asn Leu Tyr Pro Ser Lys Tyr Thr Gln Gln Val Cys
                405                 410                 415

Ile His Ser Cys Phe Gln Glu Ser Met Ile Lys Glu Cys Gly Cys Ala
            420                 425                 430

Tyr Ile Phe Tyr Pro Arg Pro Gln Asn Val Glu Tyr Cys Asp Tyr Arg
        435                 440                 445

Lys His Ser Ser Trp Gly Tyr Cys Tyr Tyr Lys Leu Gln Val Asp Phe
    450                 455                 460

Ser Ser Asp His Leu Gly Cys Phe Thr Lys Cys Arg Lys Pro Cys Ser
465                 470                 475                 480

Val Thr Ser Tyr Gln Leu Ser Ala Gly Tyr Ser Arg Trp Pro Ser Val
                485                 490                 495

Thr Ser Gln Glu Trp Val Phe Gln Met Leu Ser Arg Gln Asn Asn Tyr
            500                 505                 510

Thr Val Asn Asn Lys Arg Asn Gly Val Ala Lys Val Asn Ile Phe Phe
        515                 520                 525

Lys Glu Leu Asn Tyr Lys Thr Asn Ser Glu Ser Pro Ser Val Thr Met
    530                 535                 540
```

```
Val Thr Leu Leu Ser Asn Leu Gly Ser Gln Trp Ser Leu Trp Phe Gly
545                 550                 555                 560

Ser Ser Val Leu Ser Val Val Glu Met Ala Glu Leu Val Phe Asp Leu
                565                 570                 575

Leu Val Ile Met Phe Leu Met Leu Leu Arg Arg Phe Arg Ser Arg Tyr
            580                 585                 590

Trp Ser Pro Gly Arg Gly Gly Arg Gly Ala Gln Glu Val Ala Ser Thr
        595                 600                 605

Leu Ala Ser Ser Pro Pro Ser His Phe Cys Pro His Pro Met Ser Leu
    610                 615                 620

Ser Leu Ser Gln Pro Gly Pro Ala Pro Ser Pro Ala Leu Thr Ala Pro
625                 630                 635                 640

Pro Pro Ala Tyr Ala Thr Leu Gly Pro Arg Pro Ser Pro Gly Gly Ser
                645                 650                 655

Ala Gly Ala Ser Ser Ser Thr Cys Pro Leu Gly Gly Pro
            660                 665


<210> SEQ ID NO 26
<211> LENGTH: 3970
<212> TYPE: DNA
<213> ORGANISM: Homo sapiens

<400> SEQUENCE: 26

gcacccaggt cgggcggtgg gggcgagcgg aggggctgag ggcggagagg gcctggcggg      60

ccgctgctgc gggccagggg acgggggcgg agccggagcc ggagccgacg ggcggtggcc     120

gcactgggac cccggaatcc cgcgcgctgc ccacgattcg cttctgagga acctagaaag     180

attgtacaat gaatggtgat tctcgtgctg cggtggtgac ctcaccaccc ccgaccacag     240

cccctcacaa ggagaggtac ttcgaccgag tagatgagaa caacccagag tacttgaggg     300

agaggaacat ggcaccagac cttcgccagg acttcaacat gatggagcaa aagaagaggg     360

tgtccatgat tctgcaaagc cctgctttct gtgaagaatt ggaatcaatg atacaggagc     420

aatttaagaa ggggaagaac cccacaggcc tattggcatt acagcagatt gcagatttta     480

tgaccacgaa tgtaccaaat gtctacccag cagctccgca aggagggatg gctgccttaa     540

acatgagtct tggtatggtg actcctgtga acgatcttag aggatctgat tctattgcgt     600

atgacaaagg agagaagtta ttacggtgta aattggcagc gttttataga ctagcagatc     660

tctttgggtg gtctcagctt atctacaatc atatcacaac cagagtgaac tccgagcagg     720

aacacttcct cattgtccct tttgggcttc tttacagtga agtgactgca tccagtttgg     780

ttaagatcaa tctacaagga gatatagtag atcgtggaag cactaatctg ggagtgaatc     840

aggccggctt caccttacac tctgcaattt atgctgcacg cccggacgtg aagtgcgtcg     900

tgcacattca caccccagca ggggctgcgg tctctgcaat gaaatgtggc ctcttgccaa     960

tctccccgga ggcgctttcc cttggagaag tggcttatca tgactaccat ggcattctgg    1020

ttgatgaaga ggaaaaagtt ttgattcaga aaaatctggg gcctaaaagc aaggttctta    1080

ttctccggaa ccatgggctc gtgtcagttg gagagagcgt tgaggaggcc ttctattaca    1140

tccataacct tgtggttgcc tgtgagatcc aggttcgaac tctggccagt gcaggaggac    1200

cagacaactt agtcctgctg aatcctgaga agtacaaagc caagtcccgt tccccagggt    1260

ctccggtagg ggaaggcact ggatcgcctc ccaagtggca gattggtgag caggaatttg    1320

aagccctcat gcggatgctc gataatctgg gctacagaac tggctaccct tatcgatacc    1380
```

```
ctgctctgag agagaagtct aaaaaataca gcgatgtgga ggttcctgct agtgtcacag   1440
gttactcctt tgctagtgac ggtgattcgg gcacttgctc cccactcaga cacagttttc   1500
agaagcagca gcgggagaag acaagatggc tgaactctgg ccggggcgac gaagcttccg   1560
aggaagggca gaatggaagc agtcccaagt cgaagactaa gtggactaaa gaggatggac   1620
atagaacttc cacctctgct gtccctaacc tgtttgttcc attgaacact aacccaaaag   1680
aggtccagga gatgaggaac aagatccgag agcagaattt acaggacatt aagacggctg   1740
gccctcagtc ccaggttttg tgtggtgtag tgatggacag gagcctcgtc cagggagagc   1800
tggtgacggc ctccaaggcc atcattgaaa aggagtacca gccccacgtc attgtgagca   1860
ccacgggccc caaccccttc accacactca cagaccgtga gctggaggag taccgcaggg   1920
aggtggagag gaagcagaag ggctctgaag agaatctgga cgaggctaga gaacagaaag   1980
aaaagagtcc tccagaccag cctgcggtcc cccacccgcc tcccagcact cccatcaagc   2040
tggaggaaga ccttgtgccg gagccgacta ctggagatga cagtgatgct gccaccttta   2100
agccaactct ccccgatctg tcccctgatg aaccttcaga agcactcggc ttcccaatgt   2160
tagagaagga ggaggaagcc catagacccc caagccccac tgaggcccct actgaggcca   2220
gccccgagcc agccccagac ccagccccgg tggctgaaga ggctgccccc tcagctgtcg   2280
aggagggggc cgccgcggac cctggcagcg atgggtctcc aggcaagtcc ccgtccaaaa   2340
agaagaagaa gttccgtacc ccgtcctttc tgaagaagag caagaagaag agtgactcct   2400
gaaagccctg cgctaacact gtcctgtccg gagcgaccct ggctctgcca gcgtccccgg   2460
ccacgtctgt gctctgtcct tgtgtaatgg aatgcaaaaa agccaagccc tccgcctaga   2520
ggtcccctca cgtgaccagc cccgtgtagc ccccgggctga cccagtgtgt gctcagcagc   2580
cccaccccac cctgcccctt gtcctctcag agcctcagct tctgggggag acatgctctc   2640
cccacagggg ggaggcacta agtcatggtc ctggctggaa ggtactgaag gcttctgcag   2700
ctttggctgc acgtcaccct cctgagcctc acctttcctg ccgtccctcc tgttgtgaaa   2760
tcaccacatt ctgtctctgc ttggcttccc ctccacccta aagtctcagg tgacggactc   2820
agactcctgg cttcatgtgg cattctctct gctcagtgat ctcacttaaa tctatataca   2880
aagccttggt cccgtgaaaa cactcgtgtg cccaccagcg gccttgaaga ggcaggtctg   2940
ggccagatgc tgggcaggaa accccagcgg cagatgggcc tgtgtgcacc caacgtgatg   3000
ctatgcatgt ctgaccgacg atccctcgac cagaatcaga ttcaggagct cagtttcttt   3060
ttcacttggg tctctggatt cctgtcatag ggaaggtata tcaggagggg aagaggcctt   3120
tctagaattt tctttgagca ggtttacaat ttagcttaca tttttcgact gtgaacgtga   3180
ataggctgct ttttgctttc ttctttccag accccacagt agagcacttt tcacttattt   3240
gggggaggct tcaggggact gttctcacct taactcagcc agaaagatgc cctagttgtg   3300
atcaaaggta actcgaggtg gagggtagcc ctggggcccc tcgacatcac cgtcattgat   3360
ggagcctgaa ccgtgtgctc ctcggcagat gctgttgttg ttacttccct ccaagaggct   3420
ggaaaagggc tcagagctgc tgagcaggaa ccggagggtg acccatttca ggaggtgccg   3480
gtaccagcct gactaggtac aggcaagctt gtgtgggccc aacaggccct tggtagagct   3540
ggtgccagat gtgggctcag atcctgggca tgatgggccg agccacctcg gatcccactg   3600
attggccagc cgagcgagaa ccaggctgct gcatggcact gaccgccgct tccagcttcc   3660
tctgagccgc agggcctgct acgcgggcaa gcgtgctgcc tctcttctgt gtcgttttgt   3720
tgccaaggca gaatgaaaag tccttaaccg tggactcttc ctttatcccc tcctttaccc   3780
```

cacatatgca atgactttta attttcactt ttgtagttta atcctttgta ttacaacatg 3840
aaatatagtt gcatatatgg acaccgactt gggaggacag gtcctgaatg tcctttctcc 3900
agtgtaacat gttttactca caaataaaat tctttcagca agttccttgt ctaaaaaaaa 3960
aaaaaaaaaa 3970

<210> SEQ ID NO 27
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = G or T

<400> SEQUENCE: 27
ccggggcgac gaagcttccg aggaanggca gaatggaagc agtcccaagt c 51

<210> SEQ ID NO 28
<211> LENGTH: 737
<212> TYPE: PRT
<213> ORGANISM: Homo sapiens

<400> SEQUENCE: 28

Met Asn Gly Asp Ser Arg Ala Ala Val Val Thr Ser Pro Pro Pro Thr
1 5 10 15

Thr Ala Pro His Lys Glu Arg Tyr Phe Asp Arg Val Asp Glu Asn Asn
20 25 30

Pro Glu Tyr Leu Arg Glu Arg Asn Met Ala Pro Asp Leu Arg Gln Asp
35 40 45

Phe Asn Met Met Glu Gln Lys Lys Arg Val Ser Met Ile Leu Gln Ser
50 55 60

Pro Ala Phe Cys Glu Glu Leu Glu Ser Met Ile Gln Glu Gln Phe Lys
65 70 75 80

Lys Gly Lys Asn Pro Thr Gly Leu Leu Ala Leu Gln Gln Ile Ala Asp
85 90 95

Phe Met Thr Thr Asn Val Pro Asn Val Tyr Pro Ala Ala Pro Gln Gly
100 105 110

Gly Met Ala Ala Leu Asn Met Ser Leu Gly Met Val Thr Pro Val Asn
115 120 125

Asp Leu Arg Gly Ser Asp Ser Ile Ala Tyr Asp Lys Gly Glu Lys Leu
130 135 140

Leu Arg Cys Lys Leu Ala Ala Phe Tyr Arg Leu Ala Asp Leu Phe Gly
145 150 155 160

Trp Ser Gln Leu Ile Tyr Asn His Ile Thr Thr Arg Val Asn Ser Glu
165 170 175

Gln Glu His Phe Leu Ile Val Pro Phe Gly Leu Leu Tyr Ser Glu Val
180 185 190

Thr Ala Ser Ser Leu Val Lys Ile Asn Leu Gln Gly Asp Ile Val Asp
195 200 205

Arg Gly Ser Thr Asn Leu Gly Val Asn Gln Ala Gly Phe Thr Leu His
210 215 220

Ser Ala Ile Tyr Ala Ala Arg Pro Asp Val Lys Cys Val Val His Ile
225 230 235 240

His Thr Pro Ala Gly Ala Ala Val Ser Ala Met Lys Cys Gly Leu Leu
245 250 255

-continued

```
Pro Ile Ser Pro Glu Ala Leu Ser Leu Gly Glu Val Ala Tyr His Asp
            260                 265                 270

Tyr His Gly Ile Leu Val Asp Glu Glu Glu Lys Val Leu Ile Gln Lys
        275                 280                 285

Asn Leu Gly Pro Lys Ser Lys Val Leu Ile Leu Arg Asn His Gly Leu
    290                 295                 300

Val Ser Val Gly Glu Ser Val Glu Glu Ala Phe Tyr Tyr Ile His Asn
305                 310                 315                 320

Leu Val Val Ala Cys Glu Ile Gln Val Arg Thr Leu Ala Ser Ala Gly
                325                 330                 335

Gly Pro Asp Asn Leu Val Leu Leu Asn Pro Glu Lys Tyr Lys Ala Lys
            340                 345                 350

Ser Arg Ser Pro Gly Ser Pro Val Gly Glu Gly Thr Gly Ser Pro Pro
        355                 360                 365

Lys Trp Gln Ile Gly Glu Gln Glu Phe Glu Ala Leu Met Arg Met Leu
    370                 375                 380

Asp Asn Leu Gly Tyr Arg Thr Gly Tyr Pro Tyr Arg Tyr Pro Ala Leu
385                 390                 395                 400

Arg Glu Lys Ser Lys Lys Tyr Ser Asp Val Glu Val Pro Ala Ser Val
                405                 410                 415

Thr Gly Tyr Ser Phe Ala Ser Asp Gly Asp Ser Gly Thr Cys Ser Pro
            420                 425                 430

Leu Arg His Ser Phe Gln Lys Gln Gln Arg Glu Lys Thr Arg Trp Leu
        435                 440                 445

Asn Ser Gly Arg Gly Asp Glu Ala Ser Glu Glu Gly Gln Asn Gly Ser
    450                 455                 460

Ser Pro Lys Ser Lys Thr Lys Trp Thr Lys Glu Asp Gly His Arg Thr
465                 470                 475                 480

Ser Thr Ser Ala Val Pro Asn Leu Phe Val Pro Leu Asn Thr Asn Pro
                485                 490                 495

Lys Glu Val Gln Glu Met Arg Asn Lys Ile Arg Glu Gln Asn Leu Gln
            500                 505                 510

Asp Ile Lys Thr Ala Gly Pro Gln Ser Gln Val Leu Cys Gly Val Val
        515                 520                 525

Met Asp Arg Ser Leu Val Gln Gly Glu Leu Val Thr Ala Ser Lys Ala
    530                 535                 540

Ile Ile Glu Lys Glu Tyr Gln Pro His Val Ile Val Ser Thr Thr Gly
545                 550                 555                 560

Pro Asn Pro Phe Thr Thr Leu Thr Asp Arg Glu Leu Glu Glu Tyr Arg
                565                 570                 575

Arg Glu Val Glu Arg Lys Gln Lys Gly Ser Glu Glu Asn Leu Asp Glu
            580                 585                 590

Ala Arg Glu Gln Lys Glu Lys Ser Pro Pro Asp Gln Pro Ala Val Pro
        595                 600                 605

His Pro Pro Pro Ser Thr Pro Ile Lys Leu Glu Glu Asp Leu Val Pro
    610                 615                 620

Glu Pro Thr Thr Gly Asp Asp Ser Asp Ala Ala Thr Phe Lys Pro Thr
625                 630                 635                 640

Leu Pro Asp Leu Ser Pro Asp Glu Pro Ser Glu Ala Leu Gly Phe Pro
                645                 650                 655

Met Leu Glu Lys Glu Glu Glu Ala His Arg Pro Pro Ser Pro Thr Glu
            660                 665                 670

Ala Pro Thr Glu Ala Ser Pro Glu Pro Ala Pro Asp Pro Ala Pro Val
```

```
        675                 680                 685

Ala Glu Glu Ala Ala Pro Ser Ala Val Glu Glu Gly Ala Ala Ala Asp
    690                 695                 700

Pro Gly Ser Asp Gly Ser Pro Gly Lys Ser Pro Ser Lys Lys Lys Lys
705                 710                 715                 720

Lys Phe Arg Thr Pro Ser Phe Leu Lys Lys Ser Lys Lys Lys Ser Asp
                725                 730                 735

Ser


<210> SEQ ID NO 29
<211> LENGTH: 5582
<212> TYPE: DNA
<213> ORGANISM: Homo sapiens

<400> SEQUENCE: 29

ctggcccctc cctggacacc caggcgacaa tggcagaact gcccacaaca gagacgcctg      60

gggacgccac tttgtgcagc gggcgcttca ccatcagcac actgctgagc agtgatgagc     120

cctctccacc agctgcctat gacagcagcc accccagcca cctgacccac agcagcacct     180

tctgcatgcg cacctttggc tacaacacga tcgatgtggt gcccacatat gagcactatg     240

ccaacagcac ccagcctggt gagccccgga aggtccggcc cacactggct gacctgcact     300

ccttcctcaa gcaggaaggc agacacctgc atgccctggc ctttgacagc cggcccagcc     360

acgagatgac tgatgggctg gtggagggcg aggcaggcac cagcagcgag aagaaccccg     420

aggagccagt gcgcttcggc tgggtcaagg gggtgatgat tcgttgcatg ctcaacattt     480

ggggcgtgat cctctacctg cggctgccct ggattacggc ccaggcaggc atcgtcctga     540

cctggatcat catcctgctg tcggtcacgg tgacctccat cacaggcctc tccatctcag     600

ccatctccac caatggcaag gtcaagtcag gtggcaccta cttcctcatc tcccggagtc     660

tgggcccaga gcttgggggc tccatcggcc tcattttcgc tttcgccaat gccgtgggtg     720

tggccatgca cacggtgggc tttgcagaga ccgtgcggga cctgctccag gagtatgggg     780

cacccatcgt ggaccccatt aacgacatcc gcatcattgg cgtggtctcg gtcactgtgc     840

tgctggccat ctccctggct ggcatggagt gggagtccaa ggcccaggtg ctgttcttcc     900

ttgtcatcat ggtctccttt gccaactatt tagtggggac gctgatcccc ccatctgagg     960

acaaggcctc caaaggcttc ttcagctacc gggcggacat ttttgtccag aacttggtgc    1020

ctgactggcg gggtccagat ggcaccttct tcggaatgtt ctccatcttc ttcccctcgg    1080

ccacaggcat cctggcaggg gccaacatat ctggtgacct caaggaccct gctatagcca    1140

tccccaaggg gaccctcatg gccattttct ggacgaccat ttcctacctg gccatctcag    1200

ccaccattgg ctcctgcgtg gtgcgtgatg cctctggggt cctgaatgac acagtgaccc    1260

ctggctgggg tgcctgcgag gggctggcct gcagctatgg ctggaacttc accgagtgca    1320

cccagcagca cagctgccac tacggcctca tcaactatta ccagaccatg agcatggtgt    1380

caggcttcgc gcccctgatc acggctggca tcttcggggc caccctctcc tctgccctgg    1440

cctgccttgt ctctgctgcc aaagtcttcc agtgcctttg cgaggaccag ctgtacccac    1500

tgatcggctt cttcggcaaa ggctatggca agaacaagga gcccgtgcgt ggctacctgc    1560

tggcctacgc catcgctgtg gccttcatca tcatcgctga gctcaacacc atagccccca    1620

tcatttccaa cttcttcctc tgctcctatg ccctcatcaa cttcagctgc ttccacgcct    1680

ccatcaccaa ctcgcctggg tggagacctt cattccaata ctacaacaag tgggcggcgc    1740
```

-continued

```
tgtttggggc tatcatctcc gtggtcatca tgttcctcct cacctggtgg gcggccctca   1800
tcgccattgg cgtggtgctc ttcctcctgc tctatgtcat ctacaagaag ccagaggtaa   1860
attggggctc ctcggtacag gctggctcct acaacctggc cctcagctac tcggtgggcc   1920
tcaatgaggt ggaagaccac atcaagaact accgccccca gtgcctggtg ctcacggggc   1980
cccccaactt ccgcccggcc ctggtggact ttgtgggcac cttcacccgg aacctcagcc   2040
tgatgatctg tggccacgtg ctcatcggac cccacaagca gaggatgcct gagctccagc   2100
tcatcgccaa cgggcacacc aagtggctga acaagaggaa gatcaaggcc ttctactcgg   2160
atgtcattgc cgaggacctc cgcagaggcg tccagatcct catgcaggcc gcaggtctcg   2220
ggagaatgaa gcccaacatt ctggtggttg ggttcaagaa gaactggcag tcggctcacc   2280
cggccacagt ggaagactac attggcatcc tccatgatgc ctttgatttc aactatggcg   2340
tgtgtgtcat gaggatgcgg gagggactca acgtgtccaa gatgatgcag gcgcacatta   2400
accccgtgtt tgacccagcg gaggacggga aggaagccag cgccagaggt gccaggccat   2460
cagtctctgg cgctttggac cccaaggccc tggtgaagga ggagcaggcc accaccatct   2520
tccagtcgga gcagggcaag aagaccatag acatctactg gctctttgac gatggaggcc   2580
tcaccctcct cattccctat ctccttggcc gcaagaggag gtggagcaaa tgcaagatcc   2640
gtgtgttcgt aggcggccag attaacagga tggaccagga gagaaaggcg atcatttctc   2700
tgctgagcaa gttccgactg ggattccatg aagtccacat cctccctgac atcaaccaga   2760
accctcgggc tgagcacacc aagaggtttg aggacatgat tgcacccttc cgtctgaatg   2820
atggcttcaa ggatgaggcc actgtcaacg agatgcggcg ggactgcccc tggaagatct   2880
cagatgagga gattacgaag aacagagtca agtcccttcg gcaggtgagg ctgaatgaga   2940
ttgtgctgga ttactcccga gacgctgctc tcatcgtcat cactttgccc atagggagga   3000
aggggaagtg ccccagctcg ctgtacatgg cctggctgga gaccctgtcc caggacctca   3060
gacctccagt catcctgatc cgaggaaacc aggaaaacgt gctcaccttt tactgccagt   3120
aactccaggc tttgacatcc ctgtccacag ctctgagtgt gtgggataag ttggaacttg   3180
attgcctcta gtccacaggg atgagactca tgttctgttg cactttaagt ggcagcatct   3240
gatgatctca ccgaaaaaga tggtagattt ccaaatctgg ctggactcca cttccatggg   3300
acacattccc tgggtcttgt gtttataggc tagagaaata gcagatggag ctgcaaggaa   3360
aactctctaa agcatcctat tccttttaaa ggatttcttt tgattttgat gaccattaat   3420
taagagttca gtctttgatt tgtatgcaaa ttggagtccc aatgctgggc gtgaatcttg   3480
acagtttcta cagaccttcc tgggtgaaag ttcctaaatc atgccctgct tcctccaata   3540
ggagaatggg agcctcacct gtaggaccta caggctctct aaggaatgca ggtctctctc   3600
tgagcctcca cagccaggca aatacatata tatatatttt ttttttagat gaagtttttt   3660
ctcttgttgc ccaggctagg gtgtaatggc atgatctcag gtcactgcaa cctcctcccg   3720
ggttcaagca tttcttctgt ctcagcctcc cgaatagctg ggattacagg cacctgccat   3780
cacacgagct aatttttgta tttttagtag agatggggtt tcaccatgtt gaccaggctg   3840
gtgttgagct cctgacctca ggtgatccac ccacctcggt ctcccaaagt gctggggtta   3900
caggcctgag ccactgcgcc cggcccaggc aaatttcttg aaccacttct cactcccgtc   3960
actttcaata aggggtcttt gatgtcttca ctggttcttt ggacgaggga cttttcgaac   4020
ttttttggtt gcaacacaca gtaagaaata tacttcacac tgagacttgc agcgcacaca   4080
cacggaaacg accaaaacaa aaatgtcaca aaacaatact tacccttccc tgggggacgt   4140
```

```
cctccagtat gttctgttct gtttattttt cactgttggt tgcaatccaa taaaatgact   4200
ttgggatcca ctcatgggtg gggacccaca catttgaaag gcatggccac ctttctgttg   4260
tgccttgcat ttgtccacac acagggagtc tggctgagct ggggaaaggc cacggctggg   4320
tgtcattgcc attttcccag ctcatctcac cgggaagaaa agcagattga cagaacacgt   4380
gaggaggggt attgatggca ggagagtcaa aaaagagttt taaagaaggg gcaaggttga   4440
aggagtctag tggcaagggt aagatttcag gcatggttaa gaacagacga caaggatgtc   4500
aggaatgaag atgtggagag gggtgtagag atggcaaggt tggcaaggaa cagataggca   4560
ggagcaggtc caagccaagc ctagcccaag accaggtgaa aggagagggg aggaggagcc   4620
acctgcaaga gatggaaaga gcaggcggca gagggggctg gcagggaggg gctgttaaga   4680
gtggggttgg aggtgggaga gaagctagga caagggagat ggagaaagga cctatacctg   4740
gctcacggaa ggccttcagg tcactacacg ttgaacatcc ccagtgtttg agcccccaaa   4800
gctagggtgc aagagcactg ccatcgaatg ccagtgggtg aggccaagtg agggtatttg   4860
cagctctaga cataaccaag aagcgtaaag gtgagttgtt tggtggtacg actgcctgtg   4920
ccttcttccg atggcactgg ggtggctgaa ggaacagaca tctttgggtt tcatcagcct   4980
cctccaagac tgctgcagtg cctacacttt agacttcaga aggagactaa agacttctag   5040
aatttagaag gagatctgaa gtctcctttc tggagttaca acccaaagga tgttagcatt   5100
tctcaggtca tcccactgca aagcccagaa ggcttggggc tcccaggctg ctctgaagcc   5160
ccactgtctg accgcctcag ggcttgctac gagggactgg ggcacggcca agctgactag   5220
gaacagctct cgtgctcctg agggacctgg aggatgggcc tgcctcccag ccattgagct   5280
ggattctggg ataattctta actcgaaata aggggaagca tccatcaggg aatgctggcc   5340
tttctagagc cacgtagaaa acaattttct ggttcttcaa acctcaaaga gtccttggtc   5400
caaaaaacag aatgttttgg cttcgggtgt caaaaaaaaa attttcacga tgtcagaaat   5460
agtatgtttt taacaatagt aatagctttg taaaaaaata aaaagcttta acagcgaggc   5520
cataaacaat gaaatgaata aaaacggtgg tcattcagtc aacggaaaaa aaaaaaaaaa   5580
aa                                                                  5582
```

<210> SEQ ID NO 30
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or G

<400> SEQUENCE: 30

```
cccattaacg acatccgcat cattgncgtg gtctcggtca ctgtgctgct g              51
```

<210> SEQ ID NO 31
<211> LENGTH: 1030
<212> TYPE: PRT
<213> ORGANISM: Homo sapiens

<400> SEQUENCE: 31

```
Met Ala Glu Leu Pro Thr Thr Glu Thr Pro Gly Asp Ala Thr Leu Cys
1               5                   10                  15

Ser Gly Arg Phe Thr Ile Ser Thr Leu Leu Ser Ser Asp Glu Pro Ser
            20                  25                  30
```

```
Pro Pro Ala Ala Tyr Asp Ser Ser His Pro Ser His Leu Thr His Ser
        35                  40                  45

Ser Thr Phe Cys Met Arg Thr Phe Gly Tyr Asn Thr Ile Asp Val Val
    50                  55                  60

Pro Thr Tyr Glu His Tyr Ala Asn Ser Thr Gln Pro Gly Glu Pro Arg
65                  70                  75                  80

Lys Val Arg Pro Thr Leu Ala Asp Leu His Ser Phe Leu Lys Gln Glu
                85                  90                  95

Gly Arg His Leu His Ala Leu Ala Phe Asp Ser Arg Pro Ser His Glu
            100                 105                 110

Met Thr Asp Gly Leu Val Glu Gly Glu Ala Gly Thr Ser Ser Glu Lys
        115                 120                 125

Asn Pro Glu Glu Pro Val Arg Phe Gly Trp Val Lys Gly Val Met Ile
    130                 135                 140

Arg Cys Met Leu Asn Ile Trp Gly Val Ile Leu Tyr Leu Arg Leu Pro
145                 150                 155                 160

Trp Ile Thr Ala Gln Ala Gly Ile Val Leu Thr Trp Ile Ile Ile Leu
                165                 170                 175

Leu Ser Val Thr Val Thr Ser Ile Thr Gly Leu Ser Ile Ser Ala Ile
            180                 185                 190

Ser Thr Asn Gly Lys Val Lys Ser Gly Gly Thr Tyr Phe Leu Ile Ser
        195                 200                 205

Arg Ser Leu Gly Pro Glu Leu Gly Gly Ser Ile Gly Leu Ile Phe Ala
    210                 215                 220

Phe Ala Asn Ala Val Gly Val Ala Met His Thr Val Gly Phe Ala Glu
225                 230                 235                 240

Thr Val Arg Asp Leu Leu Gln Glu Tyr Gly Ala Pro Ile Val Asp Pro
                245                 250                 255

Ile Asn Asp Ile Arg Ile Ile Gly Val Val Ser Val Thr Val Leu Leu
            260                 265                 270

Ala Ile Ser Leu Ala Gly Met Glu Trp Glu Ser Lys Ala Gln Val Leu
        275                 280                 285

Phe Phe Leu Val Ile Met Val Ser Phe Ala Asn Tyr Leu Val Gly Thr
    290                 295                 300

Leu Ile Pro Pro Ser Glu Asp Lys Ala Ser Lys Gly Phe Phe Ser Tyr
305                 310                 315                 320

Arg Ala Asp Ile Phe Val Gln Asn Leu Val Pro Asp Trp Arg Gly Pro
                325                 330                 335

Asp Gly Thr Phe Phe Gly Met Phe Ser Ile Phe Phe Pro Ser Ala Thr
            340                 345                 350

Gly Ile Leu Ala Gly Ala Asn Ile Ser Gly Asp Leu Lys Asp Pro Ala
        355                 360                 365

Ile Ala Ile Pro Lys Gly Thr Leu Met Ala Ile Phe Trp Thr Thr Ile
    370                 375                 380

Ser Tyr Leu Ala Ile Ser Ala Thr Ile Gly Ser Cys Val Val Arg Asp
385                 390                 395                 400

Ala Ser Gly Val Leu Asn Asp Thr Val Thr Pro Gly Trp Gly Ala Cys
                405                 410                 415

Glu Gly Leu Ala Cys Ser Tyr Gly Trp Asn Phe Thr Glu Cys Thr Gln
            420                 425                 430

Gln His Ser Cys His Tyr Gly Leu Ile Asn Tyr Tyr Gln Thr Met Ser
        435                 440                 445

Met Val Ser Gly Phe Ala Pro Leu Ile Thr Ala Gly Ile Phe Gly Ala
```

-continued

```
    450                 455                 460

Thr Leu Ser Ser Ala Leu Ala Cys Leu Val Ser Ala Ala Lys Val Phe
465                 470                 475                 480

Gln Cys Leu Cys Glu Asp Gln Leu Tyr Pro Leu Ile Gly Phe Phe Gly
                485                 490                 495

Lys Gly Tyr Gly Lys Asn Lys Glu Pro Val Arg Gly Tyr Leu Leu Ala
            500                 505                 510

Tyr Ala Ile Ala Val Ala Phe Ile Ile Ile Ala Glu Leu Asn Thr Ile
        515                 520                 525

Ala Pro Ile Ile Ser Asn Phe Phe Leu Cys Ser Tyr Ala Leu Ile Asn
    530                 535                 540

Phe Ser Cys Phe His Ala Ser Ile Thr Asn Ser Pro Gly Trp Arg Pro
545                 550                 555                 560

Ser Phe Gln Tyr Tyr Asn Lys Trp Ala Ala Leu Phe Gly Ala Ile Ile
                565                 570                 575

Ser Val Val Ile Met Phe Leu Leu Thr Trp Trp Ala Ala Leu Ile Ala
            580                 585                 590

Ile Gly Val Val Leu Phe Leu Leu Leu Tyr Val Ile Tyr Lys Lys Pro
        595                 600                 605

Glu Val Asn Trp Gly Ser Ser Val Gln Ala Gly Ser Tyr Asn Leu Ala
    610                 615                 620

Leu Ser Tyr Ser Val Gly Leu Asn Glu Val Glu Asp His Ile Lys Asn
625                 630                 635                 640

Tyr Arg Pro Gln Cys Leu Val Leu Thr Gly Pro Pro Asn Phe Arg Pro
                645                 650                 655

Ala Leu Val Asp Phe Val Gly Thr Phe Thr Arg Asn Leu Ser Leu Met
            660                 665                 670

Ile Cys Gly His Val Leu Ile Gly Pro His Lys Gln Arg Met Pro Glu
        675                 680                 685

Leu Gln Leu Ile Ala Asn Gly His Thr Lys Trp Leu Asn Lys Arg Lys
    690                 695                 700

Ile Lys Ala Phe Tyr Ser Asp Val Ile Ala Glu Asp Leu Arg Arg Gly
705                 710                 715                 720

Val Gln Ile Leu Met Gln Ala Ala Gly Leu Gly Arg Met Lys Pro Asn
                725                 730                 735

Ile Leu Val Val Gly Phe Lys Lys Asn Trp Gln Ser Ala His Pro Ala
            740                 745                 750

Thr Val Glu Asp Tyr Ile Gly Ile Leu His Asp Ala Phe Asp Phe Asn
        755                 760                 765

Tyr Gly Val Cys Val Met Arg Met Arg Glu Gly Leu Asn Val Ser Lys
    770                 775                 780

Met Met Gln Ala His Ile Asn Pro Val Phe Asp Pro Ala Glu Asp Gly
785                 790                 795                 800

Lys Glu Ala Ser Ala Arg Gly Ala Arg Pro Ser Val Ser Gly Ala Leu
                805                 810                 815

Asp Pro Lys Ala Leu Val Lys Glu Glu Gln Ala Thr Thr Ile Phe Gln
            820                 825                 830

Ser Glu Gln Gly Lys Lys Thr Ile Asp Ile Tyr Trp Leu Phe Asp Asp
        835                 840                 845

Gly Gly Leu Thr Leu Leu Ile Pro Tyr Leu Leu Gly Arg Lys Arg Arg
    850                 855                 860

Trp Ser Lys Cys Lys Ile Arg Val Phe Val Gly Gly Gln Ile Asn Arg
865                 870                 875                 880
```

```
Met Asp Gln Glu Arg Lys Ala Ile Ile Ser Leu Leu Ser Lys Phe Arg
                885                 890                 895

Leu Gly Phe His Glu Val His Ile Leu Pro Asp Ile Asn Gln Asn Pro
            900                 905                 910

Arg Ala Glu His Thr Lys Arg Phe Glu Asp Met Ile Ala Pro Phe Arg
        915                 920                 925

Leu Asn Asp Gly Phe Lys Asp Glu Ala Thr Val Asn Glu Met Arg Arg
    930                 935                 940

Asp Cys Pro Trp Lys Ile Ser Asp Glu Glu Ile Thr Lys Asn Arg Val
945                 950                 955                 960

Lys Ser Leu Arg Gln Val Arg Leu Asn Glu Ile Val Leu Asp Tyr Ser
                965                 970                 975

Arg Asp Ala Ala Leu Ile Val Ile Thr Leu Pro Ile Gly Arg Lys Gly
            980                 985                 990

Lys Cys Pro Ser Ser Leu Tyr Met Ala Trp Leu Glu Thr Leu Ser Gln
        995                 1000                1005

Asp Leu Arg Pro Pro Val Ile Leu Ile Arg Gly Asn Gln Glu Asn Val
    1010                1015                1020

Leu Thr Phe Tyr Cys Gln
1025                1030
```

<210> SEQ ID NO 32

<400> SEQUENCE: 32

000

<210> SEQ ID NO 33
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or T

<400> SEQUENCE: 33
cacttcctcc aaaaaaaaag aaaacnccat ttcccctcaa ctcttccagt t 51

<210> SEQ ID NO 34
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or G

<400> SEQUENCE: 34
aatgttaaca gtatagaaaa ttttanctca acaaatagag aatatcagta a 51

<210> SEQ ID NO 35
<211> LENGTH: 50
<212> TYPE: DNA
<213> ORGANISM: Artificial Sequence
<220> FEATURE:
<223> OTHER INFORMATION: A synthetic oligonucleotide

<400> SEQUENCE: 35
tcccatttct ctagacctgc tgcctataca gtcactttta tgtggtttcg 50

<210> SEQ ID NO 36
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 36
acgttggatg agacatgacg atgcccatgc 30

<210> SEQ ID NO 37
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 37
acgttggatg agcgccttct tgctggcac 29

<210> SEQ ID NO 38
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 38
acgttggatg ctgtgacagg atggaagact 30

<210> SEQ ID NO 39
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 39
acgttggatg tggacgtagg tgttgaaagc 30

<210> SEQ ID NO 40
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 40
acgttggatg tgttcgtcca caccttagtc 30

<210> SEQ ID NO 41
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 41
acgttggatg acaagatggc tgaactctgg 30

<210> SEQ ID NO 42
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 42
acgttggatg ggaatccagg agaataggtc 30

<210> SEQ ID NO 43
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 43
acgttggatg acaggctacc tggctttaac 30

<210> SEQ ID NO 44
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 44
acgttggatg gcctcgttgc tgcctcccg 29

<210> SEQ ID NO 45
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 45
acgttggatg atcagcagac ccatgcccg 29

<210> SEQ ID NO 46
<211> LENGTH: 28
<212> TYPE: DNA
<213> ORGANISM: Artificial Sequence
<220> FEATURE:
<223> OTHER INFORMATION: A synthetic oligonucleotide

<400> SEQUENCE: 46
acgttggatg agccctgcgc gcgcagca 28

<210> SEQ ID NO 47
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 47
acgttggatg tcaaccccat catctactgc 30

<210> SEQ ID NO 48
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 48
acgttggatg ctgacattgc cagctgtatc 30

<210> SEQ ID NO 49
<211> LENGTH: 30

<212> TYPE: DNA
<213> ORGANISM: Artificial Sequence
<220> FEATURE:
<223> OTHER INFORMATION: A synthetic oligonucleotide

<400> SEQUENCE: 49
acgttggatg gtagtggcac tggcatattc 30

<210> SEQ ID NO 50
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 50
acgttggatg gcaaccatca cagtactaag 30

<210> SEQ ID NO 51
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 51
acgttggatg cacaactgga agagttgagg 30

<210> SEQ ID NO 52
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 52
acgttggatg tggaccccat taacgacatc 30

<210> SEQ ID NO 53
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 53
acgttggatg tcaccttgga ctcccactc 29

<210> SEQ ID NO 54
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 54
acgttggatg cactttccat aaaagcaagg 30

<210> SEQ ID NO 55
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 55

```
acgttggatg gcaataattt tcccactatc                                      30


<210> SEQ ID NO 56
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 56

acgttggatg atgagagaca tgacgatgcc                                      30


<210> SEQ ID NO 57
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 57

acgttggatg gaacggcagc gccttcttg                                       29


<210> SEQ ID NO 58
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 58

acgttggatg gaaacagtga cagccaaatg                                      30


<210> SEQ ID NO 59
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 59

acgttggatg gtttttcagt tcctgaattt g                                    31


<210> SEQ ID NO 60
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 60

acacctcgtc ccttt                                                      15


<210> SEQ ID NO 61
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 61

ctggctgctc cctga                                                      15


<210> SEQ ID NO 62
<211> LENGTH: 17
<212> TYPE: DNA
<213> ORGANISM: Artificial Sequence
```

<220> FEATURE:
<223> OTHER INFORMATION: A synthetic oligonucleotide

<400> SEQUENCE: 62
actgcttcca ttctgcc 17

<210> SEQ ID NO 63
<211> LENGTH: 17
<212> TYPE: DNA
<213> ORGANISM: Artificial Sequence
<220> FEATURE:
<223> OTHER INFORMATION: A synthetic oligonucleotide

<400> SEQUENCE: 63
agtctctgta agtgccc 17

<210> SEQ ID NO 64
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 64
gtgcctcccg ccagcgaa 18

<210> SEQ ID NO 65
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 65
cgcgcgcagc agagcagt 18

<210> SEQ ID NO 66
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 66
agctgtatct gctccattca 20

<210> SEQ ID NO 67
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 67
tcctccaaaa aaaaagaaaa c 21

<210> SEQ ID NO 68
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 68
gttaccgaca tccgcatcat tg 22

<210> SEQ ID NO 69
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 69
taagtaattt gttatgggtt cc 22

<210> SEQ ID NO 70
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 70
ggaggggtcc ggcgcatggc ttc 23

<210> SEQ ID NO 71
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 71
caaatgttaa cagtatagaa aatttta 27

<210> SEQ ID NO 72
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 72
ttcagtccct cctgagcta 19

<210> SEQ ID NO 73
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 73
aaggtggatg cacaaagag 19

<210> SEQ ID NO 74
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 74
gtgcatctgt agcagtcctc 20

<210> SEQ ID NO 75
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 75
ccaaactgga atcaacagaa 20

<210> SEQ ID NO 76
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 76
gaagtggtct cgtctagcaa 20

<210> SEQ ID NO 77
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 77
cagagagaga ggtcccattt 20

<210> SEQ ID NO 78
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 78
ccactcaaac ctttcaacaa 20

<210> SEQ ID NO 79
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 79
tggacagaac aatctggaac 20

<210> SEQ ID NO 80
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 80
cccatttctc tagacctgct 20

<210> SEQ ID NO 81
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 81
gggatggtgt ctcgtacata 20

<210> SEQ ID NO 82

-continued

<211> LENGTH: 46
<212> TYPE: DNA
<213> ORGANISM: Artificial Sequence
<220> FEATURE:
<223> OTHER INFORMATION: A synthetic oligonucleotide

<400> SEQUENCE: 82
gaagagattg aacgtgtcgt tggcagaaac cggagcccct gcatgc 46

<210> SEQ ID NO 83
<211> LENGTH: 46
<212> TYPE: DNA
<213> ORGANISM: Artificial Sequence
<220> FEATURE:
<223> OTHER INFORMATION: A synthetic oligonucleotide

<400> SEQUENCE: 83
gaagagattg aacgtgtcgt tggcagaaac cggagcccct gcatgc 46

<210> SEQ ID NO 84
<211> LENGTH: 46
<212> TYPE: DNA
<213> ORGANISM: Artificial Sequence
<220> FEATURE:
<223> OTHER INFORMATION: A synthetic oligonucleotide
<221> NAME/KEY: misc_feature
<222> LOCATION: (1)...(46)
<223> OTHER INFORMATION: n = A,T,C or G

<400> SEQUENCE: 84
gaagagattg aacgtgtngt tggcagaaac cggagcccct gcatgc 46

<210> SEQ ID NO 85
<211> LENGTH: 46
<212> TYPE: DNA
<213> ORGANISM: Artificial Sequence
<220> FEATURE:
<223> OTHER INFORMATION: A synthetic oligonucleotide
<221> NAME/KEY: misc_feature
<222> LOCATION: (1)...(46)
<223> OTHER INFORMATION: n = A,T,C or G

<400> SEQUENCE: 85
gaagagattg aacgtgtcnt tggcagaaac cggagcccct gcatgc 46